(12) United States Patent
Brodney et al.

(10) Patent No.: US 9,611,264 B1
(45) Date of Patent: Apr. 4, 2017

(54) N-[2-(3-AMINO-2,5-DIMETHYL-1,1-DIOXIDO-5,6-DIHYDRO-2H-1,2,4-THIADIAZIN-5-YL)-1,3-THIAZOL-4-YL] AMIDES

(71) Applicant: Pfizer Inc., New York, NY (US)

(72) Inventors: Michael Aaron Brodney, Newton, MA (US); Christopher Ryan Butler, Canton, MA (US); Lei Zhang, Auburndale, MA (US); Brian Thomas O'Neill, Haddam, CT (US); Patrick Robert Verhoest, Newton, MA (US); Romelia del Carmen Salomon Ferrer, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/272,820

(22) Filed: Sep. 22, 2016

Related U.S. Application Data

(60) Provisional application No. 62/222,986, filed on Sep. 24, 2015.

(51) Int. Cl.
  *C07D 417/14* (2006.01)
(52) U.S. Cl.
  CPC .................. *C07D 417/14* (2013.01)
(58) Field of Classification Search
  CPC .................................................. C07D 417/14
  USPC ...................................... 544/6, 8; 514/222.5
  See application file for complete search history.

(56) References Cited

U.S. PATENT DOCUMENTS

| | | | |
|---|---|---|---|
| 5,750,349 A | 5/1998 | Suzuki et al. | |
| 7,115,600 B2 | 10/2006 | Wager et al. | |
| 7,285,293 B2 | 10/2007 | Castillo et al. | |
| 7,975,664 B2 | 7/2011 | Himsel et al. | |
| 8,158,620 B2 | 4/2012 | Suzuki et al. | |
| 8,198,269 B2 | 6/2012 | Motoki et al. | |
| 8,278,441 B2 | 10/2012 | Mergott et al. | |
| 8,729,071 B2 | 5/2014 | Scott et al. | |
| 8,822,456 B2 | 9/2014 | Brodney et al. | |
| 8,865,706 B2 | 10/2014 | Brodney et al. | |
| 8,933,221 B2 | 1/2015 | Brodney et al. | |
| 8,962,616 B2 | 2/2015 | Brodney et al. | |
| 9,045,498 B2 | 6/2015 | Brodney et al. | |
| 9,045,499 B2 | 6/2015 | Brodney et al. | |
| 9,192,612 B2 | 11/2015 | Brodney et al. | |
| 9,198,917 B2 | 12/2015 | Brodney et al. | |
| 9,233,981 B1 | 1/2016 | Brodney et al. | |
| 9,260,455 B2 | 2/2016 | Brodney et al. | |
| 9,315,520 B2 | 4/2016 | Brodney et al. | |
| 9,403,846 B2 | 8/2016 | Brodney et al. | |
| 9,428,523 B2 | 8/2016 | Brodney et al. | |
| 2003/0073655 A1 | 4/2003 | Shain | |
| 2003/0195205 A1 | 10/2003 | DeNinno et al. | |
| 2004/0192898 A1 | 9/2004 | Jia et al. | |
| 2004/0220186 A1 | 11/2004 | Bell et al. | |
| 2005/0019328 A1 | 1/2005 | Schenk | |
| 2005/0043354 A1 | 2/2005 | Wager et al. | |
| 2005/0048049 A1 | 3/2005 | Schenk | |
| 2005/0256135 A1 | 11/2005 | Lunn et al. | |
| 2005/0267009 A1 | 12/2005 | Deagle | |
| 2005/0267095 A1 | 12/2005 | Bernardelli et al. | |
| 2005/0267100 A1 | 12/2005 | Elliott et al. | |
| 2006/0057701 A1 | 3/2006 | Rosenthal et al. | |
| 2006/0106035 A1 | 5/2006 | Hendrix et al. | |
| 2006/0111372 A1 | 5/2006 | Hendrix et al. | |
| 2006/0178501 A1 | 8/2006 | Summers et al. | |
| 2007/0031416 A1 | 2/2007 | Shoji et al. | |
| 2007/0160616 A1 | 7/2007 | Rosenthal et al. | |
| 2007/0179175 A1 | 8/2007 | Lunn | |
| 2008/0096955 A1 | 4/2008 | Wager et al. | |

(Continued)

FOREIGN PATENT DOCUMENTS

| | | |
|---|---|---|
| EP | 0994728 | 10/1998 |
| EP | 1257584 | 10/2004 |

(Continued)

OTHER PUBLICATIONS

International Application No. PCT/IB2016/055399, filed Sep. 9, 2016, International Search Report and Written Opinion, mailed Nov. 2, 2016, 14 pages.

(Continued)

*Primary Examiner* — Kahsay Habte

(74) *Attorney, Agent, or Firm* — John A. Wichtowski

(57) ABSTRACT

The present invention is directed to compounds, tautomers and pharmaceutically acceptable salts of the compounds which are disclosed, wherein the compounds have the structure of Formula I,

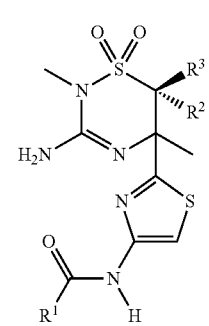

wherein the variables $R^1$, $R^2$ and $R^3$ are as defined in the specification. Corresponding pharmaceutical compositions, methods of treatment, methods of synthesis, and intermediates are also disclosed.

24 Claims, No Drawings

(56) References Cited

U.S. PATENT DOCUMENTS

| | | |
|---|---|---|
| 2008/0176925 A1 | 7/2008 | Butler et al. |
| 2009/0054482 A1 | 2/2009 | Chan et al. |
| 2010/0056618 A1 | 3/2010 | Mascitti et al. |
| 2010/0093999 A1 | 4/2010 | Motoki et al. |
| 2010/0285145 A1 | 11/2010 | Darout et al. |
| 2011/0009395 A1 | 1/2011 | Audia et al. |
| 2011/0027279 A1 | 2/2011 | Chain |
| 2011/0038861 A1 | 2/2011 | Rosenthal |
| 2011/0046122 A1 | 2/2011 | Andreini et al. |
| 2011/0207723 A1 | 8/2011 | Motoki et al. |
| 2012/0245155 A1 | 9/2012 | Yoshida et al. |
| 2013/0053373 A1 | 2/2013 | Brodney et al. |
| 2013/0296308 A1 | 11/2013 | Brodney et al. |
| 2014/0163015 A1 | 6/2014 | Brodney et al. |
| 2014/0228356 A1 | 8/2014 | Brodney et al. |
| 2014/0323474 A1 | 10/2014 | Brodney et al. |
| 2014/0364426 A1 | 12/2014 | Brodney et al. |
| 2015/0087637 A1 | 3/2015 | Brodney et al. |
| 2015/0133438 A1 | 5/2015 | Brodney et al. |
| 2015/0224110 A1 | 8/2015 | Brodney et al. |
| 2015/0231144 A1 | 8/2015 | Brodney et al. |
| 2015/0239908 A1 | 8/2015 | Brodney et al. |
| 2015/0291621 A1 | 10/2015 | Brodney et al. |
| 2015/0376207 A1 | 12/2015 | Brodney et al. |
| 2016/0002264 A1 | 1/2016 | Brodney et al. |
| 2016/0152637 A1 | 6/2016 | Brodney et al. |

FOREIGN PATENT DOCUMENTS

| | | |
|---|---|---|
| EP | 2332943 | 6/2011 |
| EP | 2511269 | 10/2012 |
| WO | 9844955 | 10/1998 |
| WO | 0220521 | 3/2002 |
| WO | 03072197 | 9/2003 |
| WO | 2004032868 | 4/2004 |
| WO | 2005025616 | 3/2005 |
| WO | 2005049616 | 11/2005 |
| WO | 2005116014 | 12/2005 |
| WO | 2006069081 | 6/2006 |
| WO | 2006118959 | 11/2006 |
| WO | 2006120552 | 11/2006 |
| WO | 2006126081 | 11/2006 |
| WO | 2006126082 | 11/2006 |
| WO | 2006126083 | 11/2006 |
| WO | 2006136924 | 12/2006 |
| WO | 2007063385 | 6/2007 |
| WO | 2007069053 | 6/2007 |
| WO | 2007088450 | 8/2007 |
| WO | 2007088462 | 9/2007 |
| WO | 2007099423 | 9/2007 |
| WO | 2007105053 | 9/2007 |
| WO | 2007122466 | 11/2007 |
| WO | 2007122482 | 11/2007 |
| WO | 2007138431 | 12/2007 |
| WO | 2008065508 | 6/2008 |
| WO | 2009016462 | 2/2009 |
| WO | 2009091016 | 7/2009 |
| WO | 2009144554 | 12/2009 |
| WO | 2009144555 | 12/2009 |
| WO | 2010013161 | 2/2010 |
| WO | 2010038686 | 4/2010 |
| WO | 2010086820 | 8/2010 |
| WO | 2010103437 | 9/2010 |
| WO | 2010103438 | 9/2010 |
| WO | 2010106457 | 9/2010 |
| WO | 2010140092 | 12/2010 |
| WO | 2011005611 | 1/2011 |
| WO | 2011009898 | 1/2011 |
| WO | 2011044181 | 4/2011 |
| WO | 2011071109 | 6/2011 |
| WO | 2012098461 | 7/2012 |
| WO | 2012162334 | 11/2012 |
| WO | 2013030713 | 3/2013 |
| WO | 2013164730 | 11/2013 |
| WO | 2014045162 | 3/2014 |
| WO | 2014091352 | 6/2014 |
| WO | 2014097038 | 6/2014 |
| WO | 2014125394 | 8/2014 |
| WO | 2014125397 | 8/2014 |
| WO | 2015155626 | 10/2015 |

OTHER PUBLICATIONS

International Application No. PCT/IB2016/055580, filed Sep. 19, 2016, International Search Report and Written Opinion, mailed Oct. 24, 2016, 12 pages.

International Application No. PCT/IB2016/055536, filed Sep. 19, 2016, International Search Report and Written Opinion, mailed Oct. 25, 2016, 10 pages.

Alberti, K.G. et al., "The Metabolic Syndrome—A New Worldwide Definition," Lancet, Sep. 24-30, 2005, pp. 1059-1062, 366(9491).

Carpino, P.A., et al., "Diabetes Area Participation Analysis: A Review of Companies and Targets Described in the 2008-2010 Patent Literature", Expert Opinion on Therapeutic Patents, Dec. 2010, pp. 1627-1651, 20(12).

Chao, Edward, et al., "SGLT2 Inhibition—A Novel Strategy for Diabetes Treatment", Nature Reviews Drug Discovery, Jul. 2010, pp. 551-559, 9(7).

Demong, D.E. et al., "Chapter 8, Glucagon Receptor Antagonists for Type II Diabetes", Annual Reports in Medicinal Chemistry 2008, pp. 119-137, vol. 43.

Denmark, S.E., et al., "Allylation of Carbonyls: Methodology and Stereochemistry", Modern Carbonyl Chemistry, 2000, Chapter 10, pp. 299-401.

England, et al., "An Improved Synthesis of a Novel α1A Partial Agonist Including a New Two-Step Synthesis of 4-Fluoropyrazole", Tetrahedron Letters, May 26, 2010, pp. 2849-2851, 51(21).

English equivalent U.S. Pat. No. 8,158,620; Suzuki, et al., filed Jan. 16, 2009 for WO 2009091016, published Jun. 23, 2007.

Esterhazy, Daria, et al., "BACE2 Is a β Cell-Enriched Protease that Regulates Pancreatic β Cell Function and Mass", Cell Metabolism, Sep. 2011, pp. 365-377, 14(3).

Farah, M., et al., "Reduced BACE1 Activity Enhances Clearance of Myelin Debris and Regeneration of Axons in the Injured Peripheral Nervous System", Journal of Neuroscience, Apr. 13, 2011, pp. 5744-5754, 31(15).

Finnin, Barrie, et al., "Transdermal Penetration Enhancers Applications, Limitations, and Potential", Journal Pharmaceutical Sciences, Oct. 1999, pp. 955-958, 88(10).

Flack, H.D., "On Enantiomorph-Polarity Estimation", Acta Cryst., 1983, pp. 876-881, vol. A39.

Glenner, G., et al., "Amyloidosis of the Nervous System", Journal of Neurological Science, 1989, pp. 1-28, vol. 94.

Guidance for Industry, Q3C-Tables and List, U.S. Department of Health and Human Services, Food and Drug Administration, Center for Drug Evaluation and Research (CDER), Center for Biologics Evaluation and Research (CBER), Nov. 2003, ICH, Revision I.

Haan, J., et al., "Amyloid in Central Nervous System Disease", Clinical Neurology and Neurosurgery, 1990, pp. 305-310, 92(4).

Haleblian, John K., "Characterization of Habits and Crystalline Modification of Solids and Their Pharmaceutical Applications", Journal Pharmaceutical Sciences, Aug. 1975, pp. 1269-1288, 64(8).

Hooft, Rob, et al., "Determination of Absolute Structure Using Bayesian Statistics on Bijvoet differences", Journal of Applied Crystallography, Feb. 2008, pp. 96-103, 41(1).

International Application No. PCT/IB2012/054198, filed Aug. 17, 2012, International Search Report and Written Opinion, mailed Jan. 23, 2013, 14 pages.

International Application No. PCT/IB2013/053178, filed Apr. 22, 2013, International Search Report & Written Opinion, mailed Jul. 3, 2013, 10 pages.

International Application No. PCT/IB2013/058402, filed Sep. 9, 2013, International Search Report, mailed Dec. 16, 2013, 11 pages.

International Application No. PCT/IB2013/060456, filed Nov. 27, 2013, International Preliminary Report on Patentability, mailed Jun. 16, 2015, 5 pages.

(56) References Cited

OTHER PUBLICATIONS

International Application No. PCT/IB2013/060456, filed Nov. 27, 2013, International Search Report, mailed Feb. 21, 2014, 8 pages.
International Application No. PCT/IB2013/060633, filed Dec. 4, 2013, International Preliminary Report on Patentability, mailed Jun. 23, 2015.
International Application No. PCT/IB2013/060633, filed Dec. 4, 2013, International Search Report and Written Opinion, mailed Mar. 24, 2014.
International Application No. PCT/IB2014/0558760 filed Feb. 3, 2014, International Preliminary Report on Patentability and Written Opinion mailed Aug. 18, 2015, 7 pages.
International Application No. PCT/IB2014/0558760 filed Feb. 3, 2014, International Search Report and Written Opinion, mailed Mar. 13, 2015, 10 pages.
International Application No. PCT/IB2014/0558777 filed Feb. 4, 2014, International Preliminary Report on Patentability, mailed Aug. 18, 2015, 7 pages.
International Application No. PCT/IB2015/052279, filed Mar. 27, 2015, International Search Report and Written Opinion, mailed Jun. 24, 2015, 10 pages.
International Patent Application No. PCT/IB2014/058777, filed Feb. 4, 2014, International Search Report and Written Opinion, mailed Mar. 25, 2014, 11 pages.
Jones, R.M. et al., "Chapter 7, The Emergence of GPR119 Agonists as Anti-Diabetic Agents", Annual Reports in Medicinal Chemistry 2009, pp. 149-170, vol. 44.
Kharitonenkov, A. et al., "FGF21: A Novel Prospect for the Treatment of Metabolic Diseases", Current Opinion in Investigational Drugs, Apr. 2009, pp. 359-364, 10(4).
MacRae, Clare, et al., "Mercury: Visualization and Analysis of Crystal Structures", Journal of Applied Crystallography, Jun. 2006, pp. 453-457, 39(3).
Meakin, Paul, et al., "Reduction in BACE1 decreases body weight, protects against diet-induced obesity and enhances insulin sensitivity in mice", Biochemical Journal, Jan. 1, 2012, pp. 285-296, 441(1).
Medina, J.C., et al., "Chapter 5, GPR40 (FFAR1) Modulators", Annual Reports in Medicinal Chemistry 2008, pp. 75-85, vol. 43.
Miyaura, N., et al., "Palladium-Catalyzed Cross-Coupling Reactions of Organobom Compounds", Chemical Review, Nov. 1995, pp. 2457-2483, 95(7).
Olson, R., et al., "Secretase Inhibitors and Modulators for the Treatment of Alzheimer's Disease", Annual Reports in Medicinal Chemistry, 2007, pp. 27-47, vol. 42.
Sheppeck, J.E. II, et al., "A Convenient and Scaleable Procedure for Removing the Fmoc Group in Solution", Tetrahedron Letters, 2000, pp. 5329-5333, vol. 41(28).
Spek, A.L., "Single-Crystal Structure Validation with the Program PLATON", Journal of Applied Crystallography, Feb. 2003, pp. 7-13, 36(1).
Suzuki, Akira, "Recent advances in the cross-coupling reactions of organoboron derivatives with organic electrophiles 1995-1998", Journal Organometallic Chemistry, 1999, pp. 147-168, vol. 576.
Zhang, S. et al., "PTP1B as a Drug Target: Recent Developments in PTP1B Inhibitor Discovery", Drug Discovery Today, May 2007, pp. 373-381, 12(9/10).
Zhong, M., "TGR5 as a Therapeutic Target for Treating Obesity", Current Topics in Medicinal Chemistry, 2010, pp. 386-396, 10(4).
Zimmet, P.Z. et al., "The Metabolic Syndrome: Perhaps an Etiologic Mystery but Far From a Myth—Where Does the International Diabetes Federation Stand?," Medscape Diabetes & Endocrinology, Oct. 11, 2005, 8 pages, www.medscape.com, 7(2).

ID-[2-(3-AMINO-2,5-DIMETHYL-1,1-DIOXIDO-5,6-DIHYDRO-2H-1,2,4-THIADIAZIN-5-YL)-1,3-THIAZOL-4-YL] AMIDES

This application is a Non-Provisional application which claims the benefit under 35 U.S.C. 119(e) of U.S. Provisional Patent Application No. 62/222,986 filed on Sep. 24, 2015, the disclosure of which is hereby incorporated by reference in its entirety.

FIELD OF THE INVENTION

The present invention relates to small molecule compounds and pharmaceutically acceptable salts thereof that are inhibitors of β-site amyloid precursor protein (APP) Cleaving Enzyme 1 (BACE1) and inhibitors of BACE2. This invention relates to inhibiting the production of A-beta peptides that can contribute to the formation of neurological deposits of amyloid protein. The present invention also relates to the treatment of Alzheimer's disease (AD) and other neurodegenerative and/or neurological disorders, as well as the treatment of diabetes in mammals, including humans. More particularly, this invention relates to cyclic sulfonyl guanidine compounds and pharmaceutically acceptable salts thereof useful for the treatment of neurodegenerative and/or neurological disorders, such as AD and Down's syndrome, related to A-beta peptide production.

BACKGROUND OF THE INVENTION

Dementia results from a wide variety of distinctive pathological processes. The most common pathological processes causing dementia are Alzheimer's disease ("AD"), cerebral amyloid angiopathy ("CM") and prion-mediated diseases (see, e.g., Haan et al., Clin. Neurol. Neurosurg., 1990, 92(4):305-310; Glenner et al., J. Neurol. Sci., 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050.

The accumulation of amyloid-β (Aβ peptides) is believed to be one of the underlying causes of Alzheimer's disease (AD), which is the most common cause of cognitive decline in the elderly (Hardy & Allsop, Trends Pharmacol Sci., 1991; 12(10):383-8; Selkoe, Behav. Brain Res., 2008; 192 (1):106-13). Aβ, the major protein constituent of amyloid plaques, is derived from sequential cleavage of the type I integral membrane protein, amyloid precursor protein (APP) by two proteases, β- and γ-secretase. Proteolytic cleavage of APP by the β-site APP cleaving enzymes (BACE1 and BACE2) generates a soluble N-terminal ectodomain of APP (sAPPβ) and the C-terminal fragment C99. Subsequent cleavage of the membrane-bound C99 fragment by the γ-secretase liberates the various Aβ peptide species, of which Aβ40 and Aβ42 are the most predominant forms (Vassar et al., J. Neurosci., 2009; 29(41):12787-94; Marks & Berg, Neurochem. Res., 2010; 35:181-210). Therefore, limiting the generation of Aβ directly through inhibition of BACE1 is one of the most attractive approaches for the treatment of AD, as BACE1 inhibitors could effectively inhibit the formation of all predominant Aβ peptides.

In addition, it has been determined that BACE1 knock-out mice had markedly enhanced clearance of axonal and myelin debris from degenerated fibers, accelerated axonal regeneration, and earlier reinnervation of neuromuscular junctions compared with littermate controls. These data suggest BACE1 inhibition as a therapeutic approach to accelerate regeneration and recovery after peripheral nerve damage. (See Farah et al., J. Neurosci., 2011, 31(15): 5744-5754).

Insulin resistance and impaired glucose homoeostasis are important indicators of Type 2 diabetes and are early risk factors of AD. In particular, there is a higher risk of sporadic AD in patients with Type 2 diabetes and AD patients are more prone to Type 2 diabetes (Butler, Diabetes, 53:474-481, 2004.). Recently, it has also been proposed that AD should be reconsidered as Type 3 diabetes (de la Monte, J. Diabetes Sci. Technol., 2008; 2(6):1101-1113). Of special interest is the fact that AD and Type 2 diabetes share common pathogenic mechanisms and possibly treatments (Park S. A., J. Clin. Neurol., 2011; 7:10-18; Raffa, Br. J. Clin. Pharmacol 2011, 71(3):365-376). Elevated plasma levels of Aβ, the product of BACE activities, were recently associated with hyperglycemia and obesity in humans (see Meakin et al., Biochem J., 2012, 441(1):285-96; Martins, Journal of Alzheimer's Disease, 8 (2005) 269-282). Moreover, increased Aβ production prompts the onset of glucose intolerance and insulin resistance in mice (Cózar-Castellano, Am. J. Physiol. Endocrinol. Metab., 302:E1373-E1380, 2012; Delibegovic, Diabetologia (2011) 54:2143-2151). Finally, it is also suggested that circulating Aβ could participate in the development of atherosclerosis in both humans and mice (De Meyer, Atherosclerosis 216 (2011) 54-58; Catapano, Atherosclerosis 210 (2010) 78-87; Roher, Biochimica et Biophysica Acta 1812 (2011) 1508-1514).

Therefore, it is believed that BACE1 levels may play a critical role in glucose and lipid homoeostasis in conditions of chronic nutrient excess. Specifically, BACE1 inhibitors may be potentially useful for increasing insulin sensitivity in skeletal muscle and liver as illustrated by the fact that reduction in BACE1 decreases body weight, protects against diet-induced obesity and enhances insulin sensitivity in mice (see Meakin et al., Biochem. J. 2012, 441(1):285-96). Of equal interest is the identification of LRP1 as a BACE1 substrate and the potential link to atherosclerosis (Strickland, Physiol. Rev., 88: 887-918, 2008; Hyman, J. Biol. Chem., Vol. 280, No. 18, 17777-17785, 2005).

Likewise, inhibition of BACE2 is proposed as a treatment of Type 2 diabetes with the potential to preserve and restore β-cell mass and stimulate insulin secretion in pre-diabetic and diabetic patients (WO2011/020806). BACE2 is a β-cell enriched protease that regulates pancreatic β cell function and mass and is a close homologue of BACE1. Pharmacological inhibition of BACE2 increases β-cell mass and function, leading to the stabilization of Tmem27. (See Esterhazy et al., Cell Metabolism 2011, 14(3): 365-377). It is suggested that BACE2 inhibitors are useful in the treatment and/or prevention of diseases associated with the inhibition of BACE2 (e.g., Type 2 diabetes, with the potential to preserve and restore β-cell mass and stimulate insulin secretion in pre-diabetic and diabetic patients) (WO2011/020806).

Aminodihydrothiazine or thioamidine compounds are described in US2009/0082560, WO 2009/091016 and WO 2010/038686 as useful inhibitors of the β-secretase enzyme. Fused heterocyclic compounds useful as inhibitors of the β-secretase enzyme are also described in WO 2011071109 and corresponding US 2012245155. Co-pending PCT application, PCT/IB2012/054198, filed by Pfizer Inc on Aug. 17, 2012, also describes aminodihydrothiazine compounds that are useful inhibitors of the β-secretase enzyme. The present invention is directed to novel cyclic sulfonyl guanidine compounds and their use in the treatment of neurodegenerative diseases, including AD, as well as the treatment of metabolic diseases and conditions such as diabetes and obesity.

SUMMARY OF THE INVENTION

A first embodiment of a first aspect of the present invention is a compound of Formula I

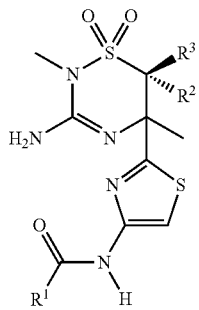

wherein $R^1$ is a 5- to 6-membered heteroaryl, having one to four heteroatoms independently selected from N, O or S, wherein at least one of the heteroatoms is N and wherein said N is optionally substituted with $R^5$; and wherein said 5- to 6-membered heteroaryl is optionally substituted on carbon with one to three $R^4$;

$R^2$ and $R^3$ are each independently hydrogen, $C_{1-6}$alkyl, $C_{3-6}$cycloalkyl or 3- to 7-membered heterocycloalkyl; wherein the $C_{1-6}$alkyl is optionally substituted with a $C_{1-3}$alkoxy or with one to three fluoro; and the $C_{3-6}$cycloalkyl and 3- to 7-membered heterocycloalkyl are each optionally and independently substituted with one to three fluoro, $C_{1-3}$alkyl or $C_{1-3}$alkoxy;

or $R^2$ and $R^3$, taken together with the carbon to which they are attached, form a $C_{3-6}$cycloalkyl ring or 3- to 7-membered heterocycloalkyl ring, each of which is optionally and independently substituted with one to three fluoro, $C_{1-3}$alkyl or $C_{1-3}$alkoxy;

$R^4$ at each occurrence is independently selected from the group consisting of halo, hydroxy, cyano, $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$alkyl, $C_{3-6}$cycloalkyl-$C_{1-6}$alkoxy, 4- to 6-membered heterocycloalkyl and 4- to 6-membered heterocycloalkyl-$C_{1-6}$alkyl; wherein said $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$alkyl, $C_{3-6}$cycloalkyl-$C_{1-6}$alkoxy, 4- to 6-membered heterocycloalkyl and 4- to 6-membered heterocycloalkyl-$C_{1-6}$alkyl are each optionally substituted with one to three substituents independently selected from fluoro, chloro, hydroxy, cyano, methyl, fluoromethyl, difluoromethyl, trifluoromethyl, methoxy, fluoromethoxy, difluoromethoxy and trifluoromethoxy; and $R^5$ is hydrogen or $C_{1-6}$alkyl optionally substituted with one to three fluoro; or a tautomer thereof or a pharmaceutically acceptable salt of said compound or tautomer.

Another embodiment of the present invention is a pharmaceutical composition comprising compounds of Formula I, or a tautomer thereof or a pharmaceutically acceptable salt of said compound or tautomer, and a pharmaceutically acceptable vehicle, diluent or carrier. The pharmaceutical compositions described herein can be used for inhibiting production of amyloid-β protein and for inhibiting beta-site amyloid precursor protein cleaving enzyme 1 (BACE1); for treating a neurodegenerative disease and, in particular, Alzheimer's disease; for inhibiting BACE1 and/or BACE2 activity for the therapeutic and/or prophylactic treatment of diseases and disorders characterized by elevated β-amyloid levels, including diabetes or Type 2 diabetes; for increasing insulin sensitivity in skeletal muscle and liver in a mammal, including humans; and for treating and/or preventing obesity.

The present invention is also directed to methods of treatment employing the compounds of Formula I such as:

(1) Methods of inhibiting BACE enzyme activity, by administering a therapeutically effective amount of a compound of any of the embodiments of Formula I or a pharmaceutically acceptable salt thereof, and a pharmaceutically acceptable carrier, to a mammal or a patient in need thereof.

(2) Methods for treating conditions or diseases of the central nervous system and neurological disorders in which the β-secretase enzyme is involved (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment ("MCI"); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS), premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema), nerve injury treatment (including accelerating regeneration and recovery after peripheral nerve damage) and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula I or pharmaceutically acceptable salt thereof. The compounds of Formula I may also be useful for improving memory (both short-term and long-term) and learning ability. The text revision of the fourth edition of the Diagnostic and Statistical Manual of Mental Disorders (DSM-IV-TR) (2000, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress;

(3) Methods for treating a neurological disorder (such as migraine; epilepsy; Alzheimer's disease; Parkinson's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof;

(4) Methods for the treatment (e.g., delaying the progression or onset) of diabetes or diabetes-related disorders including Type 1 and Type 2 diabetes, impaired glucose tolerance, insulin resistance, hyperglycemia, and diabetic complications such as atherosclerosis, coronary heart disease, stroke, peripheral vascular disease, nephropathy, hypertension, neuropathy, and retinopathy;

(5) Methods for the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on metabolic syndrome, see, e.g., Zimmet, P. Z. et al., "The Metabolic Syndrome: Perhaps an Etiologic Mystery but Far From a Myth—Where Does the International Diabetes Federation Stand?," Medscape Diabetes & Endocrinology, 7(2), (2005); and Alberti, K. G. et al., "The Metabolic Syndrome—A New Worldwide Definition," Lancet, 366, 1059-62 (2005); and (6) Methods for the treatment of nonalcoholic fatty liver disease (NAFLD) and hepatic insulin resistance;

The present invention is also directed to combination therapies wherein the compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided;

All patents, patent applications and references referred to herein are hereby incorporated by reference in their entirety.

Other features and advantages of this invention will be apparent from this specification and the appendant claims which describe the invention. It is to be understood that both the foregoing and the following detailed description are exemplary only and are not restrictive of the invention as claimed.

DETAILED DESCRIPTION OF THE INVENTION

The present invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

In this specification and in the claims that follow, reference will be made to a number of terms that shall be defined to have the following meanings:

As used herein, "eating disorders" refer to illnesses in which the patient suffers disturbances in his/her eating behaviors and related thoughts and emotions. Representative examples of obesity-related eating disorders include overeating, bulimia, binge-eating disorder, compulsive dieting, nocturnal sleep-related eating disorder, pica, Prader-Willi syndrome, and night-eating syndrome.

"Patient" refers to warm-blooded animals such as, for example, guinea pigs, mice, rats, gerbils, cats, rabbits, dogs, cattle, goats, sheep, horses, monkeys, chimpanzees, and humans.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

The term "alkyl" refers to a linear or branched-chain saturated hydrocarbyl substituent (i.e., a substituent obtained from a hydrocarbon by removal of a hydrogen); in one embodiment containing from one to six carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like.

The term "alkoxy" refers to a linear or branched-chain saturated hydrocarbyl substituent attached to an oxygen radical (i.e., a substituent obtained from a hydrocarbon alcohol by removal of the hydrogen from the OH); in one embodiment containing from one to six carbon atoms. Non-limiting examples of such substituents include methoxy, ethoxy, propoxy (including n-propoxy and isopropoxy), butoxy (including n-butoxy, isobutoxy, sec-butoxy and tert-butoxy), pentoxy, hexoxy and the like.

The term "alkenyl" refers to a linear or branched-chain hydrocarbyl substituent (i.e., a substituent obtained from a hydrocarbon by removal of a hydrogen) which contains at least one carbon-carbon double bond; in one embodiment containing from three to six carbon atoms. Non-limiting examples of such substituents include allyl, propenyl, butenyl, isobutenyl, butadienyl, pentenyl, pentadienyl, hexenyl, hexadienyl and the like. The term "alkenyloxy" refers to an alkenyl group attached to an oxygen radical.

The term "alkynyl" refers to a linear or branched-chain hydrocarbyl substituent (i.e., a substituent obtained from a hydrocarbon by removal of a hydrogen) which contains at least one carbon-carbon triple bond; in one embodiment containing from three to six carbon atoms. Non-limiting examples of such substituents include propynyl, butynyl, isobutynyl, pentynyl, hexynyl and the like. The term "alkynyloxy" refers to an alkynyl group attached to an oxygen radical.

The term "alkylene" refers to an alkanediyl group (i.e. a substituent obtained from a hydrocarbon by removal of two hydrogens); in one embodiment containing from three to five carbons. Non-limiting examples of such groups include propylene, butylene and pentylene.

In some instances, the number of carbon atoms in a hydrocarbyl substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$-alkyl" or "$C_{1-6}$ alkyl" refers to an alkyl substituent containing from 1 to 6 carbon atoms. Illustrating further, $C_3$-$C_6$cycloalkyl or $C_{3-6}$-cycloalkyl refers to saturated cycloalkyl group containing from 3 to 6 carbon ring atoms.

The term "cycloalkyl" refers to a carbocyclic substituent obtained by removing a hydrogen from a saturated carbocyclic molecule, for example one having three to six carbon atoms or having three to nine carbon atoms. The term "cycloalkyl" includes mono-, bi- and tricyclic saturated carbocycles, as well as bridged and fused ring carbocycles and also spiro-fused carbocyclic ring systems. The term "$C_{3-9}$cycloalkyl" means a radical of a three- to nine-membered ring system, which includes the groups cyclopropyl, cyclobutyl, cyclopentyl, cyclohexyl, cycloheptyl, cyclooctyl, cyclononyl, bicyclopentyl, bicyclohexyl, bicycloheptyl, bicyclooctyl, bicyclononyl, spiropentyl, spirohexyl, spiroheptyl, spirooctyl and spirononyl. The term "$C_{3-6}$cycloalkyl" means a radical of a three- to six-membered ring system, which includes the groups cyclopropyl, cyclobutyl, cyclopentyl, cyclohexyl, bicyclopentyl, bicyclohexyl, spiropentyl and spirohexyl. The term "$C_{3-6}$cycloalkoxy" refers to a three- to six-membered cycloalkyl group attached to an oxygen radical. Examples include cyclopropoxy, cyclobutoxy, cyclopentoxy and cyclohexoxy.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "4- to 6-membered heterocycloalkyl" refers to a heterocycloalkyl containing from 4 to 6 atoms, including one to three heteroatoms, in the cyclic moiety of the heterocycloalkyl. Likewise the phrase "5- to 6-membered heteroaryl" refers to a heteroaryl containing from 5 to 6 atoms, and "5- to 10-membered heteroaryl" refers to a heteroaryl containing from 5 to 10 atoms, each including one or more heteroatoms, in the cyclic moiety of the heteroaryl. Furthermore the phases "5-membered heteroaryl" and "6-membered heteroaryl" refer to a five-membered heteroaromatic ring system and a six-membered heteroaromatic ring system, respectively. The heteroatoms present in these ring systems are selected from N, O and S.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "halo" or "halogen" refers to fluorine (which may be depicted as —F), chlorine (which may be depicted as —Cl), bromine (which may be depicted as —Br), or iodine (which may be depicted as —I).

The term "heterocycloalkyl" refers to a substituent obtained by removing a hydrogen from a saturated or partially saturated ring structure containing a total of the specified number of atoms, such as 4 to 6 ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. In a group that has a heterocycloalkyl substituent, the ring atom of the heterocycloalkyl substituent that is bound to the group may be a nitrogen heteroatom, or it may be a ring carbon atom. Similarly, if the heterocycloalkyl substituent is in turn substituted with a group or substituent, the group or substituent may be bound to a nitrogen heteroatom, or it may be bound to a ring carbon atom.

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered heteroaryl substituents such as pyridyl, pyrazyl, pyrimidinyl, and pyridazinyl; and 5-membered heteroaryl substituents such as triazolyl, imidazolyl, furanyl, thiophenyl, pyrazolyl, pyrrolyl, oxazolyl, isoxazolyl, thiazolyl, 1,2,3-, 1,2,4-, 1,2,5-, or 1,3,4-oxadiazolyl and isothiazolyl. The heteroaryl group can also be a bicyclic heteroaromatic group such as indolyl, benzofuranyl, benzothienyl, benzimidazolyl, benzothiazolyl, benzoxazolyl, benzoisoxazolyl, oxazolopyridinyl, imidazopyridinyl, imidazopyrimidinyl and the like. In a group that has a heteroaryl substituent, the ring atom of the heteroaryl substituent that is bound to the group may be a ring nitrogen atom, or it may be a ring carbon atom. Similarly, if the heteroaryl substituent is in turn substituted with a group or substituent, the group or substituent may be bound to a ring nitrogen atom, or it may be bound to a ring carbon atom. The term "heteroaryl" also includes pyridyl N-oxides and groups containing a pyridine N-oxide ring. In addition, the heteroaryl group may contain an oxo group such as the one present in a pyridone group. Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, and pyrazolo[1,5-a]pyridinyl. The heteroaryl can be further substituted as defined herein.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), morpholinyl.

The term "heteroaryl" can also include, when specified as such, ring systems having two rings wherein such rings may be fused and wherein one ring is aromatic and the other ring is not fully part of the conjugated aromatic system (i.e., the heteroaromatic ring can be fused to a cycloalkyl or heterocycloalkyl ring). Non-limiting examples of such ring systems include 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

If substituents are described as "independently" having more than one variable, each instance of a substituent is selected independent of the other(s) from the list of variables available. Each substituent therefore may be identical to or different from the other substituent(s).

If substituents are described as being "independently selected" from a group, each instance of a substituent is selected independent of the other(s). Each substituent therefore may be identical to or different from the other substituent(s).

As used herein, the term "Formula I" may be hereinafter referred to as a "compound(s) of the invention," "the present invention," and "compound of Formula I." Such terms are also defined to include all forms of the compound of Formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line (-), a solid wedge (◥) or a dotted wedge (⸺) The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of Formula I may exhibit the phenomenon of tautomerism; such tautomers are also regarded as compounds of the invention. For example, the compounds of Formula I may exist in several tautomeric forms, including the 3-amino-2-methyl-5,6-dihydro-2H-1,2,4-thiadiazine 1,1-dioxide form I, and the 3-imino-2-methyl-1,2,4-thiadiazinane 1,1-dioxide form I'. All such tautomeric forms, and mixtures thereof, are included within the scope of compounds of Formula I. Tautomers exist as mixtures of a tautomeric set in solution. In solid form, usually one tautomer predominates. Even though one tautomer may be described, the present invention includes all tautomers of the compounds of Formula I and salts thereof. Examples of tautomers are described by the compounds of Formula I and I' and, collectively and generically, are referred to as compounds of Formula I.

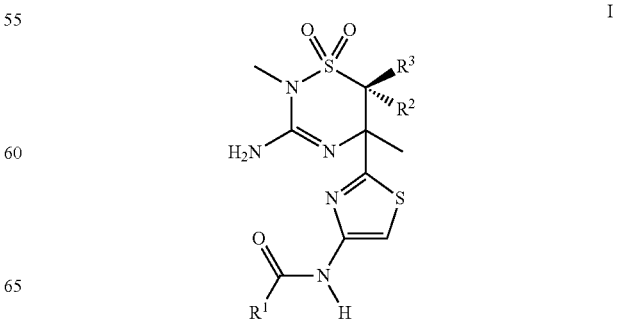

I

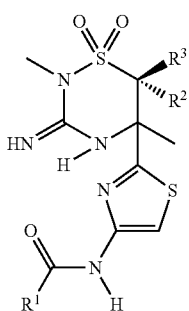

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention, when possible, include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include the lighter alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula I with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs that contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

A second embodiment of a first aspect of the present invention is the compound of the first embodiment of the first aspect of Formula Ia

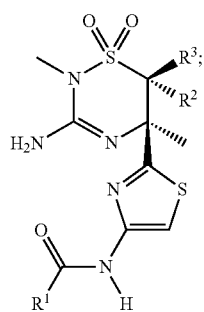

or a tautomer thereof or a pharmaceutically acceptable salt of said compound or tautomer.

A third embodiment of a first aspect of the present invention is the compound of the first embodiment of the first aspect of Formula Ib

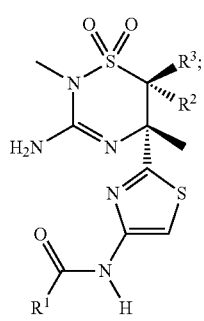

or a tautomer thereof or a pharmaceutically acceptable salt of said compound or tautomer.

A fourth embodiment of a first aspect of the present invention is the compound of any one of the first through third embodiments of the first aspect wherein $R^1$ is pyrazolyl substituted with $R^5$; or oxazolyl, pyridinyl or pyrazinyl substituted with one or two $R^4$; or a tautomer thereof or a pharmaceutically acceptable salt of said compound or tautomer.

A fifth embodiment of the first aspect of the present invention is the compound of the fourth embodiment of the first aspect wherein $R^4$ at each occurrence is independently selected from the group consisting of halo, cyano, $C_{1-3}$alkyl optionally substituted with one to three fluoro, $C_{1-3}$alkoxy optionally substituted with one to three fluoro, and $C_{3-4}$alkynyloxy; $R^5$ is $C_{1-3}$alkyl optionally substituted with one to three fluoro; or a tautomer thereof or a pharmaceutically acceptable salt of said compound or tautomer.

A sixth embodiment of a first aspect of the present invention is the compound of the fifth embodiment of the first aspect wherein $R^1$ is 1-(difluoromethyl)-1H-pyrazol-3-yl, 2-(fluoromethyl)-1,3-oxazol-4-yl, 5-(difluoromethoxy)-pyridin-2-yl, 5-(difluoromethoxy)-3-methylpyridin-2-yl, 3-chloro-5-(difluoromethoxy)pyridin-2-yl, 5-cyanopyridin-2-yl, 5-cyano-3-methylpyridin-2-yl, 3-chloro-5-cyanopyridin-2-yl, 5-(but-2-yn-1-yloxy)pyridin-2-yl, 5-(fluoromethyl)pyrazin-2-yl, 5-(difluoromethyl)pyrazin-2-yl, 5-(2,2-difluoropropoxy)pyrazin-2-yl or 5-(but-2-yn-1-yloxy) pyrazin-2-yl; or a tautomer thereof or a pharmaceutically acceptable salt of said compound or tautomer.

A seventh embodiment of a first aspect of the present invention is the compound of the sixth embodiment of the first aspect wherein $R^2$ and $R^3$ are each hydrogen; or a tautomer thereof or a pharmaceutically acceptable salt of said compound or tautomer.

An eighth embodiment of a first aspect of the present invention is the compound of the sixth embodiment wherein $R^2$ and $R^3$ are each methyl; or a tautomer thereof or a pharmaceutically acceptable salt of said compound or tautomer.

A ninth embodiment of a first aspect of the present invention is the compound of the sixth embodiment of the first aspect wherein one of $R^2$ and $R^3$ is hydrogen and the other is methyl, ethyl, cyclopropyl, 1-methylcyclopropyl or 2,2-dimethylcyclopropyl; or a tautomer thereof or a pharmaceutically acceptable salt of said compound or tautomer.

A tenth embodiment of a first aspect of the present invention is the compound of the sixth embodiment of the first aspect wherein $R^2$ and $R^3$, taken together with the carbon to which they are attached, form a cyclopropyl, cyclobutyl or cyclopentyl ring; or a tautomer thereof or a pharmaceutically acceptable salt of said compound or tautomer.

An eleventh embodiment of a first aspect of the present invention is the compound of any one of the first through third embodiments of the first embodiment wherein $R^2$ and $R^3$ are each hydrogen; or a tautomer thereof or a pharmaceutically acceptable salt of said compound or tautomer.

A twelfth embodiment of a first aspect of the present invention is the compound of any one of the first through third embodiments of the first aspect wherein $R^2$ and $R^3$ are each methyl; or a tautomer thereof or a pharmaceutically acceptable salt of said compound or tautomer.

A thirteenth embodiment of a first aspect of the present invention is the compound of any one of the first through third embodiments of the first aspect wherein one of $R^2$ and $R^3$ is hydrogen and the other is methyl, ethyl, cyclopropyl, 1-methylcyclopropyl or 2,2-dimethylcyclopropyl; or a tautomer thereof or a pharmaceutically acceptable salt of said compound or tautomer.

A fourteenth embodiment of a first aspect of the present invention is the compound of any one of the first through third embodiments of the first aspect wherein $R^2$ and $R^3$, taken together with the carbon to which they are attached, form a cyclopropyl, cyclobutyl or cyclopentyl ring; or a tautomer thereof or a pharmaceutically acceptable salt of said compound or tautomer.

A fifteenth embodiment of a first aspect of the present invention is the compound of the first embodiment of the first aspect selected from the group consisting of N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-1-(difluoromethyl)-1H-pyrazole-3-carboxamide;

N-{2-[(5R,6S)-3-amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S,6R)-3-amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S,6S)-3-amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-[2-(3-amino-2,5,6,6-tetramethyl-1,1-dioxido-5,6-dihydro-2H-1,2,4-thiadiazin-5-yl)-1,3-thiazol-4-yl]-5-(difluoromethoxy)pyridine-2-carboxamide;

N-{2-[(5R)-3-amino-2,5,6,6-tetramethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S)-3-amino-2,5,6,6-tetramethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)-3-methylpyridine-2-carboxamide;

N-{2-[(5R,6S)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S,6R)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S,6S)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5R,6R)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5R,6S)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S,6R)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5R,6R)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S,6S)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-(difluoromethyl)pyrazine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-chloropyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-2-(fluoromethyl)-1,3-oxazole-4-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-(2,2-difluoropropoxy)pyrazine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-(but-2-yn-1-yloxy)pyrazine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-(but-2-yn-1-yloxy)pyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-3-chloro-5-(difluoromethoxy)pyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-cyanopyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-cyano-3-methylpyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-3-chloro-5-cyanopyridine-2-carboxamide;

or a tautomer thereof or a pharmaceutically acceptable salt of said compound or tautomer.

A sixteenth embodiment of a first aspect of the present invention is the compound N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide; or a tautomer thereof or a pharmaceutically acceptable salt of said compound or tautomer.

A seventeenth embodiment of a first aspect of the present invention is the compound N-{2-[(5S,6S)-3-amino-6-cyclopropyl-2,5-dimethyl-1,1-dioxido-5,6-dihydro)pyridine-2-carboxamide; or a tautomer thereof or a pharmaceutically acceptable salt of said compound or tautomer.

An eighteenth embodiment of a first aspect of the present invention is the compound N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)-3-methylpyridine-2-carboxamide; or a tautomer thereof or a pharmaceutically acceptable salt of said compound or tautomer.

A first embodiment of a second aspect of the present invention is a pharmaceutical composition comprising a therapeutically effective amount of a compound according to any one of the first through eighteenth embodiments of the first aspect, or a tautomer thereof or a pharmaceutically acceptable salt of said compound or tautomer together with a pharmaceutically acceptable carrier.

Further embodiments of the present invention include methods of treatment employing the compounds of the present invention.

A first embodiment of a third aspect of the present invention is a method of inhibiting production of amyloid-β protein in a patient, the method comprising administering a therapeutically effective amount of a compound according to any one of the first through eighteenth embodiments of the first aspect, or a tautomer thereof or a pharmaceutically acceptable salt of said compound or tautomer, to a patient in need of inhibition of production of amyloid-β protein.

A second embodiment of a third aspect of the present invention is a method of inhibiting beta-site amyloid precursor protein cleaving enzyme 1 (BACE1) in a patient, the method comprising administering a therapeutically effective amount of a compound according to any one of the first through eighteenth embodiments of the first aspect, or a tautomer thereof or a pharmaceutically acceptable salt of said compound or tautomer, to a patient in need of inhibition of beta-site amyloid precursor protein cleaving enzyme 1 (BACE1).

A third embodiment of a third aspect of the present invention is a method for treating a neurodegenerative disease in a patient, the method comprising administering a therapeutically effective amount of a compound according to any one of the first through eighteenth embodiments of the first aspect, or a tautomer thereof or a pharmaceutically acceptable salt of said compound or tautomer, to a patient in need of treatment thereof.

A fourth embodiment of a third aspect of the present invention is the method of the third embodiment of the third aspect wherein the neurodegenerative disease is Alzheimer's disease.

A fifth embodiment of a third aspect of the present invention is a method of treating or preventing diabetes in a patient, the method comprising administering a therapeutically effective amount of a compound according to any one of the first through eighteenth embodiments of the first aspect, or a tautomer thereof or a pharmaceutically acceptable salt of said compound or tautomer, to a patient in need of treatment or prevention thereof.

A sixth embodiment of a third aspect of the present invention is the method of the fifth embodiment of the third aspect wherein the diabetes is Type 2 diabetes.

Further embodiments of the present invention include the use of a compound according to any one of first through eighteenth embodiments of the first aspect of the present invention in the preparation of a medicament useful for treating the conditions, diseases and disorders as described herein.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a BACE inhibitor compound as provided in Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include, without limitation:

(i) anti-obesity agents (including appetite suppressants), include gut-selective MTP inhibitors (e.g., dirlotapide, mitratapide and implitapide, CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonists (e.g., compounds described in U.S. Pat. No. 6,818,658), lipase inhibitors (e.g., Cetilistat), $PYY_{3-36}$ (as used herein "$PYY_{3-36}$" includes analogs, such as peglated $PYY_{3-36}$, e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine.

(ii) anti-diabetic agents, such as an acetyl-CoA carboxylase (ACC) inhibitor as described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, a diacylglycerol O-acyltransferase 2 (DGAT-2) inhibitor, a monoacylglycerol O-acyltransferase inhibitor, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPAR γ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S. et al., Drug Discovery Today, 12(9/10), 373-381 (2007)), a SIRT-1 inhibitor (e.g., resveratrol, GSK2245840 or GSK184072), a dipeptidyl peptidase IV (DPP-IV) inhibitor (e.g., those in WO2005116014, sitagliptin, vildagliptin, alogliptin, dutogliptin, linagliptin and saxagliptin), an insulin secretagogue, a fatty acid oxidation inhibitor, an A2 antagonist, a c-jun amino-terminal kinase (JNK) inhibitor, a glucokinase activator (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g., GSK1362885), a VPAC2 receptor agonist, an SGLT2 inhibitor, such as those described in E. C. Chao et al., Nature Reviews Drug Discovery 9, 551-559 (July 2010) including dapagliflozin, canagliflozin, BI-10733, tofogliflozin (CSG452), ASP-1941, THR1474, TS-071, ISIS388626 and LX4211 as well as those in WO2010023594, a glucagon receptor modulator such as those described in Demong, D. E. et al., Annual Reports in Medicinal Chemistry 2008, 43, 119-137, a GPR119 modulator, particularly an agonist, such as those described in WO2010140092, WO2010128425, WO2010128414, WO2010106457, Jones, R. M. et al., in Medicinal Chemistry 2009, 44, 149-170 (e.g., MBX-2982, GSK1292263, APD597 and PSN821), an FGF21 derivative or an analog such as those described in Kharitonenkov, A. et al., Current Opinion in Investigational Drugs 2009, 10(4), 359-364, TGR5 (also termed GPBAR1) receptor modulators, particularly agonists, such as those described in Zhong, M., Current Topics in Medicinal Chemistry, 2010, 10(4), 386-396 and INT777, a GPR40 agonist, such as those described in Medina, J. C., Annual Reports in Medicinal Chemistry, 2008, 43, 75-85, including but not limited to TAK-875, a GPR120 modulator, particularly an agonist, a high-affinity nicotinic acid receptor (HM74A) activator, and an SGLT1 inhibitor, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g., PKCa, PKCb, PKCg), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g., SSTR1, SSTR2, SSTR3 and SSTR5), inhibitors or modulators of PDHK2 or PDHK4, inhibitors of MAP4K4, modulators of IL1 family including IL1 beta, and modulators of RXRalpha. In addition, suitable anti-diabetic agents include mechanisms listed by Carpino, P. A., Goodwin, B. Expert Opin. Ther. Pat, 2010, 20(12), 1627-51;

(iii) anti-hyperglycemic agents, for example, those described at page 31, line 31 through page 32, line 18 of WO 2011005611;

(iv) lipid lowering agents (for example, those described at page 30, line 20 through page 31, line 30 of WO 2011005611), and anti-hypertensive agents (for example, those described at page 31, line 31 through page 32, line 18 of WO 2011005611);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALIN®), tacrine (COGNEX®), tolserine, memoquin, huperzine A (HUP-A; Neuro-Hitech), phenserine, bisnorcymserine (also known as BNC), and INM-176;

(vi) amyloid-β (or fragments thereof), such as $Aβ_{1-15}$ conjugated to pan HLA DR-binding epitope (PADRE®), ACC-001 (Elan/Wyeth), and Affitope;

(vii) antibodies to amyloid-β (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(viii) amyloid-lowering or -inhibiting agents (including those that reduce amyloid production, accumulation and fibrillization) such as eprodisate (KIACTA®), celecoxib, lovastatin, anapsos, colostrinin, pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulin-degrading enzyme (also known as insulysin), the gingko *biloba* extract EGb-761 (ROKAN®, TEBONIN®), tramiprosate (CEREBRIL®, ALZHEMED®), neprilysin (also known as neutral endopeptidase (NEP)), scyllo-inositol (also known as scyllitol), atorvastatin (LIPITOR®), simvastatin (ZOCOR®), ibutamoren mesylate, BACE inhibitors such as LY450139 (Lilly), BMS-782450, and GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(ix) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors; central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) monoamine oxidase (MAO) inhibitors, such as selegiline (EMSAM), selegiline hydrochloride (I-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xiii) phosphodiesterase (PDE) inhibitors, including (a) PDE1 inhibitors (b) PDE2 inhibitors (c) PDE3 inhibitors (d) PDE4 inhibitors (e) PDE5 inhibitors (f) PDE9 inhibitors (e.g., PF-04447943, BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), and (g) PDE10 inhibitors such as 2-({4-[1-methyl-4-(pyridin-4-yl)-1H-pyrazol-3-yl]phenoxy}methyl)quinoline (PF-2545920);

(xiv) serotonin (5-hydroxytryptamine) 1A (5-$HT_{1A}$) receptor antagonists, such as spiperone, levo-pindolol, lecozotan;

(xv) serotonin (5-hydroxytryptamine) 2C (5-$HT_{2C}$) receptor agonists, such as vabicaserin, and zicronapine; serotonin (5-hydroxytryptamine) 4 (5-$HT_4$) receptor agonists/antagonists, such as PRX-03140 (Epix) and PF-04995274;

(xvi) serotonin (5-hydroxytryptamine) 3C (5-$HT_{3C}$) receptor antagonists, such as Ondansetron (Zofran);

(xvii) serotonin (5-hydroxytryptamine) 6 (5-$HT_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck A/S), SAM-760, and PRX-07034 (Epix);

(xviii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xix) Glycine transporter-1 inhibitors such as paliflutine, ORG-25935, and ORG-26041; and mGluR modulators such as AFQ-059 and amantidine;

(xx) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;

(xxi) P450 inhibitors, such as ritonavir;

(xxii) tau therapy targets, such as davunetide;

and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

General Synthetic Schemes

The compounds of Formula I may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. Additionally, one skilled in the art will recognize that in many cases, these compounds will be mixtures and enantiomers that may be separated at various stages of the synthetic schemes using conventional techniques, such as, but not limited to, crystallization, normal-phase chromatography, reversed phase chromatography and chiral chromatography, to afford single enantiomers. The schemes are representative of methods useful in synthesizing the compounds of the present invention. They are not to constrain the scope of the invention in any way.

Scheme 1 refers to the preparation of compounds of Formula I, Ia and Ib. Referring to Scheme 1, the compound of Formula III, III' or III" can be prepared from the compound of Formula II, II' or II" via a standard peptide coupling with a carboxylic acid and a suitable coupling reagent, for example, but not limited to, O-(7-azabenzotriazol-1-yl)-N,N,N',N'-tetramethyluronium hexafluorophosphate (HATU) or 2,4,6-tripropyl-1,3,5,2,4,6-trioxatriphosphinane 2,4,6-trioxide in ethyl acetate (T3P). A compound of Formula I, Ia or Ib can then be prepared through removal of protecting group $P^1$. $P^1$ in this case refers to groups well known to those skilled in the art for amine protection. For example, $P^1$ may be a benzoyl group (Bz), which can be cleaved via basic conditions, including but not limited to treatment with 1,8-diazabicyclo[5.4.0]undec-7-ene (DBU) in methanol. Alternatively $P^1$ may be one of many other protecting groups suitable for amines, including 9-fluorenylmethoxycarbonyl (Fmoc) or tert-butoxy carbonyl (BOC) and can be cleaved under standard conditions known in the art.

Scheme 1

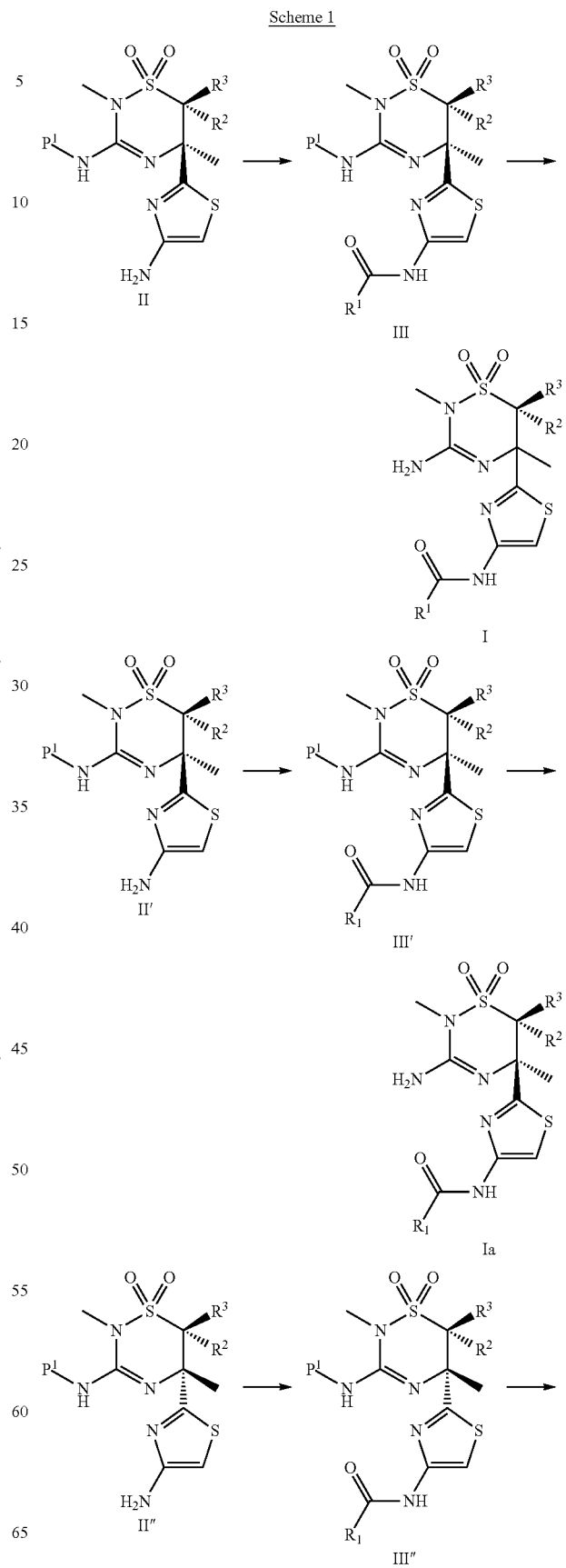

-continued

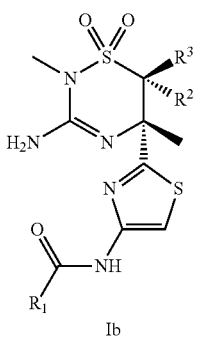

Ib

Scheme 2 refers to the preparation of compounds II' wherein P[1] is Bz or Boc. Sulfinimines of Formula V are transformed to adducts of Formula VI via the addition of an appropriately metallated sulfonamide IV (generated, for example, through treatment with n-butyllithium). Sulfonamides of Formula VII are prepared through the deprotection of compound VI with a appropriate agent, such as, but not limited to, trifluoroacetic acid in 1,3-dimethoxybenzene. Compounds of Formula IX are then prepared via treatment with the appropriate isothiocyanate (such as benzoyl isothiocyanate), and subsequent ring closure of VIII using an appropriate alkylating agent such as methyl iodide with a base such as potassium carbonate. Conversion of the bromothiazole of Formula IX to the corresponding amine can be effected via a transition metal-catalyzed coupling reaction, such as a palladium-mediated amination. An example includes using a protected ammonia source, such as, but not limited to 1-(2,4-dimethoxyphenyl)methanamine and a suitable catalyst and ligand choice, for example, tris(dibenzylideneacetone)dipalladium(0) and di-tert-butyl[2',4',6'-tri(propan-2-yl)biphenyl-2-yl]phosphane or biphenyl-2-yl(di-tert-butyl)phosphane (John Phos). Alternatively, one can utilize a copper-mediated azide coupling method. One skilled in the art will recognize that the requisite protected ammonia source will need to be deprotected to afford compounds of Formula II'. In the example utilizing 1-(2,4-dimethoxyphenyl)methanamine, said deprotection can be effected via acidic hydrolysis, such as treatment with concentrated hydrochloric acid. Compound II' can be converted into a compound of Formula Ia according to the methods of Scheme 1. It is to be understood by one skilled in the art that the compounds of Formula I and Ib can be prepared in an analogous manner.

Scheme 2

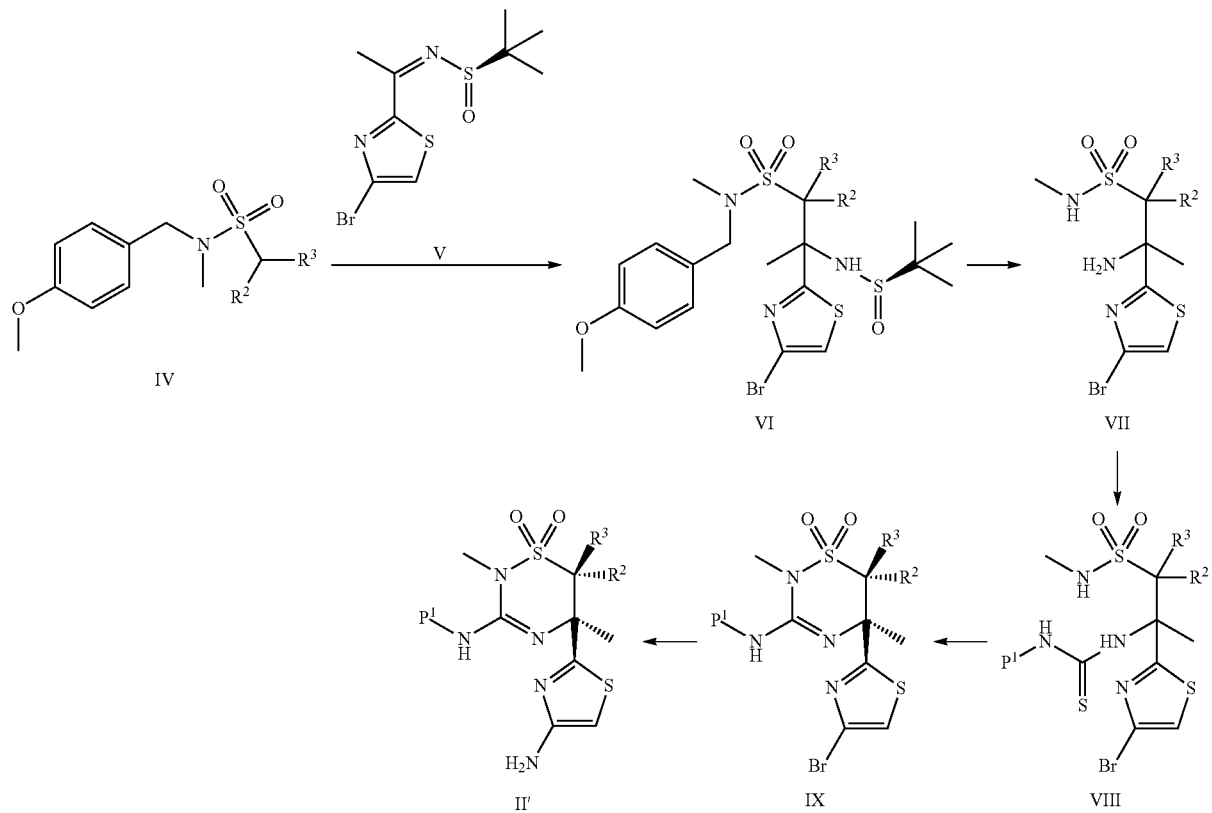

Scheme 3 refers to the preparation of compounds IX. The alkylation of compounds of Formula X may be accomplished in a variety of ways known to those skilled in the art. As an example, compounds of the Formula X may be treated with a suitable strong base including but not limited to lithium bis(trimethylsilyl)amide or sodium bis(trimethylsilyl)amide, followed by treatment with an alkylating agent such as but not limited to methyl, ethyl or other alkyl iodides. Additionally, the stereochemistry of the initial product may alternatively be adjusted by further treatment with base followed by protonation with an agent such as water or aqueous ammonium chloride. Additional bases that have utility include lithium diisopropylamide or potassium tert-butoxide. Alternatively, the introduction of a group such as $R^2$ or $R^3$ wherein one of $R^2$ and $R^3$ is hydrogen may be initiated by a suitable olefination of X using a suitable base as described above and a reagent such as dimethylmethylideneammonium iodide (Eschenmoser's salt). The resulting dimethylamine adduct may be eliminated directly with base or may be treated with methyl iodide or an oxidizing agent such as perbenzoic acid or tert-butyl hydroperoxide and subjected to treatment with a base such as described above, with the formation of a methylene group. The resulting exo-olefin may be reduced by catalytic hydrogenation over a catalyst consisting of supported or unsupported palladium, nickel or platinum. Alternatively, the exo-olefin group may be reduced through conjugate hydride addition with, for instance, lithium tri-sec-butylborohydride or lithium aluminum hydride, followed by protonation of the resulting anion as described above. A compound of Formula IX can be then be transformed into a compound of Formula II' according to the methods described above for Scheme 2. It will be understood by one skilled in the art that the compounds of Formula II or II" can be prepared in an analogous manner.

Scheme 3

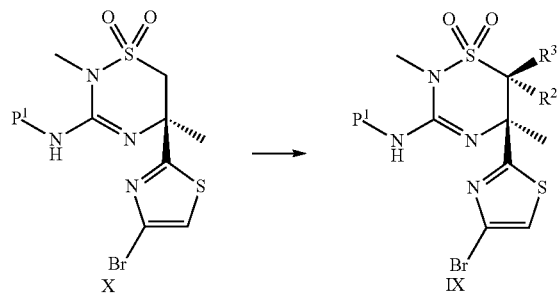

The following are abbreviations which may be used in the description of the experimental section:
AlMe$_3$=trimethylaluminum; br=broad; Bu$_4$NNO$_3$=tetrabutylammonium nitrate; CaCl$_2$=calcium chloride; CDCl$_3$=deutero-chloroform; CD$_3$OD=deutero-methanol; (CF$_3$CO$_2$)O=trifluoroacetic anhydride; d=doublet, dd=doublet of doublets; DBU=1,8-diazabicyclo[5.4.0] undec-7-ene; DCM=dichloromethane; DMF=N,N-dimethylformamide; EDC or EDCI=1-ethyl-3-(3-dimethylaminopropyl)carbodiimide hydrochloride; EtOAc=ethyl acetate; EtOH=ethanol; Fe=iron; g=gram; h=hour; HATU=O-(7-azabenzotriazol-1-yl)-N,N,N',N'-tetramethyluronium hexafluorophosphate; HCl=hydrochloric acid; H$_2$O=water; HPLC=high performance liquid chromatography; Hz=hertz; K$_2$CO$_3$=potassium carbonate; L=liter; LCMS=liquid chromatography mass spectroscopy; LiOH=lithium hydroxide; m=multiplet; M=molar; MeI=methyl iodide; MeOH=methanol; mg=milligram; MHz=megahertz; min=minute; μL=microliter; mL=milliliter, μmol=micromole; mmol=millimole; mol=mole; N=normal; NaH=sodium hydride; n-BuLi=n-butyllithium; NEt$_3$=triethylamine; NH$_4$Cl=ammonium chloride; NaHCO$_3$=sodium bicarbonate; NaOAc=sodium acetate; NaOCl=sodium hypochlorite; NaOH=sodium hydroxide; NaOMe=sodium methoxide; NaOtBu=sodium tert-butoxide; Na$_2$SO$_4$=sodium sulfate; NH$_2$OH·HCl=hydroxylamine hydrochloride; NMR=nuclear magnetic resonance; NOE=Nuclear Overhauser effect; Pd$_2$(dba)$_3$=tris(dibenzylideneacetone)dipalladium(0); Pd(dppf)Cl$_2$=[1,1'-bis(diphenylphosphino) ferrocene]dichloropalladium(II); PPh$_3$=triphenylphosphine; q=quartet; rt=room temperature; s=singlet; t=triplet; TBAF=tetrabutylammonium fluoride; t-BuylXPhos=di-tert-butyl[2',4',6'-tri(propan-2-yl)biphenyl-2-yl]phosphane; TFA or CF$_3$CO$_2$H=trifluoroacetic acid; THF=tetrahydrofuran; TLC=thin layer chromatography; Zn(CN)$_2$=zinc cyanide.

Experimental Procedures

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times. All starting materials in these Preparations and Examples are either commercially available or can be prepared by methods known in the art or as described herein.

Preparation P1
tert-Butyl [(5S)-5-(4-amino-1,3-thiazol-2-yl)-2,5-dimethyl-1,1-dioxido-5,6-dihydro-2H-1,2,4-thiadiazin-3-yl]carbamate (P1)
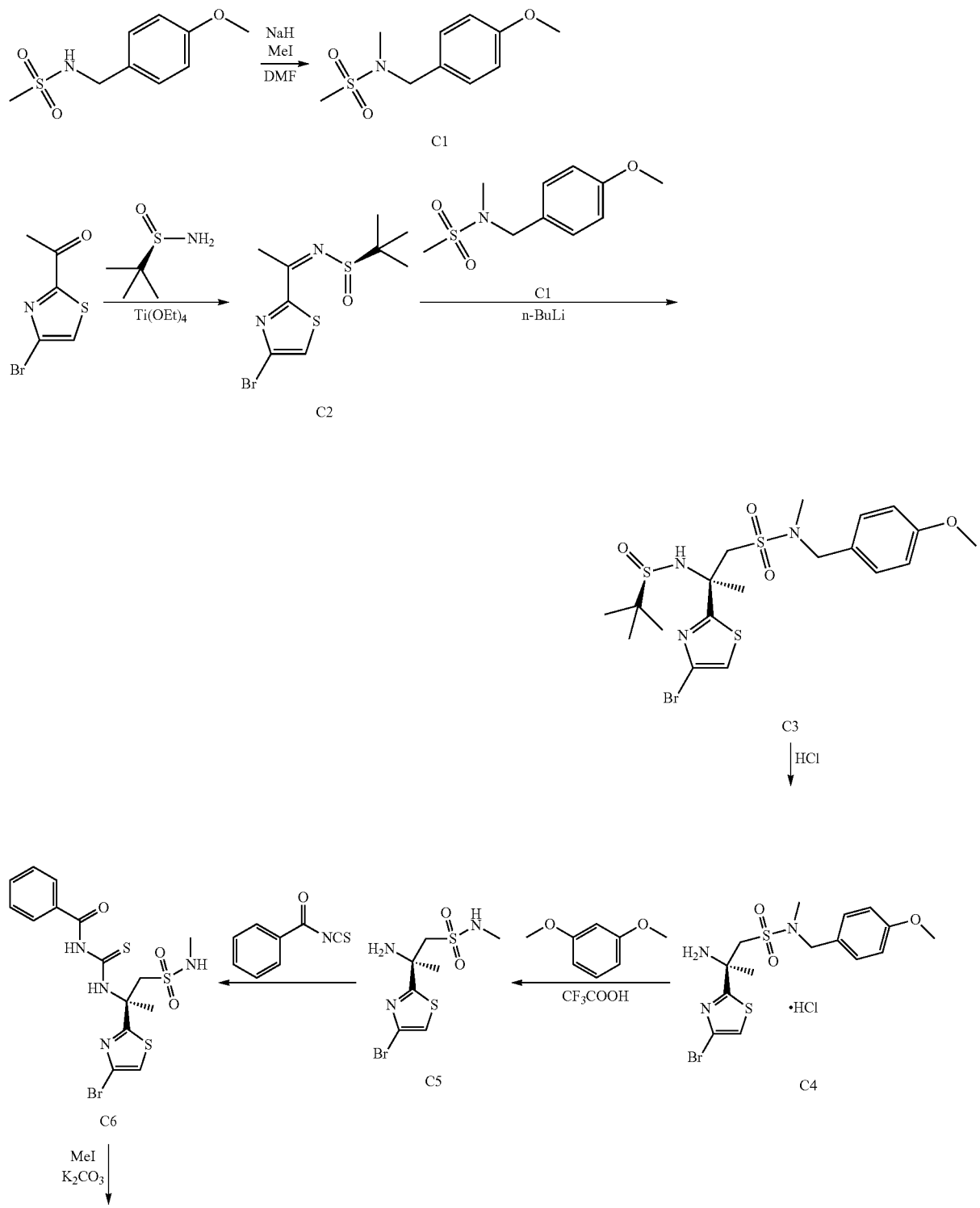

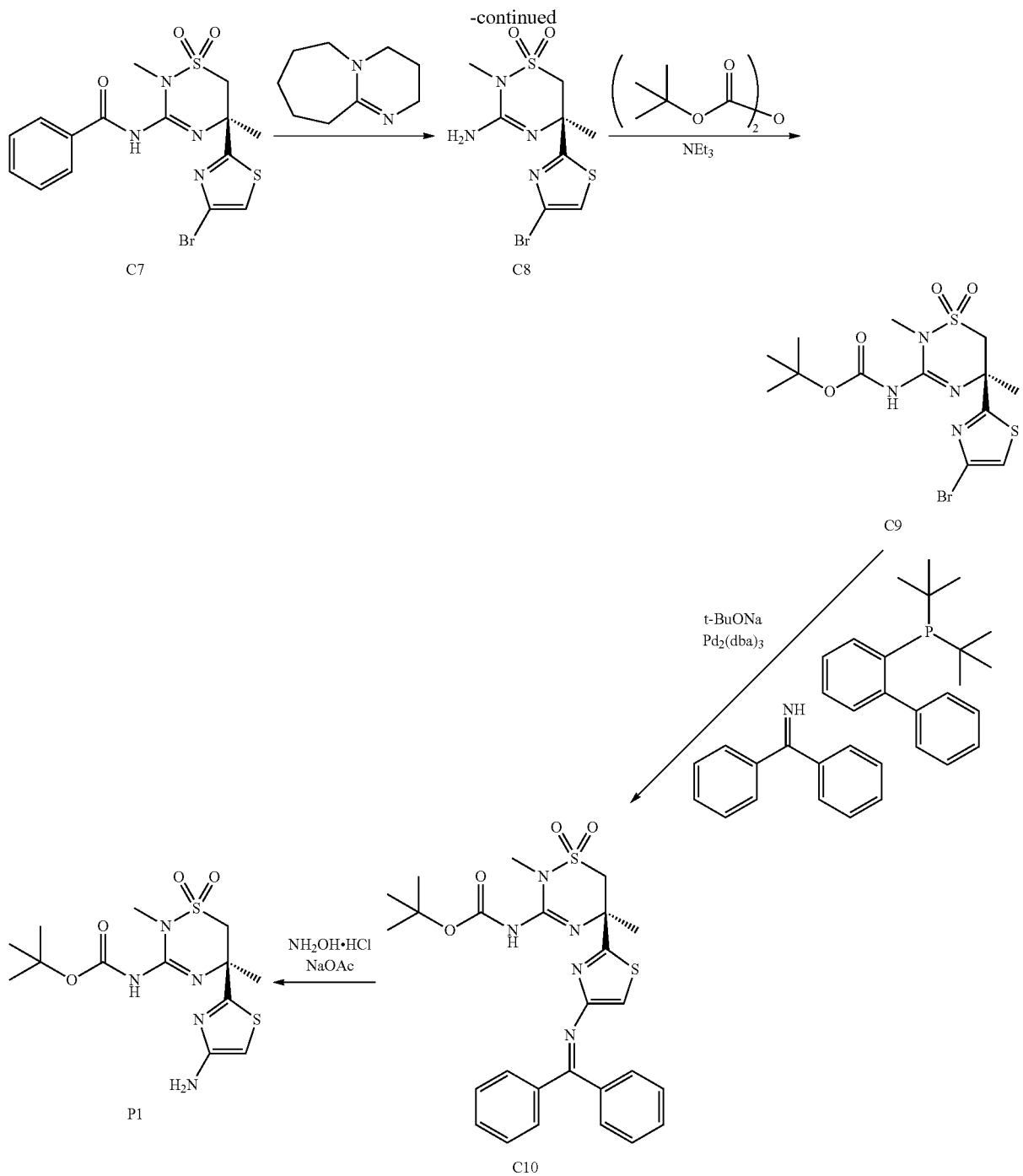

Step 1. Synthesis of N-(4-methoxybenzyl)-N-methylmethanesulfonamide (C1)

This experiment was carried out in two identical batches. Sodium hydride (60% in mineral oil, 53.3 g, 1.33 mol) was added in portions to a 0° C. solution of N-(4-methoxybenzyl)methanesulfonamide (205 g, 952 mmol) in tetrahydrofuran (2.5 L), and the reaction mixture was stirred at 0° C. for 30 minutes. Iodomethane (245 g, 1.73 mol) was then added drop-wise over 30 minutes at 0° C., whereupon the reaction mixture was stirred at room temperature (~18° C.) for 1 hour, then poured into ice water (2 L). The resulting mixture was extracted with ethyl acetate (3×1 L), and the combined organic layers were washed with saturated aqueous sodium chloride solution (3×1 L), dried over sodium sulfate, filtered, and concentrated in vacuo. The two batches of crude product were combined, diluted with petroleum ether (2 L) and stirred at room temperature (~20° C.) for 30 minutes; the resulting solid was isolated via filtration to afford the product as a yellow solid. Yield: 392 g, 1.71 mol, 90%. $^1$H NMR (400 MHz, CDCl$_3$) δ 7.28 (br d, J=8.5 Hz, 2H), 6.90 (br d, J=8.5 Hz, 2H), 4.26 (s, 2H), 3.82 (s, 3H), 2.81 (s, 3H), 2.76 (s, 3H).

Step 2. Synthesis of N-[1-(4-bromo-1,3-thiazol-2-yl)ethylidene]-(R)-2-methylpropane-2-sulfinamide (C2)

This experiment was carried out in two identical batches. Titanium(IV) ethoxide (321 g, 1.41 mol) was added in one portion to a room temperature (~15° C.) solution of 1-(4-bromo-1,3-thiazol-2-yl)ethanone (145 g, 704 mmol) and (R)-2-methylpropane-2-sulfinamide (128 g, 1.06 mol) in tetrahydrofuran (2.0 L), and the reaction mixture was heated at 75° C. for 16 hours. It was then cooled to room temperature (~15° C.), quenched with water (500 mL), and filtered. The filter cake was washed with ethyl acetate (4×500 mL), and the combined filtrates were concentrated in vacuo. The residues from the two batches were combined and purified via silica gel chromatography (Gradient: 5% to 25% ethyl acetate in petroleum ether), providing the product as a yellow solid. Yield: 340 g, 1.10 mol, 78%. $^1$H NMR (400 MHz, CDCl$_3$) δ 7.42 (s, 1H), 2.85 (s, 3H), 1.32 (s, 9H).

Step 3. Synthesis of (2S)-2-(4-bromo-1,3-thiazol-2-yl)-2-{[(R)-tert-butylsulfinyl]amino}-N-(4-methoxybenzyl)-N-methylpropane-1-sulfonamide (C3)

This experiment was carried out in two identical batches. n-Butyllithium (2.5 M solution in hexanes, 165 mL, 412 mmol) was added in a drop-wise manner over 1 hour to a −70° C. solution of C1 (98.0 g, 427 mmol) in tetrahydrofuran (1.5 L). After the reaction mixture had stirred at −70° C. for 1 hour, a solution of C2 (85 g, 275 mmol) in tetrahydrofuran (600 mL) was added drop-wise over 30 minutes, and stirring was then continued at −70° C. for 1 hour. Saturated aqueous ammonium chloride solution (1.0 L) was added at −70° C.; the aqueous layer was extracted with ethyl acetate (2×1 L), and the combined organic layers were dried over sodium sulfate, filtered, and concentrated in vacuo. The two reaction products were combined and purified via silica gel chromatography (Gradient: 10% to 80% ethyl acetate in petroleum ether) to afford a white solid (145 g). This material was treated with tert-butyl methyl ether (1.4 L) and stirred at room temperature (~15° C.) for 2 hours, whereupon the solid was collected via filtration to afford the product as a white solid. The indicated absolute stereochemistry is that expected from this transformation (see J. A. Ellman et al., *Chem. Rev.* 2010, 110, 3600-3740); single-crystal X-ray structural analysis on 9 (see below), which was synthesized from P1, confirmed this absolute stereochemistry. Yield: 135 g, 251 mmol, 46%. $^1$H NMR (400 MHz, CDCl$_3$) δ 7.21 (br d, J=8.5 Hz, 2H), 7.20 (s, 1H), 6.86 (br d, J=8.5 Hz, 2H), 6.32 (s, 1H), 4.06 (AB quartet, J$_{AB}$=14.6 Hz, Δν$_{AB}$=66.7 Hz, 2H), 4.00 (d, J=13.6 Hz, 1H), 3.80 (s, 3H), 3.70 (d, J=14.0 Hz, 1H), 2.61 (s, 3H), 1.97 (s, 3H), 1.36 (s, 9H).

Step 4. Synthesis of (2S)-2-amino-2-(4-bromo-1,3-thiazol-2-yl)-N-(4-methoxybenzyl)-N-methylpropane-1-sulfonamide, hydrochloride salt (C4)

A solution of hydrogen chloride in 1,4-dioxane (4 M, 400 mL, 1.6 mol) was added drop-wise to a solution of C3 (175 g, 325 mmol) in dichloromethane (1.2 L) and methanol (600 mL) at room temperature (~13° C.), and the reaction mixture was stirred at room temperature (~13° C.) for 2 hours. Removal of solvents in vacuo afforded the product (180 g) as a colorless oil, which was used in the next step without further purification. LCMS m/z 457.8 [M+Na$^+$] (bromine isotope pattern observed).

Step 5. Synthesis of (2S)-2-amino-2-(4-bromo-1,3-thiazol-2-yl)-N-methylpropane-1-sulfonamide (C5)

To a solution of C4 (from the previous step, 180 g, ≤325 mmol) in chloroform (1.2 L) were added trifluoroacetic acid (900 mL) and 1,3-dimethoxybenzene (400 g, 2.89 mol) at room temperature (~13° C.). The reaction mixture was stirred at room temperature (−13° C.) for 16 hours, whereupon it was concentrated in vacuo and diluted with aqueous hydrochloric acid (1 M, 1.0 L). The resulting mixture was washed with tert-butyl methyl ether (2×800 mL), and the aqueous layer was basified to pH 8 with saturated aqueous sodium bicarbonate solution, then extracted with ethyl acetate (3×600 mL). The combined ethyl acetate layers were washed with saturated aqueous sodium chloride solution (500 mL), dried over sodium sulfate, filtered, and concentrated under reduced pressure to afford a yellow oil. This material was combined with the corresponding product obtained from a similar two-step reaction sequence carried out on C3 (125 g, 232 mmol) to provide the product as a yellow oil. Yield: 174 g, 554 mmol, 99% over 2 steps. LCMS m/z 313.6, 315.6 [M+H]$^+$. $^1$H NMR (400 MHz, CDCl$_3$) δ 7.20 (s, 1H), 3.94 (d, J=14.6 Hz, 1H), 3.94-3.86 (m, 1H), 3.42 (d, J=14.6 Hz, 1H), 2.72 (d, J=5.0 Hz, 3H), 2.58-2.42 (br s, 2H), 1.66 (s, 3H).

Step 6. Synthesis of N-{[(2S)-2-(4-bromo-1,3-thiazol-2-yl)-1-(methylsulfamoyl)propan-2-yl]carbamothioyl}benzamide (C6)

This experiment was carried out in two identical batches. Benzoyl isothiocyanate (63.9 g, 392 mmol) was added in one portion to a room temperature (~13° C.) solution of C5 (82 g, 261 mmol) in dichloromethane (1.8 L). The reaction mixture was stirred at room temperature (~13° C.) for 16 hours, whereupon it was concentrated in vacuo and the two batches were combined. Chromatography on silica gel (Gradient: 10% to 80% ethyl acetate in petroleum ether) afforded the product as an off-white foam. Yield: 226 g, 473 mmol, 91%. LCMS m/z 478.7 [M+H]$^+$ (bromine isotope pattern observed). $^1$H NMR (400 MHz, CDCl$_3$) δ 11.64 (s, 1H), 9.00 (s, 1H), 7.87 (br d, J=8 Hz, 2H), 7.65 (br t, J=7.4 Hz, 1H), 7.53 (br dd, J=8.0, 7.5 Hz, 2H), 7.26 (s, 1H), 5.18 (d, J=14.8 Hz, 1H), 4.59 (br q, J=5 Hz, 1H), 4.13 (d, J=14.6 Hz, 1H), 2.86 (d, J=5.3 Hz, 3H), 2.13 (s, 3H).

Step 7. Synthesis of N-[(5S)-5-(4-bromo-1,3-thiazol-2-yl)-2,5-dimethyl-1,1-dioxido-5,6-dihydro-2H-1,2,4-thiadiazin-3-yl]benzamide (C7)

Iodomethane (61.5 g, 433 mmol) was added drop-wise to a room temperature (~13° C.) mixture of C6 (110 g, 230 mmol) and potassium carbonate (63.7 g, 461 mmol) in acetonitrile (1.5 L). The reaction mixture was stirred at room temperature (~13° C.) for 16 hours, whereupon it was diluted with saturated aqueous ammonium chloride solution (1.0 L) and extracted with ethyl acetate (3×800 mL). The combined organic layers were washed with saturated aqueous sodium chloride solution (800 mL), dried over sodium sulfate, filtered, and concentrated in vacuo to a volume of approximately 200 mL. After addition of petroleum ether (1.0 L), the mixture was stirred at room temperature (~13° C.) for 30 minutes, whereupon the precipitate was collected via filtration to afford the product as a white solid. Yield: 94 g, 210 mmol, 91%. $^1$H NMR (400 MHz, CDCl$_3$) δ 12.44 (s, 1H), 8.27-8.22 (m, 2H), 7.59-7.53 (m, 1H), 7.46 (br dd, J=7.8, 7.3 Hz, 2H), 7.22 (s, 1H), 4.49 (d, J=13.8 Hz, 1H), 3.72 (d, J=13.8 Hz, 1H), 3.47 (s, 3H), 1.99 (s, 3H).

Step 8. Synthesis of (5S)-5-(4-bromo-1,3-thiazol-2-yl)-2,5-dimethyl-5,6-dihydro-2H-1,2,4-thiadiazin-3-amine 1,1-dioxide (C8)

1,8-Diazabicyclo[5.4.0]undec-7-ene (25.8 g, 169 mmol) was added in one portion to a room temperature (13° C.) suspension of C7 (75.0 g, 169 mmol) in methanol (1.5 L). The reaction mixture was refluxed for 16 hours, whereupon it was cooled and concentrated in vacuo. After the residue had been dissolved in ethyl acetate (2.0 L), it was washed with saturated aqueous sodium chloride solution (600 mL), dried over sodium sulfate, filtered, and concentrated under reduced pressure to provide the product (76 g) as a yellow oil, which was used directly in the following step.

Step 9. Synthesis of tert-butyl [(5S)-5-(4-bromo-1,3-thiazol-2-yl)-2,5-dimethyl-1,1-dioxido-5,6-dihydro-2H-1,2,4-thiadiazin-3-yl]carbamate (C9)

Di-tert-butyl dicarbonate (92.2 g, 422 mmol) and triethylamine (59.9 g, 592 mmol) were added to a room temperature (~13° C.) solution of C8 (from the previous step, 76 g, ≤169 mmol) in dichloromethane (1.5 L), and the reaction mixture was stirred at 35° C. for 36 hours, whereupon it was cooled and concentrated in vacuo to afford a yellow oil. This was combined with two similar crude products from two-step reaction sequences carried out on C7 (94.0 g, 212 mmol, and 33.8 g, 76.2 mmol), and the resulting material was purified via silica gel chromatography (Gradient: 3% to 20% ethyl acetate in petroleum ether). The fractions containing product were concentrated until approximately 50 mL of solvent remained, and then diluted with petroleum ether (1 L); this mixture was stirred at room temperature (~13° C.) for 30 minutes. The resulting solid was collected via filtration to afford the product (90 g) as a white solid. The mother liquor was concentrated under reduced pressure, and the residue was chromatographed on silica gel (Gradient: 3% to 20% ethyl acetate in petroleum ether) to provide additional product as a white solid (4.1 g). Combined yield: 94.1 g, 214 mmol, 47% over 2 steps. LCMS m/z 440.6 [M+H]$^+$ (bromine isotope pattern observed). $^1$H NMR (400 MHz, CDCl$_3$) δ 10.93 (br s, 1H), 7.22 (s, 1H), 4.42 (d, J=14.0 Hz, 1H), 3.66 (d, J=13.8 Hz, 1H), 3.28 (s, 3H), 1.94 (s, 3H), 1.54 (s, 9H).

Step 10. Synthesis of tert-butyl [(5S)-5-{4-[(diphenylmethylidene)amino]-1,3-thiazol-2-yl}-2,5-dimethyl-1,1-dioxido-5,6-dihydro-2H-1,2,4-thiadiazin-3-yl]carbamate (C10)

A mixture of C9 (44.25 g, 100.7 mmol), tris(dibenzylideneacetone)dipalladium(0) (8.38 g, 9.15 mmol), biphenyl-2-yl(di-tert-butyl)phosphane (John Phos; 6.37 g, 21.3 mmol), sodium tert-butoxide (32.2 g, 335 mmol), and 1,1-diphenylmethanimine (20.4 mL, 122 mmol) in toluene (640 mL) was evacuated and charged with nitrogen. This evacuation cycle was repeated twice, whereupon the reaction mixture was stirred at 60° C. for 1 hour. It was then filtered through diatomaceous earth, and the filtrate was concentrated in vacuo to provide the product as an amber oil. This material was taken directly to the following step.

Step 11. Synthesis of tert-butyl [(5S)-5-(4-amino-1,3-thiazol-2-yl)-2,5-dimethyl-1,1-dioxido-5,6-dihydro-2H-1,2,4-thiadiazin-3-yl]carbamate (P1)

A solution of C10 (from the previous step, ≤100.7 mmol) in methanol (1.34 L) was treated with hydroxylamine hydrochloride (14.0 g, 201 mmol) and sodium acetate (16.5 g, 201 mmol). The reaction mixture was stirred at room temperature for 1 hour, whereupon saturated aqueous sodium bicarbonate solution was added. The resulting mixture was extracted twice with ethyl acetate; the combined organic layers were washed with saturated aqueous sodium chloride solution, dried over sodium sulfate, filtered, and concentrated in vacuo. Silica gel chromatography (Gradient: 0% to 100% ethyl acetate in heptane) afforded the product as an amber solid. Yield: 31.3 g, 83.4 mmol, 83% over 2 steps. LCMS m/z 374.1 [M−H$^+$]. $^1$H NMR (400 MHz, CD$_3$OD) δ 6.02 (s, 1H), 4.44 (d, J=13.9 Hz, 1H), 4.09 (d, J=14 Hz, 1H), 3.17 (s, 3H), 1.85 (br s, 3H), 1.50 (s, 9H).

Preparation P2

N-[(5S)-5-(4-Amino-1,3-thiazol-2-yl)-2,5-dimethyl-1,1-dioxido-5,6-dihydro-2H-1,2,4-thiadiazin-3-yl]benzamide (P2)

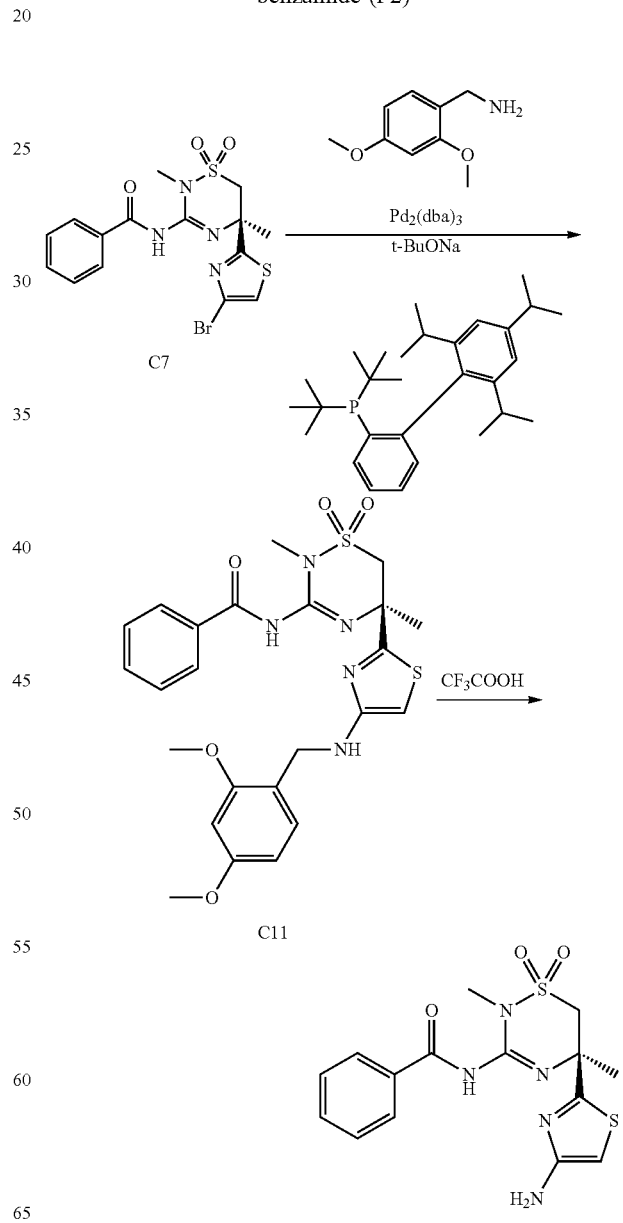

Step 1. Synthesis of N-[(5S)-5-{4-[(2, 4-dimethoxy-benzyl)amino]-1,3-thiazol-2-yl}-2,5-dimethyl-1,1-dioxido-5,6-dihydro-2H-1,2,4-thiadiazin-3-yl]benzamide (C11)

A mixture of tris(dibenzylideneacetone)dipalladium(0) (87.9 mg, 95.9 µmol), di-tert-butyl[2',4',6'-tri(propan-2-yl)biphenyl-2-yl]phosphane (95%, 125 mg, 0.279 mmol), and sodium tert-butoxide (406 mg, 4.22 mmol) in 1,4-dioxane (5 mL, which had been sparged with argon) was stirred at 70° C. for 10 minutes, whereupon a solution of C7 (826 mg, 1.86 mmol) and 1-(2,4-dimethoxyphenyl)methanamine (561 mg, 3.36 mmol) in 1,4-dioxane (5 mL, which had been spared w/ argon) was added. Stirring was continued at 70° C. for 15 minutes, at which time the reaction mixture was allowed to cool to room temperature. It was then poured into aqueous sodium bicarbonate solution (30 mL) and extracted with ethyl acetate (3×30 mL). The combined ethyl acetate layers were dried over sodium sulfate, filtered, and concentrated in vacuo. Chromatography on silica gel (Gradient: 0% to 100% ethyl acetate in heptane) afforded the product as an orange-white solid. Yield: 925 mg, 1.75 mmol, 94%. LCMS m/z 530.2 [M+H]$^+$. $^1$H NMR (400 MHz, CDCl$_3$) δ 8.26-8.21 (m, 2H), 7.57-7.51 (m, 1H), 7.48-7.42 (m, 2H), 7.18 (d, J=8.2 Hz, 1H), 6.47 (d, half of AB quartet, J=2.3 Hz, 1H), 6.43 (dd, half of ABX pattern, J=8.2, 2.4 Hz, 1H), 6.06 (br s, 1H), 4.40 (d, J=13.8 Hz, 1H), 4.28 (s, 2H), 3.85 (s, 3H), 3.80 (s, 3H), 3.70 (d, J=13.8 Hz, 1H), 3.46 (s, 3H), 1.97 (s, 3H).

Step 2. Synthesis of N-[(5S)-5-(4-amino-1,3-thiazol-2-yl)-2,5-dimethyl-1,1-dioxido-5,6-dihydro-2H-1,2,4-thiadiazin-3-yl]benzamide (P2)

Trifluoroacetic acid (2.0 mL) was added drop-wise to a 0° C. solution of C11 (922 mg. 1.74 mmol) in dichloromethane (15 mL). The reaction mixture was stirred at 0° C. for 1 hour, whereupon it was concentrated in vacuo; the residue was partitioned between saturated aqueous sodium bicarbonate solution (30 mL) and ethyl acetate (30 mL), and the aqueous layer was extracted with ethyl acetate (2×30 mL). The combined organic layers were dried over sodium sulfate, filtered, and concentrated under reduced pressure. Chromatography on silica gel (Gradient: 0% to 100% ethyl acetate in heptane) provided the product as a yellow-orange-white solid. Yield: 475 mg, 1.25 mmol, 72%. LCMS m/z 380.1 [M+H]$^+$. $^1$H NMR (400 MHz, CDCl$_3$) δ 8.27-8.21 (m, 2H), 7.57-7.51 (m, 1H), 7.45 (br dd, J=8, 7.3 Hz, 2H), 6.19 (s, 1H), 4.44 (d, J=13.8 Hz, 1H), 3.71 (d, J=13.8 Hz, 1H), 3.46 (s, 3H), 1.98 (s, 3H).

Preparation P3

N-(6-Cyclopropyl-5-{4-[(2,4-dimethoxybenzyl)amino]-1,3-thiazol-2-yl}-2,5-dimethyl-1,1-dioxido-5,6-dihydro-2H-1,2,4-thiadiazin-3-yl)benzamide (P3)

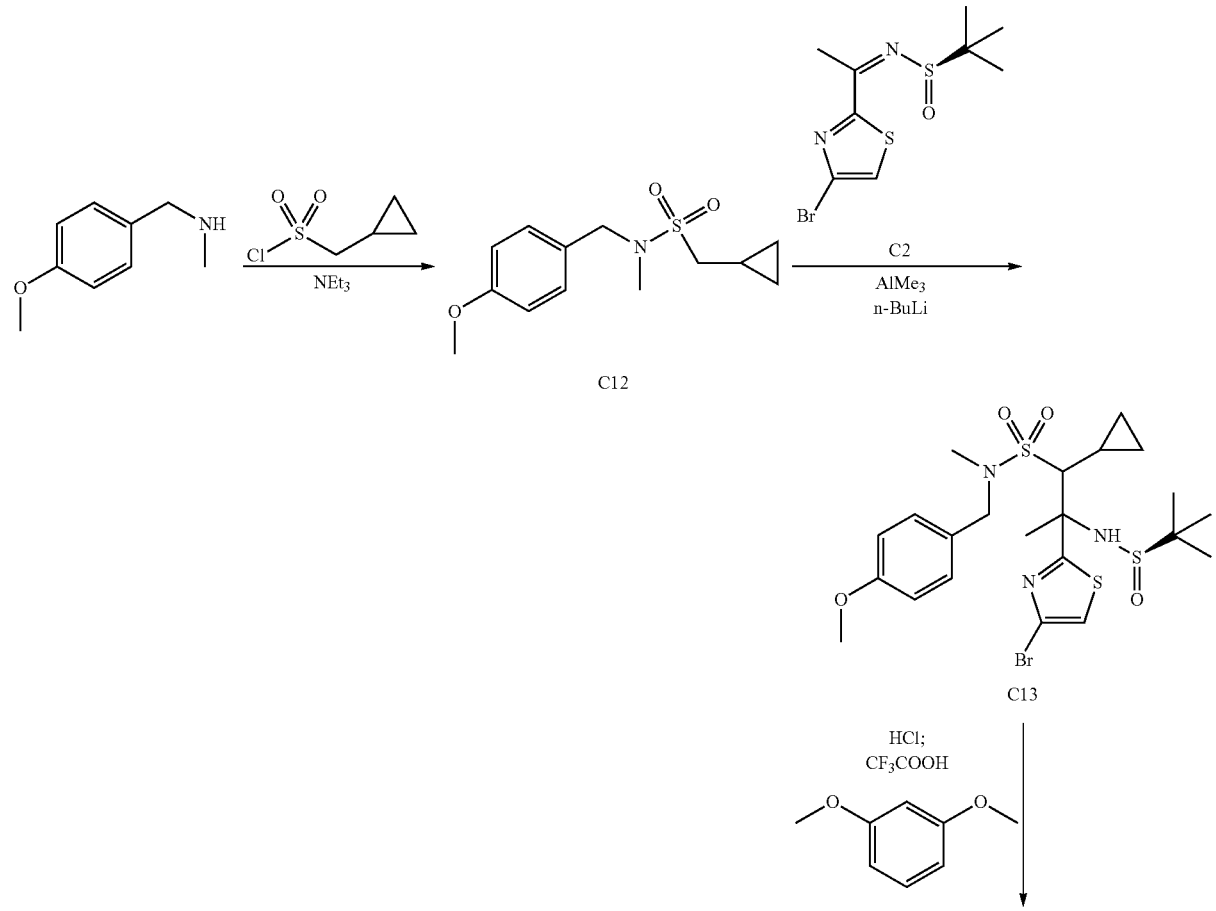

-continued

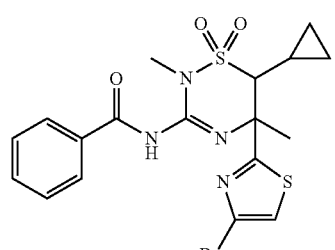
C16

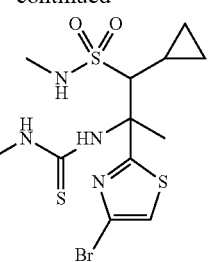
C15

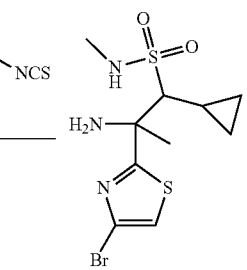
C14

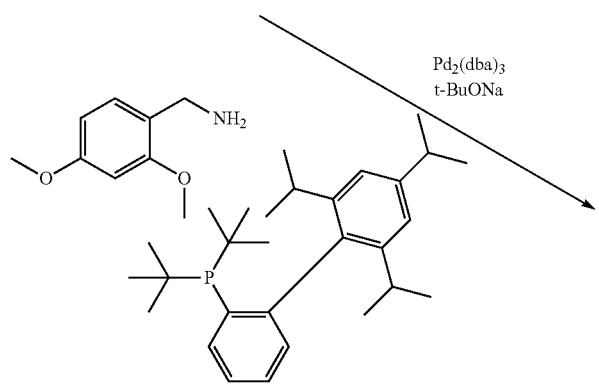

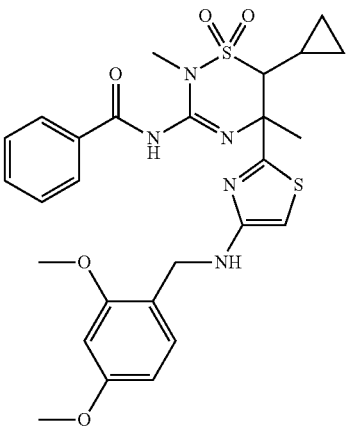
P3

Step 1. Synthesis of 1-cyclopropyl-N-(4-methoxybenzyl)-N-methylmethanesulfonamide (C12)

Triethylamine (4.51 mL, 32.3 mmol) was added to a −20° C. solution of 1-(4-methoxyphenyl)-N-methylmethanamine (5.38 g, 35.6 mmol) in dichloromethane (132 mL). After drop-wise addition of cyclopropylmethanesulfonyl chloride (5.00 g, 32.3 mmol), the reaction mixture was allowed to warm to room temperature over a period of 6 hours and was then stirred for an additional 16 hours. It was then partitioned between water (200 mL) and dichloromethane (250 mL) and the aqueous layer was extracted with dichloromethane (3×100 mL). The combined organic layers were washed with saturated aqueous sodium chloride solution (50 mL), dried over sodium sulfate, filtered, and concentrated in vacuo. The residue was adsorbed onto silica gel as a solution in dichloromethane; silica gel chromatography (Gradient: 0% to 70% ethyl acetate in heptane, followed by ethyl acetate to elute material that had precipitated on the column) afforded a brown solid. This material was triturated with heptane (50 mL); the resulting solid was isolated via filtration and washed with heptane (3×15 mL) to provide the product as a white solid. Yield: 7.4 g, 27 mmol, 84%. $^1$H NMR (400 MHz, CDCl$_3$) δ 7.29 (br d, J=8.5 Hz, 2H), 6.90 (br d, J=8.7 Hz, 2H), 4.32 (s, 2H), 3.82 (s, 3H), 2.94 (d, J=7.1 Hz, 2H), 2.79 (s, 3H), 1.21-1.10 (m, 1H), 0.77-0.68 (m, 2H), 0.41-0.32 (m, 2H).

Step 2. Synthesis of 2-(4-bromo-1,3-thiazol-2-yl)-2-{[(R)-tert-butylsulfinyl]amino}-1-cyclopropyl-N-(4-methoxybenzyl)-N-methylpropane-1-sulfonamide (C13)

n-Butyllithium (2.5 M solution in hexanes; 1.29 mL, 3.23 mmol) was added in a drop-wise manner to a −78° C. solution of C12 (0.871 g, 3.23 mmol) in tetrahydrofuran (20 mL), at a rate that kept the reaction temperature below −70° C. This reaction mixture was stirred at −78° C. for 1 hour. In a separate flask, trimethylaluminum (2.0 M solution in toluene; 0.808 mL, 1.62 mmol) was added drop-wise to a −78° C. solution of C2 (0.500 g, 1.62 mmol) in toluene (8 mL), and this reaction mixture was allowed to stir at −78° C. for 20 minutes. The C12 reaction mixture was then added via cannula to the C2 reaction mixture, and stirring was continued at −78° C. for 3.5 hours, whereupon the reaction was quenched with water (50 mL) and allowed to warm to room temperature. After extraction of the aqueous layer with ethyl acetate (3×25 mL), the combined organic layers were dried over sodium sulfate, filtered, and concentrated in vacuo. The residue was adsorbed onto silica gel as a solution in dichloromethane, and purified via chromatography on silica gel (Gradient: 0% to 100% ethyl acetate in heptane) to afford the product as a white solid. By $^1$H NMR analysis, this material consisted of an approximately 3:2 mixture of diastereomers. Yield: 0.614 g, 1.06 mmol, 65%. $^1$H NMR (400 MHz, CDCl$_3$), characteristic peaks: δ 7.25-7.20 (m, 2H), [7.20 (s) and 7.14 (s), total 1H], 6.88-6.82 (m, 2H), [3.79 (s) and 3.79 (s), total 3H], [3.38 (d, J=11.2 Hz) and 3.25 (d, J=11.0 Hz), total 1H], [2.67 (s) and 2.65 (s), total 3H], [2.10 (s) and 2.06 (s), total 3H], [1.39 (s) and 1.34 (s), total 9H], 1.08-0.39 (m, 5H).

Step 3. Synthesis of 2-amino-2-(4-bromo-1,3-thiazol-2-yl)-1-cyclopropyl-N-methylpropane-1-sulfonamide (C14)

A solution of hydrogen chloride in 1,4-dioxane (4.0 M, 1.60 mL, 6.40 mmol) was added to a solution of C13 (0.614 g, 1.06 mmol) in dichloromethane (10 mL) and methanol (2 mL). The reaction mixture was stirred at room temperature for 2 hours, whereupon it was concentrated in vacuo, and the residue was azeotroped with toluene (2×50 mL). The resulting solid was dissolved in chloroform (10 mL) and treated with 1,3-dimethoxybenzene (0.833 mL, 6.36 mmol) and trifluoroacetic acid (1.5 mL, 19 mmol). After stirring at room temperature for 16 hours, the reaction mixture was concentrated in vacuo, and the residue was treated with aqueous hydrochloric acid (0.25 M, 60 mL) and washed with diethyl ether (3×100 mL). These organic washes were discarded, and the aqueous layer was basified to pH 9 via addition of solid sodium bicarbonate. It was then extracted with ethyl acetate (3×100 mL), and the combined ethyl acetate layers were dried over sodium sulfate, filtered, and concentrated under reduced pressure to provide the product as a white solid. By $^1$H NMR analysis, this material consisted of an approximately 3:2 mixture of diastereomers. Yield: 0.40 g, 1.1 mmol, quantitative. $^1$H NMR (400 MHz, CDCl$_3$), characteristic peaks: δ [7.37 (s) and 7.36 (s), total 1H], [3.55 (d, J=10.9 Hz) and 3.52 (d, J=11.0 Hz), total 1H], [2.91 (s) and 2.83 (s), total 3H], [2.17 (s) and 2.10 (s), total 3H], 1.0-0.48 (m, 4H).

Step 4. Synthesis of N-{[2-(4-bromo-1,3-thiazol-2-yl)-1-cyclopropyl-1-(methylsulfamoyl)propan-2-yl]carbamothioyl}benzamide (C15)

Benzoyl isothiocyanate (0.212 mL, 1.58 mmol) was added to a solution of C14 (0.40 g, 1.1 mmol) in dichloromethane (15 mL), and the reaction mixture was stirred at room temperature for 16 hours. Removal of solvent in vacuo provided the crude product as a yellow solid (0.60 g), which was used directly in the following step.

Step 5. Synthesis of N-[5-(4-bromo-1,3-thiazol-2-yl)-6-cyclopropyl-2,5-dimethyl-1,1-dioxido-5,6-dihydro-2H-1,2,4-thiadiazin-3-yl]benzamide (C16)

To an acetonitrile (15 mL) solution of C15 (from the previous step; 0.60 g, ≤1.1 mmol) was added potassium carbonate (240 mg, 1.74 mmol), followed by iodomethane (0.108 mL, 1.73 mmol), and the reaction mixture was allowed to stir at room temperature for 16 hours. It was then diluted with saturated aqueous ammonium chloride solution (50 mL) and water (20 mL), and the resulting mixture was extracted with ethyl acetate (3×100 mL). The combined organic layers were filtered and concentrated in vacuo; the residue was adsorbed onto silica gel as a solution in dichloromethane. Silica gel chromatography (Gradient: 0% to 60% ethyl acetate in heptane) provided the product as a white solid. By $^1$H NMR analysis, this material consisted of an approximately 7:4 mixture of diastereomers. Four isomers were observed via chiral supercritical fluid chromatography (Column: Phenomenex Lux Cellulose-4, 5 μm; Mobile phase A: carbon dioxide; Mobile phase B: methanol containing 0.2% ammonium hydroxide; Gradient: 5% to 60% B), in a ratio of 32:5:11:53. Yield: 0.284 g, 0.59 mmol, 54% over 2 steps. $^1$H NMR (400 MHz, CDCl$_3$), characteristic peaks: δ 8.26-8.21 (m, 2H), 7.58-7.52 (m, 1H), 7.49-7.43 (m, 2H), [7.25 (s) and 7.23 (s), total 1H], [3.58 (d, J=11.0 Hz) and 2.95 (d, J=10.8 Hz), total 1H], [3.50 (s) and 3.47 (s), total 3H], [2.09 (s) and 2.08 (s), total 3H], 1.13-0.80 (m, 3H), 0.53-0.34 (m, 1H).

Step 6. Synthesis of N-(6-cyclopropyl-5-{4-[(2,4-dimethoxybenzyl)amino]-1,3-thiazol-2-yl}-2,5-dimethyl-1,1-dioxido-5,6-dihydro-2H-1,2,4-thiadiazin-3-yl)benzamide (P3)

A mixture of sodium tert-butoxide (97%, 0.117 g, 1.18 mmol), tris(dibenzylideneacetone)dipalladium(0) (97%, 25.4 mg, 26.9 μmol), and di-tert-butyl[2',4',6'-tri(propan-2-yl)biphenyl-2-yl]phosphane (95%, 36.1 mg, 80.8 μmol) was stirred under nitrogen, and then purged in three cycles of evacuation followed by nitrogen fill. 1,4-Dioxane (5 mL) was added, and the resulting mixture was stirred at 70° C. for 10 minutes, whereupon a solution of C16 (0.26 g, 0.54 mmol) and 1-(2,4-dimethoxyphenyl)methanamine (0.145 mL, 0.965 mmol) in 1,4-dioxane (5 mL) was added to the 70° C. mixture. Stirring was continued at 70° C. for 20 minutes; the reaction mixture was then cooled to room temperature and poured into saturated aqueous sodium bicarbonate solution (100 mL). The mixture was extracted with ethyl acetate (3×100 mL), and the combined organic layers were dried over sodium sulfate, filtered, and concentrated under reduced pressure. The residue was adsorbed onto silica gel as a solution in dichloromethane and subjected to chromatography on silica gel (Gradient: 0% to 70% ethyl acetate in heptane), providing the product as a white solid. By $^1$H NMR analysis, this material consisted of an approximately 1:1 mixture of diastereomers. Yield: 288 mg, 0.506 mmol, 94%. LCMS m/z 570.3 [M+H]$^+$. $^1$H NMR (400 MHz, CDCl$_3$), characteristic peaks: δ [12.09 (br s) and 11.96 (br s), total 1H], 8.27-8.19 (m, 2H), 7.56-7.49 (m, 1H), 7.48-7.40 (m, 2H), [7.19 (d, J=8.2 Hz) and 7.18 (d, J=8.2 Hz), total 1H], 6.48-6.45 (m, 1H), 6.43 (dd, half of ABX pattern, J=8.2, 2.4 Hz, 1H), [5.89 (br s) and 5.83 (br s), total 1H], [4.24 (s) and 4.23 (s), total 2H], 3.84 (s, 3H), [3.80 (s) and 3.80 (s), total 3H], [3.49 (s) and 3.45 (s), total 3H], [2.07 (s) and 2.03 (s), total 3H].

Preparation P4
N-(5-{4-[(2,4-Dimethoxybenzyl)amino]-1,3-thiazol-2-yl}-2,5,6,6-tetramethyl-1,1-dioxido-5,6-dihydro-2H-1,2,4-thiadiazin-3-yl)benzamide (P4)
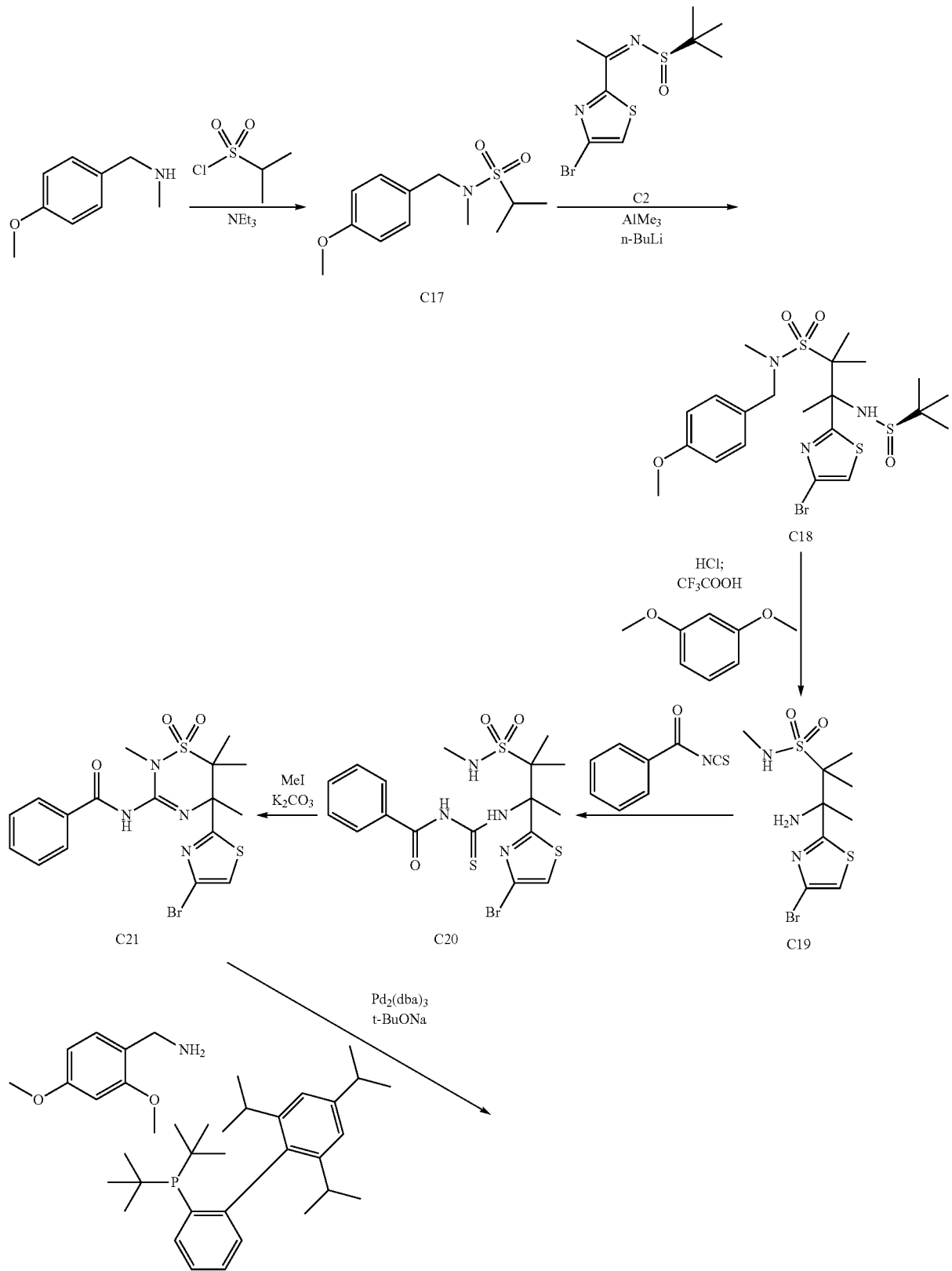

-continued

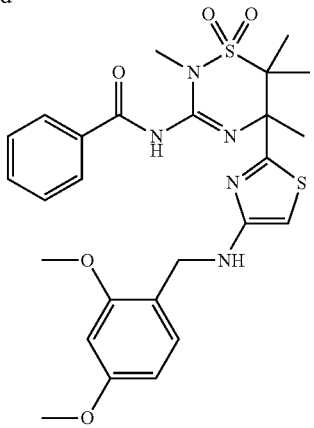

P4

Step 1. Synthesis of N-(4-methoxybenzyl)-N-methylpropane-2-sulfonamide (C17)

Triethylamine (4.50 mL, 32.3 mmol) was added to a −20° C. solution of 1-(4-methoxyphenyl)-N-methylmethanamine (5.38 g, 35.6 mmol) in dichloromethane (130 mL). Propane-2-sulfonyl chloride (4.61 g, 32.3 mmol) was introduced drop-wise; the reaction mixture was then allowed to warm to room temperature over a period of 6 hours and stir for an additional 16 hours. The reaction mixture was partitioned between water (200 mL) and dichloromethane (250 mL), and the aqueous layer was extracted with dichloromethane (3×100 mL). The combined organic layers were washed with saturated aqueous sodium chloride solution (50 mL), dried over sodium sulfate, filtered, and concentrated in vacuo. The residue was adsorbed onto silica gel as a solution in dichloromethane and subjected to silica gel chromatography (Gradient: 0% to 70% ethyl acetate in heptane); during this process, the product partially precipitated on the chromatographic column, so the column was also eluted with ethyl acetate. The material from the column was obtained as a brown solid, which was then triturated with heptane (50 mL) to afford a white solid. This material was washed with heptane (3×15 mL), providing the product as a white solid. Yield: 5.47 g, 21.3 mmol, 66%. $^1$H NMR (400 MHz, CDCl$_3$) δ 7.28 (br d, J=8.8 Hz, 2H), 6.89 (br d, J=8.8 Hz, 2H), 4.33 (s, 2H), 3.82 (s, 3H), 3.28 (septet, J=6.8 Hz, 1H), 2.78 (s, 3H), 1.40 (d, J=6.8 Hz, 6H).

Step 2. Synthesis of 3-(4-bromo-1,3-thiazol-2-yl)-3-{[(R)-tert-butylsulfinyl]amino}-N-(4-methoxybenzyl)-N,2-dimethylbutane-2-sulfonamide (C18)

Conversion of C17 to C18 was carried out using the method described for synthesis of C13 from C12 in Preparation P3. The product was obtained as an orange solid; by $^1$H NMR analysis, this material consisted of an approximately 3:2 mixture of diastereomers. Yield: 528 mg, 0.932 mmol, 58%. $^1$H NMR (400 MHz, CDCl$_3$), characteristic peaks: δ 7.24-7.16 (m, 3H), 6.87-6.80 (m, 2H), [6.63 (br s) and 6.23 (br s), total 1H], [3.79 (s) and 3.78 (s), total 3H], 2.78-2.65 (m, 3H), 2.02 (s, 3H), [1.78 (s) and 1.68 (s), total 3H], [1.63 (s) and 1.55 (s), total 3H], [1.36 (s) and 1.36 (s), total 9H].

Step 3. Synthesis of 3-amino-3-(4-bromo-1,3-thiazol-2-yl)-N,2-dimethylbutane-2-sulfonamide (C19)

Conversion of C18 to C19 was carried out using the method described for synthesis of C14 from C13 in Preparation P3, except that the trifluoroacetic acid-mediated deprotection was effected without added solvent. The product was isolated as a white solid. Yield: 291 mg, 0.850 mmol, 91%. $^1$H NMR (400 MHz, CDCl$_3$) δ 7.21 (s, 1H), 2.81 (s, 3H), 1.73 (s, 3H), 1.65 (s, 3H), 1.59 (s, 3H).

Step 4. Synthesis of N-{[2-(4-bromo-1,3-thiazol-2-yl)-3-methyl-3-(methylsulfamoyl)butan-2-yl]carbamothioyl}benzamide (C20)

Conversion of C19 (290 mg, 0.847 mmol) to C20 was effected using the procedure described for synthesis of C15 from C14 in Preparation P3. The product was obtained as a yellow solid, which was taken directly into the following step. LCMS m/z 505.1, 507.1 [M+H]$^+$.

Step 5. Synthesis of N-[5-(4-bromo-1,3-thiazol-2-yl)-2,5,6,6-tetramethyl-1,1-dioxido-5,6-dihydro-2H-1,2,4-thiadiazin-3-yl]benzamide (C21)

Conversion of C20 (from the previous reaction, ≤0.847 mmol) to C21 was carried out using the method described for synthesis of C16 from C15 in Preparation P3. The product was isolated as a white solid. Yield: 170 mg, 0.361 mmol, 43% over 2 steps. LCMS m/z 471.1, 473.1 [M+H]$^+$. $^1$H NMR (400 MHz, CDCl$_3$) δ 12.45 (br s, 1H), 8.27-8.23 (m, 2H), 7.58-7.52 (m, 1H), 7.49-7.43 (m, 2H), 7.25 (s, 1H), 3.52 (s, 3H), 2.03 (s, 3H), 1.81 (s, 3H), 1.56 (s, 3H).

Step 6. Synthesis of N-(5-{4-[(2,4-dimethoxybenzyl)amino]-1,3-thiazol-2-yl}-2,5,6,6-tetramethyl-1,1-dioxido-5,6-dihydro-2H-1,2,4-thiadiazin-3-yl)benzamide (P4)

A mixture of sodium tert-butoxide (97%, 67.0 mg, 0.676 mmol), tris(dibenzylideneacetone)dipalladium(0) (97%, 14.5 mg, 15.4 μmol), and di-tert-butyl[2',4',6'-tri(propan-2-yl)biphenyl-2-yl]phosphane (95%, 20.6 mg, 46.1 μmol) was stirred under nitrogen, and then purged in three cycles of evacuation followed by nitrogen fill. 1,4-Dioxane (10 mL) was added, and the solution was stirred at 70° C. for 10 minutes, at which time a solution of C21 (0.145 g, 0.308 mmol) and 1-(2,4-dimethoxyphenyl)methanamine (92.6 mg, 0.554 mmol) in 1,4-dioxane (10 mL) was added to the hot (70° C.) reaction mixture. After being stirred at 70° C. for 80 minutes, the reaction mixture was allowed to cool to room temperature, whereupon it was poured into saturated aqueous sodium bicarbonate solution (100 mL). The resulting mixture was extracted with ethyl acetate (3×100 mL), and the combined organic layers were dried over sodium sulfate, filtered, and concentrated under reduced pressure to provide an orange oil (195 mg), which consisted of an approximately 1:1 mixture of C21 and P4 by LCMS analysis. This material was resubjected to the same reaction conditions using the following reagent quantities: sodium tert-butoxide (97%, 41.3 mg, 0.417 mmol), tris(dibenzylideneacetone)dipalladium(0) (97%, 8.94 mg, 9.47 µmol), di-tert-butyl[2',4',6'-tri(propan-2-yl)biphenyl-2-yl]phosphane (95%, 12.7 mg, 28.4 µmol), and 1-(2,4-dimethoxyphenyl)methanamine (57.0 mg, 0.341 mmol). In this case, the reaction mixture was stirred at 70° C. for 20 minutes. The crude product from this resubmission was adsorbed onto silica gel as a solution in dichloromethane; silica gel chromatography (Gradient: 0% to 70% ethyl acetate in heptane) afforded the product as a white solid. Yield: 135 mg, 0.242 mmol, 79%. $^1$H NMR (400 MHz, CDCl$_3$) δ 12.31 (br s, 1H), 8.27-8.23 (m, 2H), 7.55-7.50 (m, 1H), 7.47-7.41 (m, 2H), 7.20 (d, J=8.2 Hz, 1H), 6.48 (d, half of AB quartet, J=2.4 Hz, 1H), 6.45 (dd, half of ABX pattern, J=8.3, 2.4 Hz, 1H), 5.75 (s, 1H), 4.75-4.68 (m, 1H), 4.26-4.21 (m, 2H), 3.85 (s, 3H), 3.82 (s, 3H), 3.51 (s, 3H), 2.03 (s, 3H), 1.82 (s, 3H), 1.42 (s, 3H).

Preparation P5

N-(5-{4-[(2,4-Dimethoxybenzyl)amino]-1,3-thiazol-2-yl}-2,5,6-trimethyl-1,1-dioxido-5,6-dihydro-2H-1,2,4-thiadiazin-3-yl)benzamide (P5)

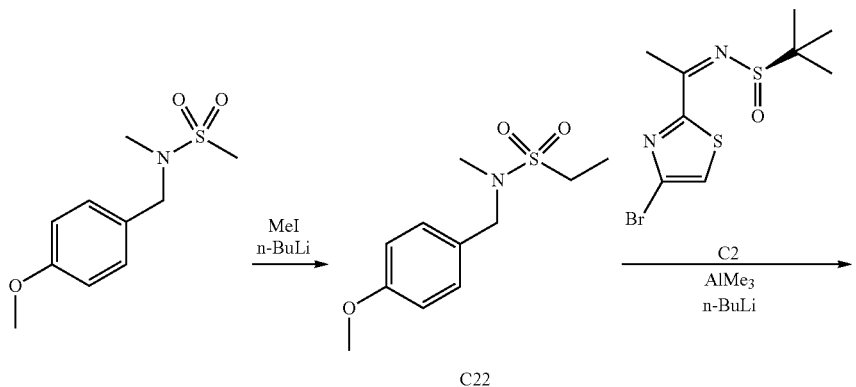

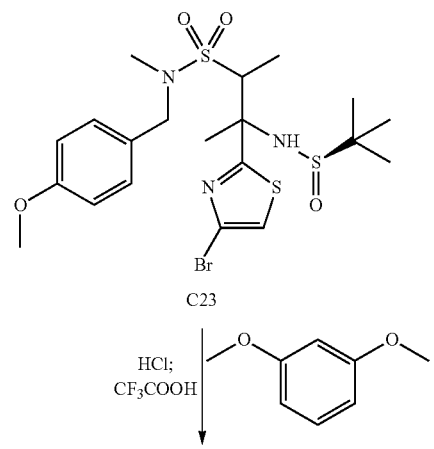

-continued

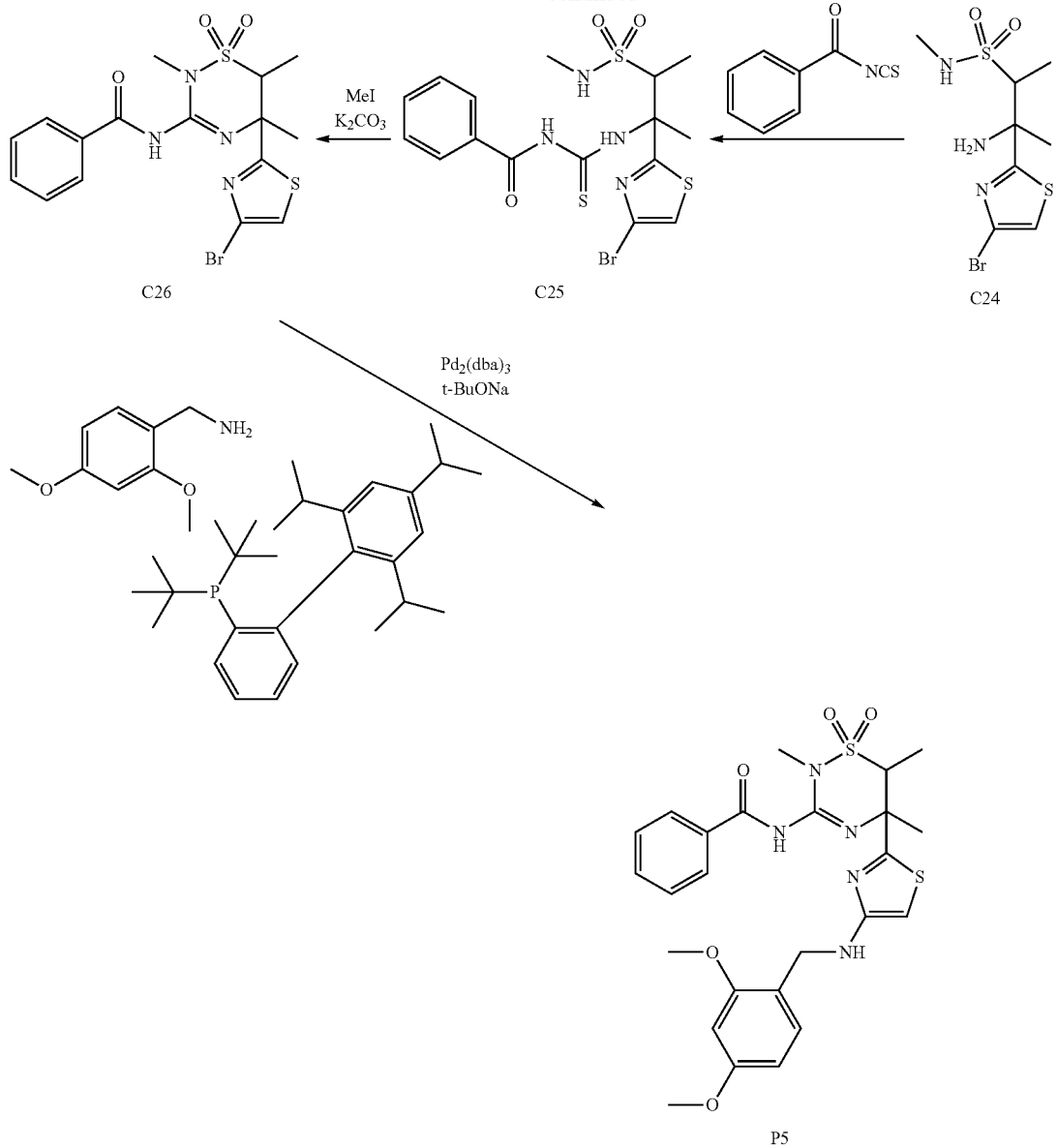

Step 1. Synthesis of N-(4-methoxybenzyl)-N-methylethanesulfonamide (C22)

n-Butyllithium (2.5 M solution in hexanes; 3.66 mL, 9.15 mmol) was added drop-wise to a −72° C. (internal reaction temperature) solution of N-(4-methoxybenzyl)-N-methylmethanesulfonamide (2.00 g, 8.72 mmol) in tetrahydrofuran (35 mL), at a rate that maintained the internal temperature at −70° C. or below. After the reaction mixture had stirred at −70° C. for 1 hour, iodomethane (0.983 mL, 15.8 mmol) was added in a drop-wise manner, and stirring was continued at −70° C. for 4 hours. The reaction mixture was then allowed to warm to room temperature over 16 hours, whereupon it was diluted with saturated aqueous ammonium chloride solution (150 mL) and water (120 mL). The resulting mixture was extracted with ethyl acetate (3×100 mL), and the combined organic layers were filtered and concentrated in vacuo. The residue was adsorbed onto silica gel as a solution in dichloromethane and subjected to silica gel chromatography (Gradient: 0% to 100% ethyl acetate in heptane), providing the product as a white solid. Yield: 1.92 g, 7.89 mmol, 90%. $^1$H NMR (400 MHz, CDCl$_3$) δ 7.30-7.25 (m, 2H, assumed; partially obscured by solvent peak), 6.90 (br d, J=8.5 Hz, 2H), 4.31 (s, 2H), 3.82 (s, 3H), 3.02 (q, J=7.4 Hz, 2H), 2.77 (s, 3H), 1.39 (t, J=7.4 Hz, 3H).

Step 2. Synthesis of 3-(4-bromo-1,3-thiazol-2-yl)-3-{[(R)-tert-butylsulfinyl]amino}-N-(4-methoxybenzyl)-N-methylbutane-2-sulfonamide (C23)

Conversion of C22 to C23 was carried out using the method described for synthesis of C13 from C12 in Preparation P3. The product was isolated as a white solid. By $^1$H NMR analysis, this material consisted of at least three diastereomers, in a ratio of approximately 5:4:3. Yield: 1.57 g, 2.84 mmol, 73%. $^1$H NMR (400 MHz, CDCl$_3$), characteristic peaks: δ [7.24-7.17 (m) and 6.89-6.83 (m), total 5H],

[3.80 (s), 3.80 (s), and 3.80 (s), total 3H], [2.73 (s), 2.68 (s), and 2.64 (s), total 3H], [2.07 (s), 2.00 (s), and 1.94 (s), total 3H], [1.75 (d, J=7.1 Hz), 1.54 (d, J=7.1 Hz), and 1.53 (d, J=7.1 Hz), total 3H], [1.37 (s), 1.34 (s), and 1.28 (s), total 9H].

Step 3. Synthesis of 3-amino-3-(4-bromo-1,3-thiazol-2-yl)-N-methylbutane-2-sulfonamide (C24)

A solution of hydrogen chloride in 1,4-dioxane (4.0 M, 4.13 mL, 16.5 mmol) was added to a solution of C23 (1.52 g, 2.75 mmol) in dichloromethane (30 mL) and methanol (6 mL), and the reaction mixture was stirred at room temperature for 2 hours. After removal of solvent in vacuo, the residue was azeotroped with toluene (2×50 mL), and the resulting yellow solid was then dissolved in a mixture of 1,3-dimethoxybenzene (5 mL) and trifluoroacetic acid (10 mL). This reaction mixture was stirred at room temperature for 16 hours, whereupon aqueous hydrochloric acid (0.25 M, 100 mL) was added, and the mixture was washed with diethyl ether (3×100 mL). The aqueous layer was basified to pH 9 by addition of 1 M aqueous sodium hydroxide solution, and then extracted with ethyl acetate (3×100 mL). The combined ethyl acetate layers were dried over sodium sulfate, filtered, and concentrated under reduced pressure to provide the product as a colorless oil. By $^1$H NMR analysis, this material consisted of an approximately 3:2 mixture of diastereomers. Yield: 886 mg, 2.70 mmol, 98%. Major diastereomer: $^1$H NMR (400 MHz, CDCl$_3$) δ 7.17 (s, 1H), 4.18 (br q, J=5 Hz, 1H), 3.89 (q, J=7.1 Hz, 1H), 2.85 (d, J=5.2 Hz, 3H), 2.4-2.2 (br s, 2H), 1.82 (s, 3H), 1.33 (d, J=7.1 Hz, 3H). Minor diastereomer: $^1$H NMR (400 MHz, CDCl$_3$) δ 7.18 (s, 1H), 4.00 (q, J=7.2 Hz, 1H), 3.70 (br q, J=5 Hz, 1H), 2.67 (d, J=5.3 Hz, 3H), 2.4-2.2 (br s, 2H), 1.57 (s, 3H), 1.53 (d, J=7.2 Hz, 3H).

Step 4. Synthesis of N-{[2-(4-bromo-1,3-thiazol-2-yl)-3-(methylsulfamoyl)butan-2-yl]carbamothioyl}benzamide (C25)

Conversion of C24 to C25 was effected using the method described for synthesis of C15 from C14 in Preparation P3. The product was obtained as a yellow solid, which was taken directly to the following step.

Step 5. Synthesis of N-[5-(4-bromo-1,3-thiazol-2-yl)-2,5,6-trimethyl-1,1-dioxido-5,6-dihydro-2H-1,2,4-thiadiazin-3-yl]benzamide (C26)

Conversion of C25 to C26 was carried out using the procedure described for synthesis of C16 from C15 in Preparation P3. The product was isolated as a white solid that, by $^1$H NMR analysis, consisted of an approximately 3:2 mixture of diastereomers. Yield: 390 mg, 0.853 mmol, 32% over 2 steps. $^1$H NMR (400 MHz, CDCl$_3$) δ [12.38 (br s) and 12.32 (br s), total 1H], 8.27-8.21 (m, 2H), 7.58-7.52 (m, 1H), 7.49-7.42 (m, 2H), [7.25 (s) and 7.24 (s), total 1H], [4.33 (q, J=7.1 Hz) and 3.78 (q, J=7.1 Hz), total 1H], [3.51 (s) and 3.49 (s), total 3H], [2.03 (s) and 1.93 (s), total 3H], [1.76 (d, J=7.1 Hz) and 1.65 (d, J=7.0 Hz), total 3H].

Step 6. Synthesis of N-(5-{4-[(2,4-dimethoxybenzyl)amino]-1,3-thiazol-2-yl}-2,5,6-trimethyl-1,1-dioxido-5,6-dihydro-2H-1,2,4-thiadiazin-3-yl)benzamide (P5)

Reaction of C26 with 1-(2,4-dimethoxyphenyl)methanamine was carried out according to the procedure described for synthesis of P3 from C16 in Preparation P3. The product was isolated as a yellow solid; by $^1$H NMR analysis, this material consisted of an approximately 1:1 mixture of diastereomers. Yield: 457 mg, 0.840 mmol, 98%. $^1$H NMR (400 MHz, CDCl$_3$), characteristic peaks: δ [12.24 (br s) and 12.05 (br s), total 1H], 8.28-8.18 (m, 2H), 7.56-7.49 (m, 1H), 7.47-7.40 (m, 2H), [7.21 (d, J=8.2 Hz) and 7.20 (d, J=8.2 Hz), total 1H], 6.50-6.42 (m, 2H), [5.75 (s) and 5.73 (s), total 1H], 4.26-4.19 (m, 2H), [3.85 (s), 3.84 (s), 3.81 (s), and 3.81 (s), total 6H], [3.50 (s) and 3.49 (s), total 3H], [2.02 (s) and 1.93 (s), total 3H], [1.61 (d, J=7.0 Hz) and 1.59 (d, J=7.0 Hz), total 3H].

Preparation P6

5-(Difluoromethoxy)pyridine-2-carboxylic acid (P6)

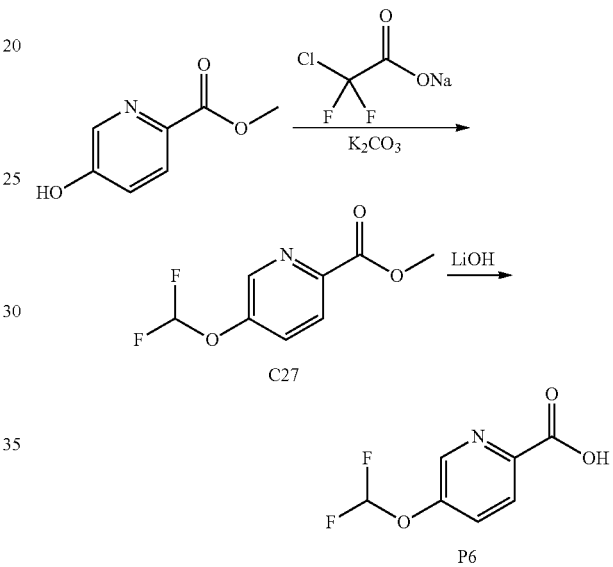

Step 1. Synthesis of methyl 5-(difluoromethoxy)pyridine-2-carboxylate (C27)

Potassium carbonate (45.1 g, 326 mmol) was added to a solution of methyl 5-hydroxypyridine-2-carboxylate (20 g, 130 mmol) in N,N-dimethylformamide (500 mL), and the reaction mixture was stirred at room temperature for 0.5 hours. Sodium chloro(difluoro)acetate (63.7 g, 418 mmol) was introduced, and the resulting mixture was heated at 100° C. for 5 hours, whereupon it was partitioned between saturated aqueous sodium chloride solution (300 mL) and ethyl acetate (300 mL). The aqueous layer was extracted with ethyl acetate (3×200 mL), and the combined organic layers were washed with saturated aqueous sodium chloride solution (2×200 mL), dried, filtered, and concentrated in vacuo. Silica gel chromatography (Eluent: 5:1 petroleum ether/ethyl acetate) afforded the product as a pale yellow oil. Yield: 17 g, 84 mmol, 65%. $^1$H NMR (400 MHz, CDCl$_3$) δ 8.56 (s, 1H), 8.17 (d, J=8.7 Hz, 1H), 7.59 (br d, J=8.7 Hz, 1H), 6.64 (t, $J_{HF}$=71.9 Hz, 1H), 4.00 (s, 3H).

Step 2. Synthesis of 5-(difluoromethoxy)pyridine-2-carboxylic acid (P6)

A solution of C27 (17 g, 84 mmol) in tetrahydrofuran (100 mL) and water (50 mL) was cooled to 0° C. and treated with lithium hydroxide (6.0 g, 250 mmol). After the reaction mixture had stirred at room temperature for 2 hours, it was acidified to a pH of 3 with 1 M aqueous hydrochloric acid. The aqueous layer was extracted with ethyl acetate (3×100 mL), and the combined organic layers were washed with saturated aqueous sodium chloride solution (100 mL), dried, filtered, and concentrated under reduced pressure to provide the product as a white solid. Yield: 13 g, 69 mmol, 82%. LCMS m/z 189.8 [M+H]$^+$. $^1$H NMR (400 MHz, CDCl$_3$) δ 8.52 (d, J=2.4 Hz, 1H), 8.29 (d, J=8.5 Hz, 1H), 7.73 (dd, J=8.6, 2.4 Hz, 1H), 6.68 (t, J$_{HF}$=71.5 Hz, 1H).

Preparation P7

5-(Difluoromethoxy)-3-methylpyridine-2-carboxylic acid (P7)

acetate in petroleum ether). The product was obtained as a yellow solid. Yield: 20.0 g, 150 mmol, 61%. $^1$H NMR (400 MHz, CDCl$_3$) δ 7.94 (d, J=2.5 Hz, 1H), 6.81 (d, J=2.5 Hz, 1H), 4.19-4.07 (br s, 2H), 2.45 (s, 3H).

Step 3. Synthesis of 5-hydroxy-3-methylpyridine-2-carbonitrile (C30)

Sodium nitrite (1.6 M aqueous solution containing 10.3 g of sodium nitrite, 149 mmol) was slowly added to a 0° C. solution of C29 (18.0 g, 135 mmol) in water (243 mL) and concentrated sulfuric acid (67.5 mL). The reaction mixture was warmed to room temperature and then stirred at 100° C. for 3 hours, whereupon it was cooled and extracted with ethyl acetate (3×75 mL). The combined organic layers were washed with water (2×75 mL) and with saturated aqueous sodium chloride solution (2×75 mL), dried, filtered, and

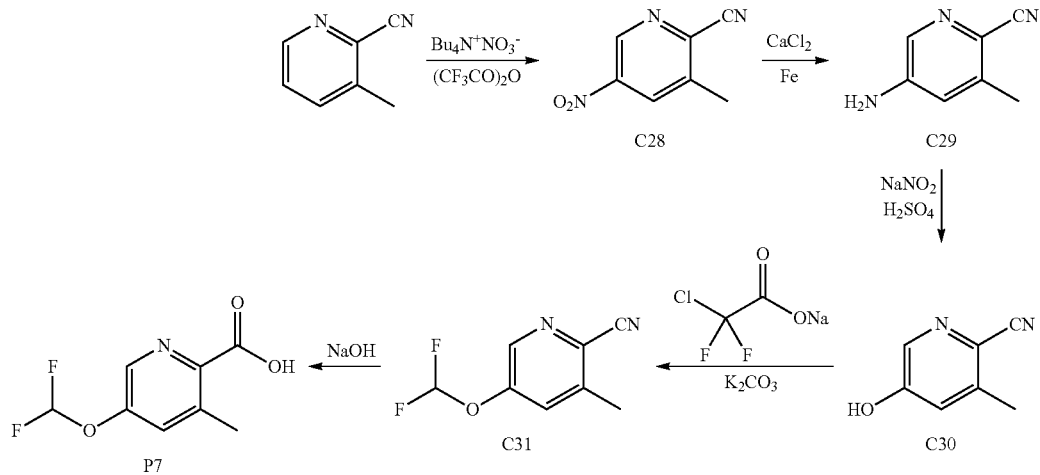

concentrated under reduced pressure to afford the product as a yellow solid. Yield: 16 g, 120 mmol, 89%. $^1$H NMR (400 MHz, DMSO-d$_6$) δ 11.07 (br s, 1H), 8.08 (d, J=2.6 Hz, 1H), 7.20 (d, J=2.3 Hz, 1H), 2.40 (s, 3H).

Step 1. Synthesis of 3-methyl-5-nitropyridine-2-carbonitrile (C28)

A mixture of 3-methylpyridine-2-carbonitrile (128 g, 1.08 mol) and tetrabutylammonium nitrate (363 g, 1.19 mol) in tert-butyl methyl ether (1.3 L) was cooled to 4° C. Trifluoroacetic anhydride (171 mL, 1.21 mol) was added, and the reaction mixture was allowed to stir at room temperature for 60 hours. It was then adjusted to a pH of approximately 7 by addition of 20% aqueous sodium hydroxide solution, and extracted with dichloromethane (3×1 L). The combined organic layers were dried, filtered, and concentrated in vacuo; purification via silica gel chromatography (Gradient: 0% to 10% ethyl acetate in petroleum ether) afforded the product as a yellow solid. Yield: 70 g, 0.43 mmol, 40%. $^1$H NMR (400 MHz, CDCl$_3$) δ 9.36-9.31 (m, 1H), 8.52-8.47 (m, 1H), 2.74 (s, 3H).

Step 2. Synthesis of 5-amino-3-methylpyridine-2-carbonitrile (C29)

To a solution of C28 (40.0 g, 245 mmol) in ethanol (630 mL) and water (70 mL) was added calcium chloride (13.6 g, 123 mmol), followed by iron powder (123 g, 2.20 mol), and the reaction mixture was stirred overnight at room temperature. After filtration of the reaction mixture, the filtrate was concentrated in vacuo, and the residue was purified by chromatography on silica gel (Gradient: 10% to 50% ethyl Step 4. Synthesis of 5-(difluoromethoxy)-3-methylpyridine-2-carbonitrile (C31)

A mixture of C30 (5.70 g, 42.5 mmol), sodium chlorodifluoroacetate (13.0 g, 85.3 mmol), and potassium carbonate (17.6 g, 127 mmol) in N,N-dimethylformamide (175 mL) was stirred for 30 minutes at 100° C. The reaction mixture was then diluted with ethyl acetate (400 mL), and sequentially washed with saturated aqueous ammonium chloride solution (3×200 mL) and saturated aqueous sodium chloride solution (3×200 mL). The combined aqueous layers were extracted with ethyl acetate (200 mL), and the combined organic layers were dried over sodium sulfate, filtered, and concentrated in vacuo. Silica gel chromatography (Gradient: 5% to 15% ethyl acetate in petroleum ether) provided the product as a colorless oil. Yield: 3.9 g, 21 mmol, 49%. $^1$H NMR (400 MHz, CDCl$_3$) δ 8.39 (br d, J=2.1 Hz, 1H), 7.47-7.43 (m, 1H), 6.64 (t, J$_{HF}$=71.5 Hz, 1H), 2.59 (s, 3H).

Step 5. Synthesis of 5-(difluoromethoxy)-3-methylpyridine-2-carboxylic acid (P7)

Aqueous sodium hydroxide solution (1 M, 124 mL, 124 mmol) was added to a solution of C31 (7.60 g, 41.3 mmol)

in ethanol (200 mL), and the reaction mixture was stirred for 16 hours at 70° C. It was then diluted with tert-butyl methyl ether (200 mL) and extracted with water (2×100 mL). The combined aqueous layers were washed with tert-butyl methyl ether (100 mL), acidified to pH 2 with 1 M aqueous hydrochloric acid, and extracted with tert-butyl methyl ether (2×200 mL). The combined organic extracts were dried over sodium sulfate, filtered, and concentrated in vacuo to afford the product as a white solid. Yield: 6.6 g, 32 mmol, 77%. LCMS m/z 203.7 [M+H]$^+$. $^1$H NMR (400 MHz, CD$_3$OD) δ 8.32 (br d, J=2.1 Hz, 1H), 7.62-7.58 (m, 1H), 7.06 (t, J$_{HF}$=72.7 Hz, 1H), 2.64 (s, 3H).

Preparation P8

3-Chloro-5-(difluoromethoxy)pyridine-2-carboxylic acid (P8)

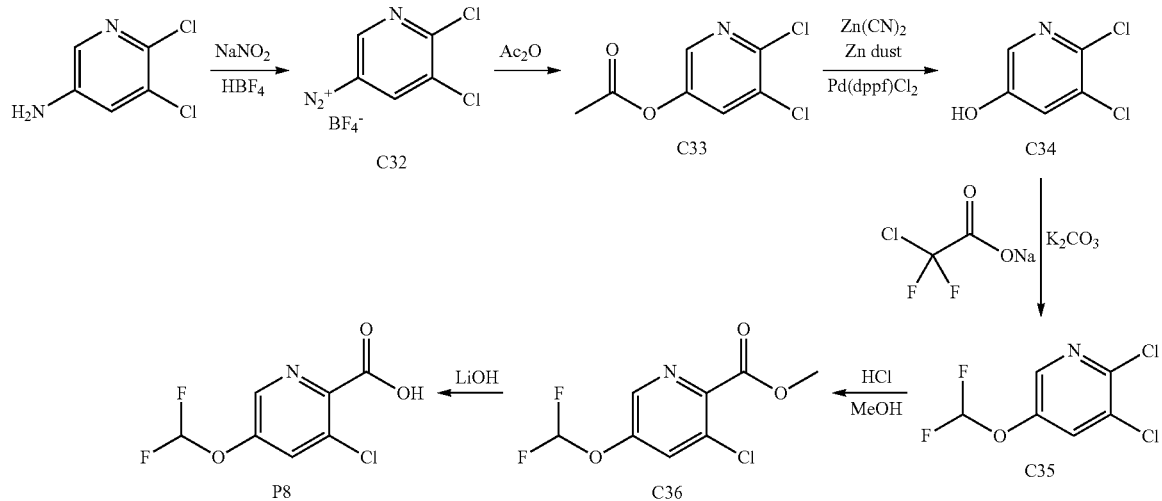

Step 1. Synthesis of 5,6-dichloropyridine-3-diazonium tetrafluoroborate (C32)

To a 0° C. solution of 5,6-dichloropyridin-3-amine (15 g, 92 mmol) in tetrafluoroboric acid (~45% in water; 150 mL) was added a solution of sodium nitrite (6.67 g, 96.6 mmol) in water (90 mL) in a drop-wise manner, during which time the diazonium salt precipitated. After completion of the addition, the reaction mixture was stirred at 0° C. for 1 hour. It was then filtered; the filter cake was washed with petroleum ether (3×200 mL) to afford the product (25.8 g) as a pale red solid. This material was used directly in the next step.

Step 2. Synthesis of 5,6-dichloropyridin-3-yl acetate (C33)

A solution of C32 (from the previous step; 25.8 g, ≤92 mmol) was dissolved in acetic anhydride (75 mL) and slowly warmed to 70° C. When nitrogen evolution had ceased, stirring was continued for 1 hour at 70° C., whereupon the solvent was evaporated. The residue was dissolved in tert-butyl methyl ether (100 mL) and washed with water (4×40 mL). The combined aqueous layers were extracted with additional tert-butyl methyl ether (3×50 mL), and the combined organic layers were washed with saturated aqueous sodium chloride solution (5×20 mL), dried over sodium sulfate, filtered, and concentrated in vacuo. Silica gel chromatography (Gradient: 0% to 25% ethyl acetate in petroleum ether) afforded the product as a yellow oil. Yield: 9.7 g, 47 mmol, 51% over 2 steps. $^1$H NMR (400 MHz, DMSO-d$_6$) δ 8.33 (d, J=2.5 Hz, 1H), 8.18 (d, J=2.5 Hz, 1H), 2.32 (s, 3H).

Step 3. Synthesis of 3-chloro-5-hydroxypyridine-2-carbonitrile (C34)

Zinc cyanide (2.6 g, 22 mmol), zinc dust (145 mg, 2.21 mmol), and [1,1'-bis(diphenylphosphino)ferrocene]dichloropalladium(II) (1.72 g, 2.35 mmol) were added to a room temperature solution of C33 (9.7 g, 47 mmol) in N,N-dimethylformamide (60 mL). The reaction mixture was stirred at 140° C. for 13 hours, whereupon it was diluted with tert-butyl methyl ether (200 mL) and water (150 mL) and filtered through a pad of diatomaceous earth. The aqueous layer of the filtrate was extracted with additional tert-butyl methyl ether (3×50 mL), and the combined organic layers were washed with saturated aqueous sodium chloride solution (8×50 mL), dried over sodium sulfate, filtered, and concentrated in vacuo to provide the product as a brown solid. Yield: 6.8 g, 44 mmol, 94%. $^1$H NMR (400 MHz, CD$_3$OD) δ 8.16 (d, J=2.5 Hz, 1H), 7.38 (d, J=2.5 Hz, 1H).

Step 4. Synthesis of 3-chloro-5-(difluoromethoxy)pyridine-2-carbonitrile (C35)

A mixture of C34 (6.8 g, 44 mmol), sodium chloro(difluoro)acetate (20 g, 180 mmol) and potassium carbonate (36.5 g, 264 mmol) in N,N-dimethylformamide (70 mL) was stirred at 100° C. for 40 minutes (until no gas evolution could be seen). The reaction mixture was diluted with tert-butyl methyl ether (200 mL) and water (150 mL), and the aqueous layer was extracted with additional tert-butyl methyl ether (3×100 mL). The combined organic layers were washed with saturated aqueous sodium chloride solution (8×50 mL), dried over sodium sulfate, filtered, and concentrated under reduced pressure. Chromatography on silica gel (Gradient: 0% to 20% ethyl acetate in petroleum ether) afforded the product as a yellow oil. Yield: 5.55 g, 27.1 mmol, 62%. $^1$H NMR (400 MHz, CDCl$_3$) δ 8.52-8.45 (m, 1H), 7.73-7.65 (m, 1H), 6.68 (t, $J_{HF}$=70.8 Hz, 1H).

Step 5. Synthesis of methyl 3-chloro-5-(difluoromethoxy)pyridine-2-carboxylate (C36)

Compound C35 (4.82 g, 23.6 mmol) was dissolved in a solution of hydrogen chloride in methanol (4 M; 75 mL), and the reaction mixture was stirred at 60° C. for 13 hours. It was then diluted with water (50 mL) and stirred at room temperature for 30 minutes. The mixture was concentrated under reduced pressure and the residual aqueous phase was neutralized via addition of saturated aqueous sodium bicarbonate solution (200 mL) and then extracted with ethyl acetate (3×60 mL). The combined organic layers were washed with saturated aqueous sodium chloride solution (30 mL), dried over sodium sulfate, filtered, and concentrated in vacuo. The resulting material was combined with the crude product from a similar reaction carried out using C35 (500 mg, 2.4 mmol), and the mixture was subjected to silica gel chromatography (Gradient: 0% to 20% ethyl acetate in petroleum ether), providing the product as a yellow oil, which solidified upon standing at room temperature. Yield: 3.4 g, 14 mmol, 54%. $^1$H NMR (400 MHz, CDCl$_3$) δ 8.50-8.43 (m, 1H), 7.68-7.62 (m, 1H), 6.64 (t, $J_{HF}$=71.3 Hz, 1H), 4.02 (s, 3H).

Step 6. Synthesis of 3-chloro-5-(difluoromethoxy)pyridine-2-carboxylic acid (P8)

Lithium hydroxide monohydrate (279 mg, 6.31 mmol) was added to a solution of C36 (1.0 g, 4.2 mmol) in tetrahydrofuran (40 mL) and water (20 mL). The reaction mixture was stirred at room temperature for 3 hours, whereupon it was concentrated in vacuo, and the residual aqueous phase was adjusted to a pH of 2-3 via addition of 2 M aqueous hydrochloric acid. The resulting mixture was extracted with ethyl acetate (7×20 mL), and the combined organic layers were dried over sodium sulfate, filtered, and concentrated under reduced pressure to afford the product as a pale yellow solid. Yield: 720 mg, 3.22 mmol, 77%. LCMS m/z 222.0 [M−H$^+$] (chlorine isotope pattern observed). $^1$H NMR (400 MHz, DMSO-d$_6$) δ 8.51 (d, J=2.0 Hz, 1H), 8.06 (d, J=2.0 Hz, 1H), 7.44 (t, $J_{HF}$=72.8 Hz, 1H).

Preparation P9

2-(Fluoromethyl)-1,3-oxazole-4-carboxylic acid (P9)

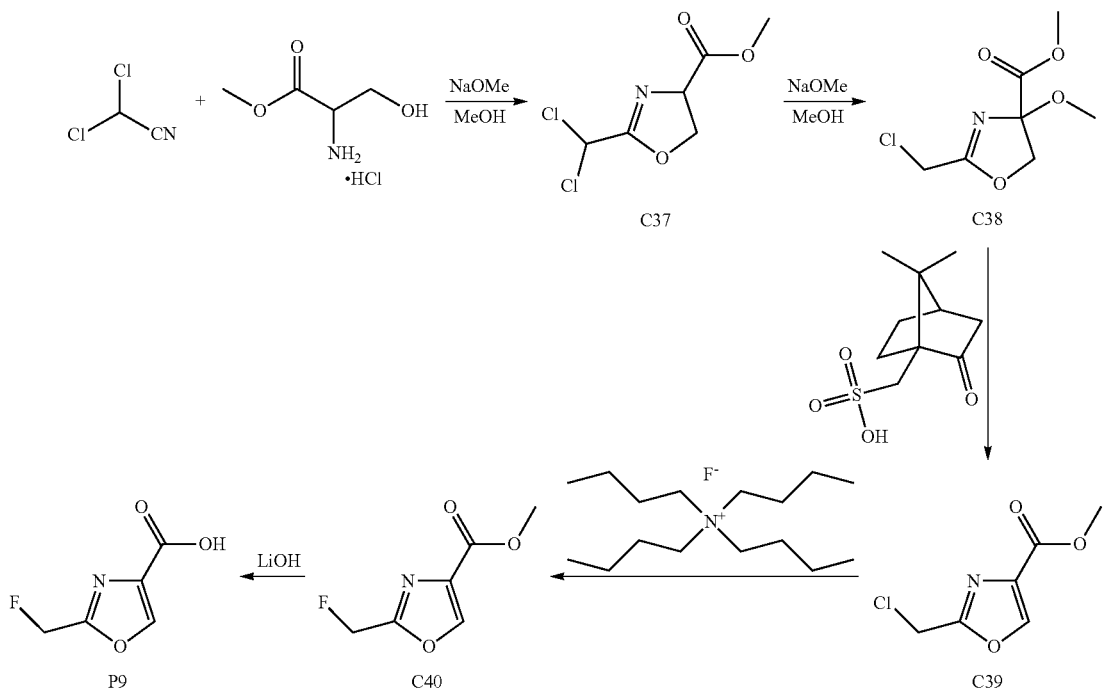

Step 1. Synthesis of methyl 2-(dichloromethyl)-4,5-dihydro-1,3-oxazole-4-carboxylate (C37)

A solution of dichloroacetonitrile (215 g, 1.96 mol) in methanol (200 mL) was added drop-wise to a −5° C. solution of sodium methoxide (15.4 g, 0.285 mol) in methanol (500 mL). A solution of methyl 2-amino-3-hydroxypropanoate, hydrochloride salt (382 g, 2.45 mol) in methanol (300 mL) was then added to the −5° C. reaction mixture, which was subsequently allowed to stir at room temperature for 16 hours. Dichloromethane (1 L) and water (800 mL) were added, and the aqueous layer was extracted with dichloromethane (1 L); the combined organic layers were concentrated in vacuo to provide the product as a yellow oil, which was used in the next step without further purification. Yield: 300 g, 1.4 mol, 71%. $^1$H NMR (400 MHz, CDCl$_3$) δ 6.29 (s, 1H), 4.90 (dd, J=10.8, 8.3 Hz, 1H), 4.74 (dd, J=8.8, 8.3 Hz, 1H), 4.66 (dd, J=10.8, 8.9 Hz, 1H), 3.82 (s, 3H).

Step 2. Synthesis of methyl 2-(chloromethyl)-4-methoxy-4,5-dihydro-1,3-oxazole-4-carboxylate (C38)

A solution of C37 (205 g, 0.967 mol) in methanol (700 mL) was added drop-wise to a cooled solution of sodium methoxide (52.2 g, 0.966 mol) in methanol (300 mL), at a rate sufficient to maintain the reaction temperature below 10° C. The reaction mixture was then stirred at room temperature for 16 hours, whereupon it was diluted with dichloromethane (1 L) and water (800 mL). The aqueous layer was extracted with dichloromethane (2×500 mL), and the combined organic layers were concentrated in vacuo to afford the product as a yellow oil. This material was used in the next step without additional purification. Yield: 200 g, 0.96 mol, 99%.

Step 3. Synthesis of methyl 2-(chloromethyl)-1,3-oxazole-4-carboxylate (C39)

(7,7-Dimethyl-2-oxobicyclo[2.2.1]hept-1-yl)methanesulfonic acid (camphor-sulfonic acid, 45.9 g, 0.198 mol) was added to a solution of C38 (193 g, 0.930 mol) in toluene (700 mL), and the reaction mixture was heated at 70° C. for 1 hour. Water (1 L) was added, and the mixture was extracted with ethyl acetate (2×1 L); the combined organic layers were sequentially washed with aqueous potassium carbonate solution (10%, 500 mL), water (800 mL), and saturated aqueous sodium chloride solution (0.8 L), dried, and concentrated in vacuo. Silica gel chromatography (Gradient: 5% to 25% ethyl acetate in petroleum ether) provided the product as a white solid. Yield: 55 g, 0.31 mol, 33%. $^1$H NMR (400 MHz, CDCl$_3$) δ 8.26 (s, 1H), 4.65 (s, 2H), 3.93 (s, 3H).

Step 4. Synthesis of methyl 2-(fluoromethyl)-1,3-oxazole-4-carboxylate (C40)

To a suspension of C39 (40 g, 0.23 mol) in acetonitrile (1 L) was added tetrabutylammonium fluoride (357 g, 1.36 mol), and the reaction mixture was stirred at 25° C. for 16 hours. After removal of solvent in vacuo, the residue was diluted with water (1 L) and extracted with ethyl acetate (4×1 L). The combined organic layers were dried over sodium sulfate, filtered, and concentrated under reduced pressure. Chromatography on silica gel (Gradient: 17% to 23% ethyl acetate in petroleum ether) afforded the product as a yellow solid. Yield: 8.7 g, 55 mmol, 24%. $^1$H NMR (400 MHz, CDCl$_3$) δ 8.31 (d, J=1.2 Hz, 1H), 5.43 (d, J$_{HF}$=47.2 Hz, 2H), 3.94 (s, 3H).

Step 5. Synthesis of 2-(fluoromethyl)-1,3-oxazole-4-carboxylic acid (P9)

To a solution of C40 (18 g, 110 mmol) in tetrahydrofuran (150 mL) was added a solution of lithium hydroxide (5.42 g, 226 mmol) in a mixture of methanol and water (1:1, 500 mL). The reaction mixture was stirred at room temperature for 1 hour, whereupon it was concentrated in vacuo. After the residue had been dissolved in water (500 mL), it was acidified by addition of 2 M aqueous hydrochloric acid until it reached a pH of 2. The aqueous layer was then extracted with ethyl acetate (2×100 mL), and the combined organic layers were dried over sodium sulfate, filtered, and concentrated under reduced pressure, providing the product as a yellow solid. Yield: 13 g, 90 mmol, 82%. LCMS m/z 144.0 [M–H$^+$]. $^1$H NMR (400 MHz, CD$_3$OD) δ 8.61 (s, 1H), 5.47 (d, J$_{HF}$=47 Hz, 2H).

Preparation P10

5-(But-2-yn-1-yloxy)pyridine-2-carboxylic acid (P10)

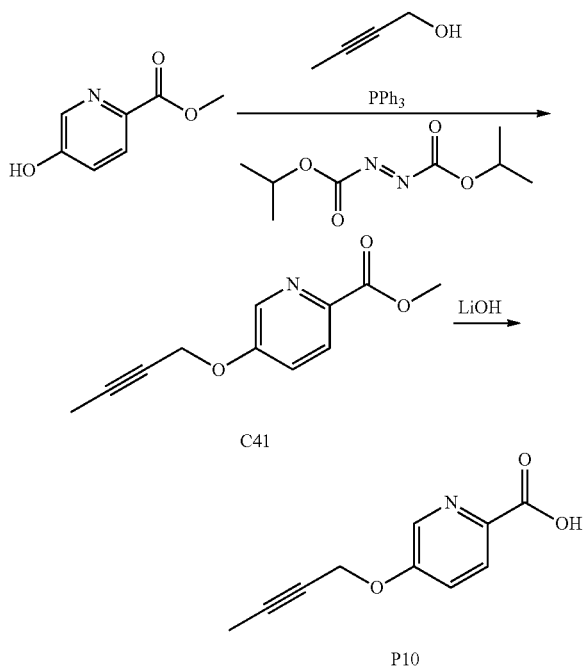

Step 1. Synthesis of methyl 5-(but-2-yn-1-yloxy)pyridine-2-carboxylate (C41)

To a 0° C. solution of but-2-yn-1-ol (0.645 mL, 8.62 mmol) in tetrahydrofuran (30 mL) were added methyl 5-hydroxypyridine-2-carboxylate (1.30 g, 8.49 mmol), triphenylphosphine (3.34 g, 12.7 mmol), and diisopropyl azodicarboxylate (2.50 mL, 12.7 mmol). The reaction mixture was then warmed to room temperature (18° C.) and stirred for 48 hours, whereupon it was concentrated in vacuo. Silica gel chromatography (Gradient: 15% to 50% ethyl acetate in petroleum ether) afforded the product as a yellow solid. Yield: 1.1 g, 5.4 mmol, 64%. $^1$H NMR (400 MHz, CDCl$_3$) δ 8.46 (d, J=2.9 Hz, 1H), 8.13 (d, J=8.8 Hz, 1H), 7.37 (dd, J=8.8, 2.9 Hz, 1H), 4.77 (q, J=2.3 Hz, 2H), 3.99 (s, 3H), 1.86 (t, J=2.3 Hz, 3H).

Step 2. Synthesis of 5-(but-2-yn-1-yloxy)pyridine-2-carboxylic acid (P10)

A solution of lithium hydroxide monohydrate (975 mg, 23.2 mmol) in water (7 mL) was added drop-wise to a room temperature (15° C.) solution of C41 (1.59 g, 7.75 mmol) in tetrahydrofuran (20 mL), and the reaction mixture was stirred at room temperature for 1 hour. It was then acidified to pH 2 via addition of 2 M aqueous hydrochloric acid, and extracted with ethyl acetate (2×100 mL). The combined organic layers were washed with saturated aqueous sodium chloride solution (2×100 mL), dried over sodium sulfate, filtered, and concentrated under reduced pressure to provide the product as a yellow solid. Yield: 1.0 g, 5.2 mmol, 67%. LCMS m/z 192.1 [M+H]$^+$. $^1$H NMR (400 MHz, CD$_3$OD) δ 8.35 (d, J=2.9 Hz, 1H), 8.14 (d, J=8.7 Hz, 1H), 7.57 (dd, J=8.7, 2.8 Hz, 1H), 4.87 (q, J=2.3 Hz, 2H), 1.84 (t, J=2.3 Hz, 3H).

Example 1

N-{2-[(5S)-3-Amino-2,5-di methyl-1,1-dioxido-5,6-dihydro-2H-1,2,4-thiadiazin-5-yl]-1,3-thiazol-4-yl}-5-(difluoromethoxy)pyridine-2-carboxamide (1)

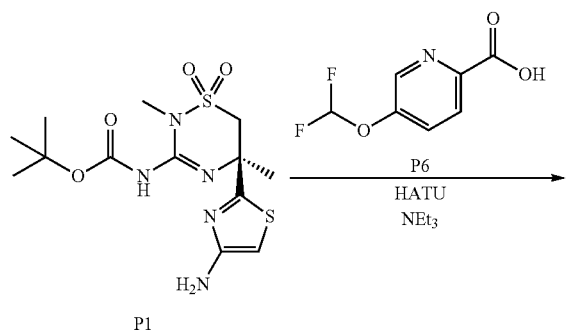

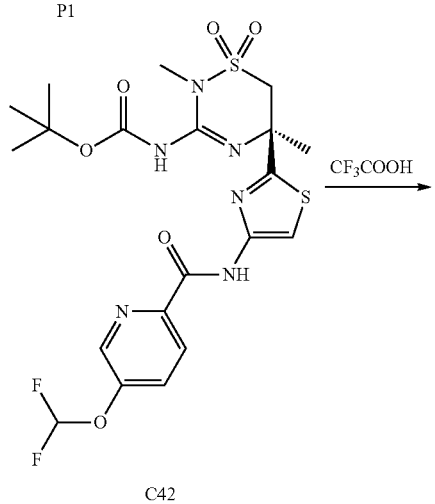

Step 1. Synthesis of tert-butyl {(5S)-5-[4-({[5-(difluoromethoxy)pyridin-2-yl]carbonyl}amino)-1,3-thiazol-2-yl]-2,5-dimethyl-1,1-dioxido-5,6-dihydro-2H-1,2,4-thiadiazin-3-yl}carbamate (C42)

Triethylamine (36.4 μL, 0.261 mmol) and O-(7-azabenzotriazol-1-yl)-N,N,N',N'-tetramethyluronium hexafluorophosphate (HATU; 72.9 mg, 0.192 mmol) were added to a solution of P1 (100 mg, 0.266 mmol) and P6 (36.3 mg, 0.192 mmol) in dichloromethane (3.5 mL), and the reaction mixture was stirred at room temperature for 1 hour. After being diluted with dichloromethane, it was washed sequentially with water and with saturated aqueous sodium chloride solution, dried over sodium sulfate, filtered, and concentrated in vacuo. Silica gel chromatography (Gradient: 0% to 50% ethyl acetate in heptane) afforded the product as a white solid. Yield: 88.7 mg, 0.162 mmol, 84%. LCMS m/z 547.3 [M+H]$^+$. $^1$H NMR (400 MHz, CD$_3$OD) δ 8.56 (dd, J=2.7, 0.4 Hz, 1H), 8.27 (dd, J=8.7, 0.5 Hz, 1H), 7.81 (br dd, J=8.7, 2.7 Hz, 1H), 7.78 (s, 1H), 7.08 (t, $J_{HF}$=72.6 Hz, 1H), 4.58 (d, J=13.9 Hz, 1H), 4.17 (d, J=14.0 Hz, 1H), 3.19 (s, 3H), 1.92 (s, 3H), 1.52 (s, 9H).

Step 2. Synthesis of N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (1)

A solution of C42 (88.7 mg, 0.162 mmol) in dichloromethane (2.7 mL) was treated with trifluoroacetic acid (0.249 mL, 3.23 mmol), and the reaction mixture was stirred at room temperature for 1 hour. It was then diluted with dichloromethane, washed sequentially with saturated aqueous sodium bicarbonate solution and with saturated aqueous sodium chloride solution, dried over sodium sulfate, filtered, and concentrated. Purification via chromatography on silica gel (Gradient: 0% to 10% methanol in dichloromethane) provided the product as a white solid. Yield: 67 mg, 0.15 mmol, 93%. LCMS m/z 447.2 [M+H]$^+$. $^1$H NMR (400 MHz, CD$_3$OD) δ 8.56 (br dd, J=2.7, 0.5 Hz, 1H), 8.27 (dd, J=8.7, 0.6 Hz, 1H), 7.81 (ddt, J=8.6, 2.7, 0.6 Hz, 1H), 7.64 (s, 1H), 7.08 (t, $J_{HF}$=72.6 Hz, 1H), 4.16 (d, J=13.8 Hz, 1H), 3.76 (d, J=13.8 Hz, 1H), 3.19 (s, 3H), 1.70 (s, 3H).

Example 2

N-{2-[(5S)-3-Amino-2,5-dimethyl-1,1-dioxido-5,6-dihydro-2H-1,2,4-thiadiazin-5-yl]-1,3-thiazol-4-yl}-1-(difluoromethyl)-1H-pyrazole-3-carboxamide (2)

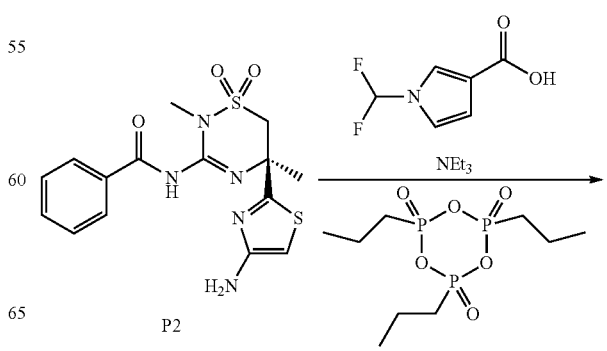

acetate; 157 μL, 0.264 mmol) were added, and the reaction mixture was stirred for 2.5 hours at 0° C. It was then partitioned between saturated aqueous sodium bicarbonate solution (7 mL) and ethyl acetate (7 mL); the aqueous layer was extracted with ethyl acetate (3×7 mL), and the combined organic layers were dried over sodium sulfate, filtered, and concentrated in vacuo. Silica gel chromatography (Gradient: 0% to 100% ethyl acetate in heptane) provided the product as an off-white solid. Yield: 25.8 mg, 49.3 μmol, 38%. $^1$H NMR (400 MHz, CDCl$_3$) δ 12.52-12.26 (br s, 1H), 9.39 (br s, 1H), 8.25 (br d, J=8.2 Hz, 2H), 7.91 (d, J=2.6 Hz, 1H), 7.74 (s, 1H), 7.56 (br dd, J=7, 7 Hz, 1H), 7.46 (br dd, J=7.6, 7.5 Hz, 2H), 7.23 (t, $J_{HF}$=60.4 Hz, 1H), 7.08 (d, J=2 Hz, 1H), 4.44 (d, J=13.8 Hz, 1H), 3.75 (d, J=13.8 Hz, 1H), 3.48 (s, 3H), 2.00 (s, 3H).

Step 2. Synthesis of N-{2-[(5S)-3-amino-2,5-dimethyl-1,1-dioxido-5,6-dihydro-2H-1,2,4-thiadiazin-5-yl]-1,3-thiazol-4-yl}-1-(difluoromethyl)-1H-pyrazole-3-carboxamide (2)

A suspension of C43 (25.8 mg, 49.3 μmol) and 1,8-diazabicyclo[5.4.0]undec-7-ene (2 drops) in methanol (1 mL) was heated to 60° C. overnight, whereupon it was allowed to cool to room temperature and was concentrated in vacuo. Chromatography on silica gel (Gradient: 40% to 100% ethyl acetate in heptane) afforded the product as a white solid. Yield: 10.6 mg, 25.3 μmol, 51%. LCMS m/z 420.1 [M+H]$^+$. $^1$H NMR (400 MHz, CDCl$_3$) δ 9.34 (br s, 1H), 7.90 (d, J=2.7 Hz, 1H), 7.65 (s, 1H), 7.23 (t, $J_{HF}$=60.5 Hz, 1H), 7.07 (d, J=2.7 Hz, 1H), 4.12 (d, J=14.0 Hz, 1H), 3.71 (d, J=14.0 Hz, 1H), 3.31 (s, 3H), 1.81 (s, 3H).

Examples 3, 4, and 5

N-{2-[(5R,6S)-3-Amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (3), N-{2-[(5S,6R)-3-Amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (4), and N-{2-[(5S,6S)-3-Amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (5)

Step 1. Synthesis of N-{2-[(5S)-3-(benzoylamino)-2,5-dimethyl-1,1-dioxido-5,6-dihydro-2H-1,2,4-thiadiazin-5-yl]-1,3-thiazol-4-yl}-1-(difluoromethyl)-1H-pyrazole-3-carboxamide (C43)

A mixture of P2 (50 mg, 0.13 mmol) and 1-(difluoromethyl)-1H-pyrazole-3-carboxylic acid (25.6 mg, 0.158 mmol) in ethyl acetate (1 mL) was cooled to 0° C. Triethylamine (73 μL, 0.52 mmol) and 2,4,6-tripropyl-1,3,5,2,4,6-trioxatriphosphinane 2,4,6-trioxide (50% solution in ethyl

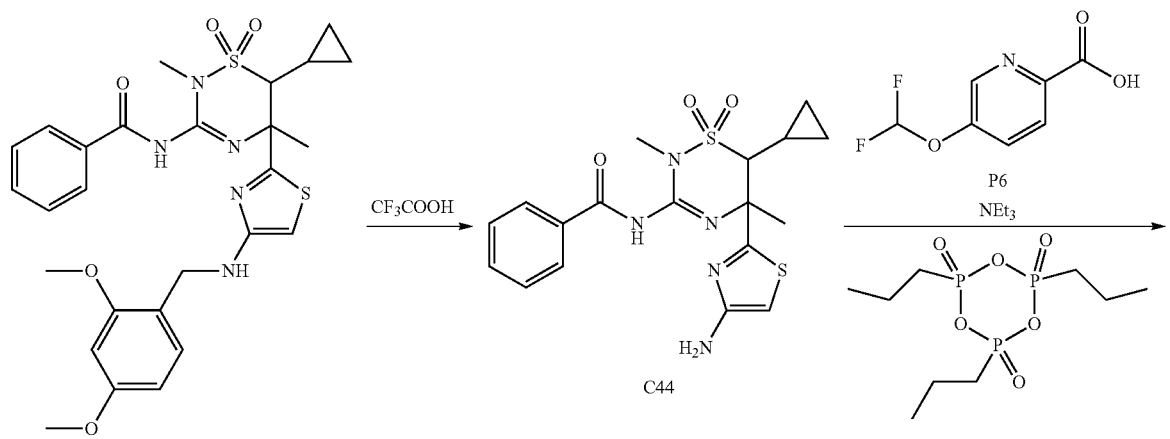

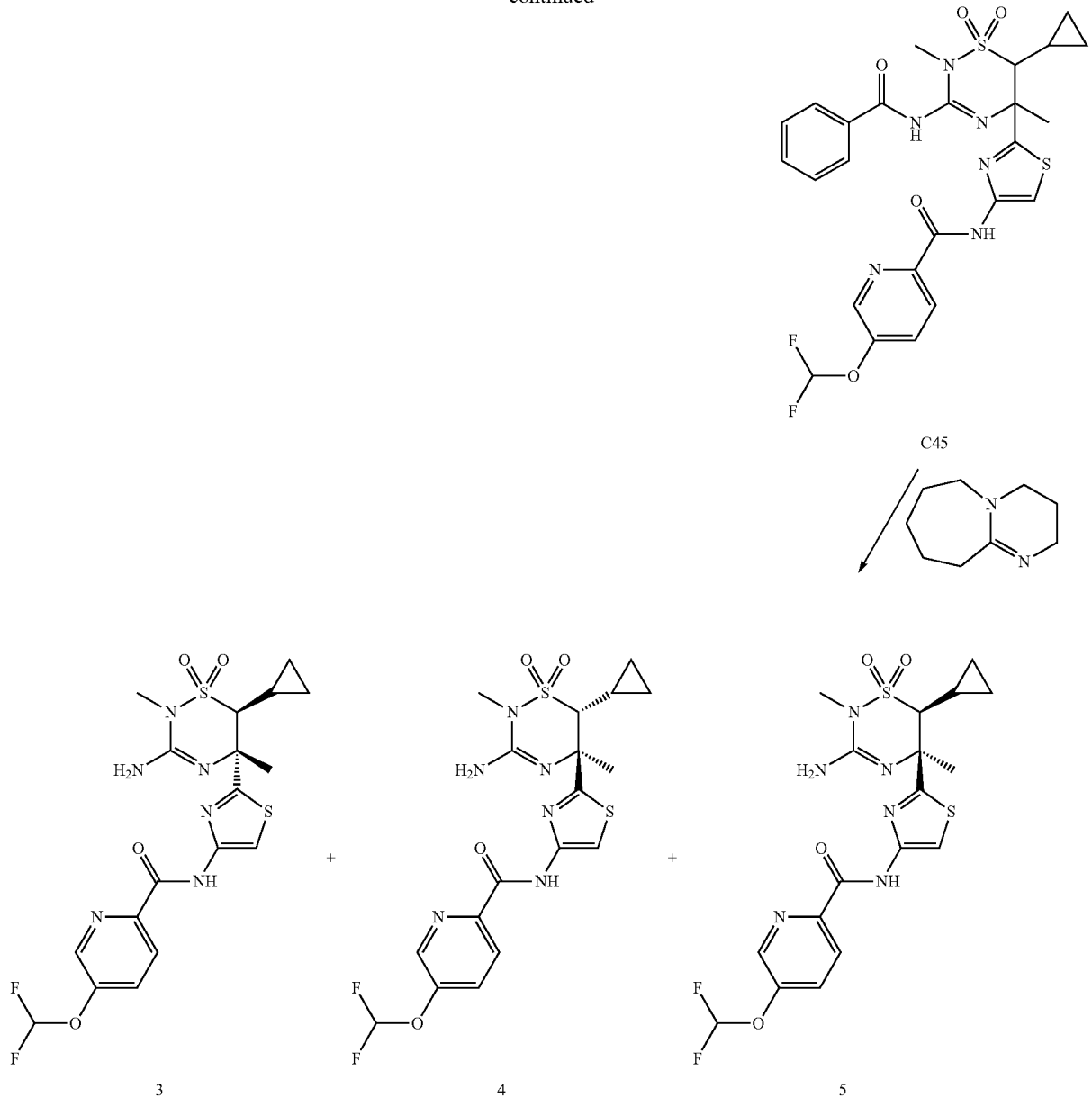

Step 1. Synthesis of N-[5-(4-amino-1,3-thiazol-2-yl)-6-cyclopropyl-2,5-dimethyl-1,1-dioxido-5,6-dihydro-2H-1,2,4-thiadiazin-3-yl]benzamide (C44)

Trifluoroacetic acid (0.7 mL) was added in a drop-wise manner to a 0° C. solution of P3 (0.288 g, 0.506 mmol) in dichloromethane (5 mL). The reaction mixture was stirred at 0° C. for 1 hour, whereupon it was partitioned between dichloromethane (100 mL) and saturated aqueous sodium bicarbonate solution (200 mL). The aqueous layer was extracted with dichloromethane (2×50 mL), and the combined organic layers were dried over sodium sulfate, filtered, and concentrated in vacuo to provide the product as an orange solid (0.25 g). This material was taken directly to the following step. LCMS showed two close-running peaks of similar size, both with m/z 420.4 [M+H]$^+$.

Step 2. Synthesis of N-{2-[3-(benzoylamino)-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (C45)

A solution of C44 (from the previous step, 0.25 g, ≤0.506 mmol) and P6 (0.135 g, 0.714 mmol) in ethyl acetate (5 mL) was cooled to 0° C. and treated with triethylamine (0.332 mL, 2.38 mmol). 2,4,6-Tripropyl-1,3,5,2,4,6-trioxatriphosphinane 2,4,6-trioxide (50% solution in ethyl acetate; 0.709 mL, 1.19 mmol) was added, and stirring was continued for 2 hours at 0° C. LCMS analysis at this point revealed two close-running peaks in an approximately 1:1 ratio, both with m/z 591.3 [M+H]$^+$. Saturated aqueous sodium bicarbonate solution (50 mL) was added, and the resulting mixture was extracted with ethyl acetate (3×50 mL). The combined organic layers were dried over sodium sulfate, filtered, and concentrated in vacuo; the residue was adsorbed onto silica gel as a solution in dichloromethane and subjected to silica gel chromatography (Gradient: 0% to 100% ethyl acetate in heptane). The product was isolated as a white solid, which by $^1$H NMR analysis consisted of an approximately 1:1 mixture of diastereomers. Yield: 232 mg, 0.393 mmol, 78% over 2 steps. $^1$H NMR (400 MHz, CDCl$_3$), characteristic peaks: δ [10.43 (br s) and 10.40 (br s), total 1H], [8.50 (br d, J=2.6 Hz) and 8.47 (br d, J=2.4 Hz), total 1H], 8.34-8.30 (m, 1H), 8.28-8.20 (m, 2H), [7.84 (s) and 7.83 (s), total 1H], 7.70-7.66 (m, 1H), 7.58-7.51 (m, 1H), 7.49-7.42 (m, 2H), [6.66 (t, J$_{HF}$=71.9 Hz) and 6.65 (t, J$_{HF}$=71.8 Hz), total 1H], [3.56 (d, J=10.9 Hz) and 2.98 (d, J=10.9 Hz), total 1H], [3.52 (s) and 3.48 (s), total 3H], [2.13 (s) and 2.09 (s), total 3H].

Step 3. Synthesis of N-{2-[(5R,6S)-3-amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (3), N-{2-[(5S,6R)-3-amino-6-cyclopropyl-2, 5-dimethyl-1,1-dioxido-5,6-dihydro-2H-1,2,4-thiadiazin-5-yl]-1,3-thiazol-4-yl}-5-(difluoromethoxy)pyridine-2-carboxamide (4), and N-{2-[(5S,6S)-3-amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (5)

To a solution of C45 (232 mg, 0.393 mmol) in methanol (10 mL) was added 1,8-diazabicyclo[5.4.0]undec-7-ene (59.3 μL, 0.396 mmol), and the reaction mixture was heated to 60° C. for 16 hours. Solvent was removed in vacuo, and the residue was adsorbed onto silica gel as a solution in dichloromethane; silica gel chromatography (Gradient: 20% to 100% ethyl acetate in heptane) provided the products (138 mg, 0.284 mmol, 72% yield). The mixed fractions from the column (115 mg, 0.236 mmol) were subjected to supercritical fluid chromatography (Column: Phenomenex Lux Cellulose-2, 5 μm; Mobile phase A: carbon dioxide; Mobile phase B: 1:1 acetonitrile/methanol; Gradient: 5% to 60% B) to separate the individual enantiomers and diastereomers. Each of the three samples isolated was then individually chromatographed on silica gel (Gradient: 0% to 10% methanol in dichloromethane) to afford the following, all of which were obtained as white solids.

The first-eluting isomer from the supercritical fluid chromatography provided 3. Yield: 7.4 mg, 15 μmol, 4%. LCMS m/z 487.3 [M+H]$^+$. $^1$H NMR (400 MHz, CDCl$_3$) δ 10.38 (br s, 1H), 8.47 (br s, 1H), 8.31 (d, J=8.6 Hz, 1H), 7.71 (s, 1H), 7.67 (br d, J=8.6 Hz, 1H), 6.65 (t, J$_{HF}$=72.1 Hz, 1H), 3.37 (d, J=11.0 Hz, 1H), 3.29 (s, 3H), 1.85 (s, 3H), 1.10-0.99 (m, 1H), 0.95-0.69 (m, 3H), 0.27-0.18 (m, 1H).

The second-eluting isomer from the supercritical fluid chromatography provided 4. Yield: 39.9 mg, 82.0 μmol, 21%. LCMS m/z 487.3 [M+H]$^+$. $^1$H NMR (400 MHz, CDCl$_3$) δ 10.38 (br s, 1H), 8.47 (br d, J=2.4 Hz, 1H), 8.31 (br d, J=8.6 Hz, 1H), 7.73 (s, 1H), 7.67 (br dd, J=8.6, 2.7 Hz, 1H), 6.65 (t, J$_{HF}$=72.0, 1H), 3.45 (d, J=10.8 Hz, 1H), 3.31 (s, 3H), 1.91 (s, 3H), 1.12-1.00 (m, 1H), 0.96-0.85 (m, 1H), 0.85-0.72 (m, 2H), 0.29-0.19 (m, 1H).

The third-eluting isomer from the supercritical fluid chromatography was obtained in a quantity too small to characterize.

The fourth-eluting isomer from the supercritical fluid chromatography provided 5. Yield: 20.2 mg, 41.5 μmol, 11%. LCMS m/z 487.3 [M+H]$^+$. $^1$H NMR (400 MHz, CDCl$_3$) δ 10.38 (br s, 1H), 8.49 (br d, J=2.3 Hz, 1H), 8.32 (br d, J=8.6 Hz, 1H), 7.74 (s, 1H), 7.68 (br dd, J=8.6, 2.7 Hz, 1H), 6.65 (t, J$_{HF}$=72.0 Hz, 1H), 3.29 (s, 3H), 2.91 (d, J=10.9 Hz, 1H), 1.92 (s, 3H), 1.36-1.23 (m, 1H), 0.85-0.69 (m, 2H), 0.62-0.52 (m, 1H), 0.30-0.21 (m, 1H).

The indicated relative and absolute stereochemistries for these compounds were assigned on the basis of NMR work and biological activity. From the $^1$H NMR spectra, 3 and 4 are enantiomers of one another. NOE studies revealed that irradiation of the quaternary methyl group of both 3 and 4 resulted in enhancement of the methine proton of the cyclopropyl group, while irradiation of the methine adjacent to the sulfonyl group in 5 provided a substantial enhancement in the signal for the quaternary methyl group; these results established the relative stereochemistry of the cyclopropyl and methyl groups. The potency difference between 3 and 4, in relation to the potency of 9 (see Table 7), indicated that 4 has the same absolute stereochemistry at the quaternary center as does 9 (see X-ray structure determination on 9 below).

Examples 6, 7, and 8

N-[2-(3-Amino-2,5,6,6-tetramethyl-1,1-dioxido-5,6-dihydro-2H-1,2,4-thiadiazin-5-yl)-1,3-thiazol-4-yl]-5-(difluoromethoxy)pyridine-2-carboxamide (6), N-{2-[(5R)-3-amino-2,5,6,6-tetramethyl-1,1-dioxido-5,6-dihydro-2H-1,2,4-thiadiazin-5-yl]-1,3-thiazol-4-yl}-5-(difluoromethoxy)pyridine-2-carboxamide (7), and N-{2-[(5S)-3-amino-2,5,6,6-tetramethyl-1,1-dioxido-5,6-dihydro-2H-1,2,4-thiadiazin-5-yl]-1,3-thiazol-4-yl}-5-(difluoromethoxy)pyridine-2-carboxamide (8)

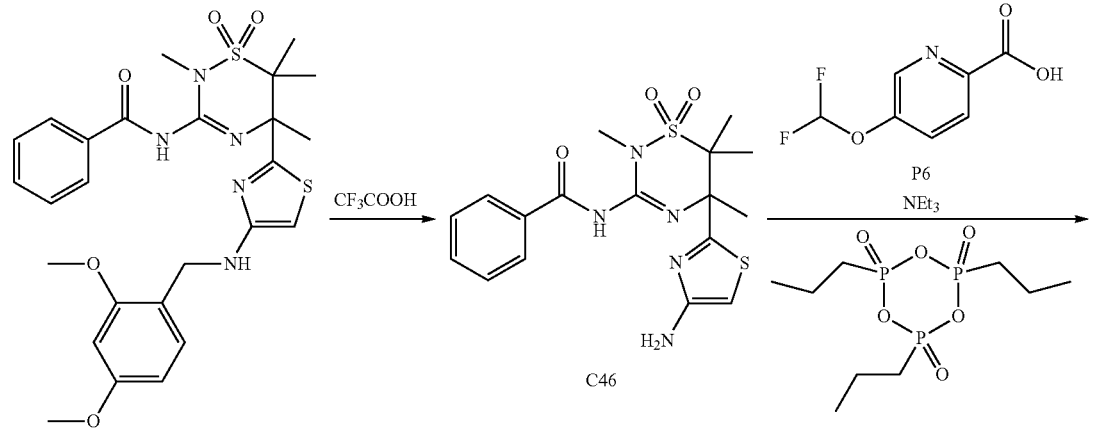

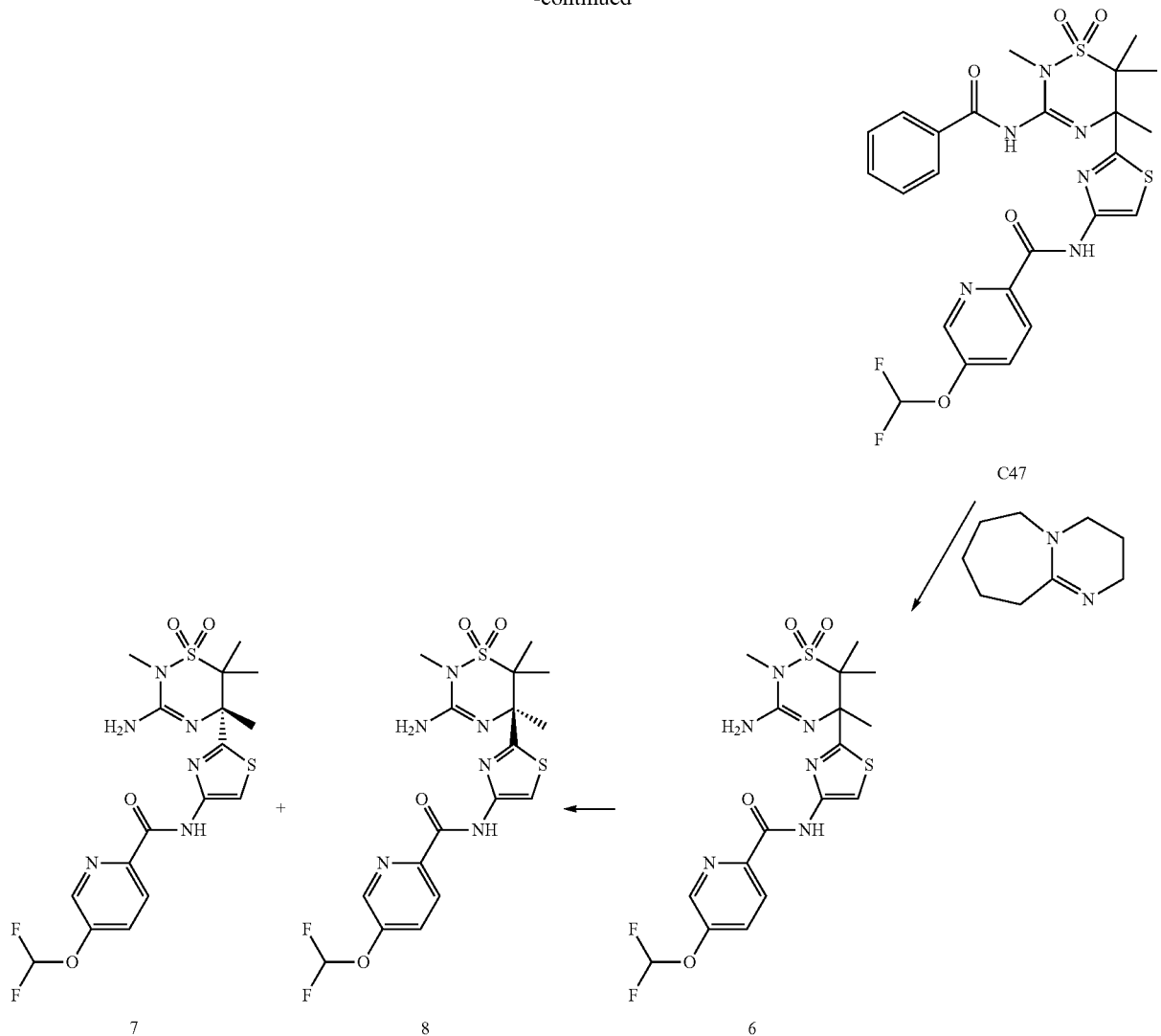

Step 1. Synthesis of N-[5-(4-amino-1,3-thiazol-2-yl)-2,5,6,6-tetramethyl-1,1-dioxido-5,6-dihydro-2H-1,2,4-thiadiazin-3-yl]benzamide (C46)

Conversion of P4 to C46 was carried out using the method described for synthesis of C44 from P3 in Examples 3, 4, and 5. The product was obtained as an orange solid, which was used directly in the following step. LCMS m/z 408.2 [M+H]$^+$.

Step 2. Synthesis of N-{2-[3-(benzoylamino)-2,5,6,6-tetramethyl-1,1-dioxido-5,6-dihydro-2H-1,2,4-thiadiazin-5-yl]-1,3-thiazol-4-yl}-5-(difluoromethoxy)pyridine-2-carboxamide (C47)

Reaction of C46 with P6 was effected using the procedure described for synthesis of C45 from C44 in Examples 3, 4, and 5. The product was isolated as a white solid. Yield: 80 mg, 0.14 mmol, 58%. $^1$H NMR (400 MHz, CDCl$_3$) δ 12.45 (br s, 1H), 10.44 (br s, 1H), 8.51 (br d, J=2.6 Hz, 1H), 8.33 (dd, J=8.6, 0.6 Hz, 1H), 8.29-8.25 (m, 2H), 7.83 (s, 1H), 7.69 (br dd, J=8.7, 2.7 Hz, 1H), 7.57-7.52 (m, 1H), 7.49-7.43 (m, 2H), 6.66 (t, $J_{HF}$=71.9 Hz, 1H), 3.54 (s, 3H), 2.07 (s, 3H), 1.85 (s, 3H), 1.52 (s, 3H).

Step 3. Synthesis of N-[2-(3-amino-2,5,6,6-tetramethyl-1,1-dioxido-5,6-dihydro-2H-1,2,4-thiadiazin-5-yl)-1,3-thiazol-4-yl]-5-(difluoromethoxy)pyridine-2-carboxamide (6)

1,8-Diazabicyclo[5.4.0]undec-7-ene (20.9 μL, 0.140 mmol) was added to a solution of C47 (80 mg, 0.14 mmol) in methanol (5 mL). The reaction mixture was heated to 60° C. for 10 hours, whereupon it was concentrated in vacuo and adsorbed onto silica gel as a solution in dichloromethane. Silica gel chromatography (Gradient: 20% to 100% ethyl acetate in heptane) afforded the product as a white solid. Yield: 57 mg, 0.12 mmol, 86%. LCMS m/z 475.3 [M+H]$^+$. $^1$H NMR (400 MHz, CDCl$_3$) δ 10.36 (br s, 1H), 8.50 (br d, J=2.7 Hz, 1H), 8.32 (dd, J=8.6, 0.6 Hz, 1H), 7.69 (s, 1H), 7.68 (br dd, J=8.6, 2.6 Hz, 1H), 6.66 (t, $J_{HF}$=72.0 Hz, 1H), 4.22-4.07 (br s, 2H), 3.29 (s, 3H), 1.95 (s, 3H), 1.85 (s, 3H), 1.17 (s, 3H).

Step 4. Isolation of N-{2-[(5R)-3-amino-2,5,6,6-tetramethyl-1,1-dioxido-5,6-dihydro-2H-1,2,4-thiadiazin-5-yl]-1,3-thiazol-4-yl}-5-(difluoromethoxy)pyridine-2-carboxamide (7) and N-{2-[(5S)-3-amino-2,5,6,6-tetramethyl-1,1-dioxido-5,6-dihydro-2H-1, 2,4-thiadiazin-5-yl]-1,3-thiazol-4-yl}-5-(difluoromethoxy)pyridine-2-carboxamide (8)

Separation of 6 (57 mg) into its component enantiomers was effected via supercritical fluid chromatography (Column: Phenomenex Lux Cellulose-2, 5 μm; Mobile phase A: carbon dioxide; Mobile phase B: 1:1 acetonitrile/methanol; Gradient: 5% to 60% B). Each enantiomer was then repurified using silica gel chromatography (Gradient: 0% to 10% methanol in dichloromethane). The first-eluting enantiomer from the supercritical fluid chromatography was obtained as a white solid after silica gel chromatography, and was assigned as 7. Yield: 6.3 mg, 11% for the separation. LCMS m/z 475.3 [M+H]$^+$. $^1$H NMR (400 MHz, CDCl$_3$) δ 10.37 (br s, 1H), 8.50 (d, J=2.6 Hz, 1H), 8.32 (d, J=8.6 Hz, 1H), 7.74 (s, 1H), 7.70-7.66 (m, 1H), 6.66 (t, J$_{HF}$=71.9 Hz, 1H), 3.35 (s, 3H), 1.92 (s, 3H), 1.90 (s, 3H), 1.27 (br s, 3H).

The second-eluting enantiomer from the supercritical fluid chromatography was also obtained as a white solid after silica gel chromatography, and was assigned as 8. Yield: 15 mg, 26% for the separation. LCMS m/z 475.3 [M+H]$^+$. $^1$H NMR (400 MHz, CDCl$_3$) δ 10.36 (br s, 1H), 8.50 (s, 1H), 8.32 (d, J=8.6 Hz, 1H), 7.71 (s, 1H), 7.70-7.65 (m, 1H), 6.65 (t, J$_{HF}$=71.9 Hz, 1H), 3.32 (s, 3H), 1.93 (s, 3H), 1.87 (s, 3H), 1.21 (s, 3H).

The indicated absolute stereochemistries of 7 and 8 were assigned on the basis of the difference in the biological activity of these two compounds (see Table 7), in analogy with the stereochemistries of 3 and 4.

Example 9

N-{2-[(5S)-3-Amino-2,5-dimethyl-1,1-dioxido-5,6-dihydro-2H-1,2,4-thiadiazin-5-yl]-1,3-thiazol-4-yl}-5-(difluoromethoxy)-3-methylpyridine-2-carboxamide, methanesulfonic acid salt (9)

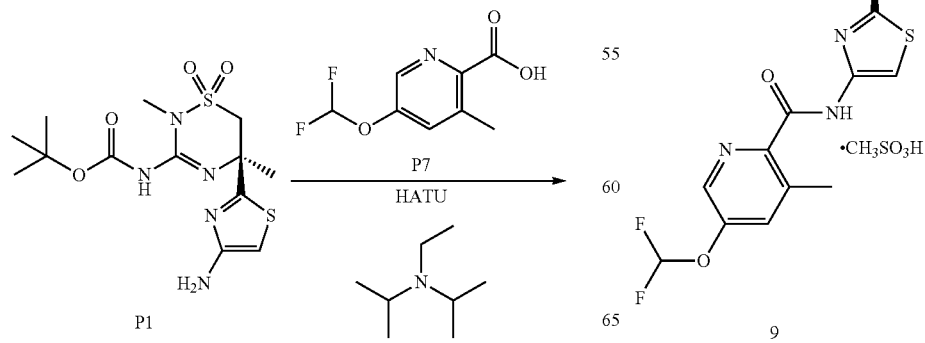

Step 1. Synthesis of tert-butyl {(5S)-5-[4-({[5-(difluoromethoxy)-3-methylpyridin-2-yl]carbonyl}amino)-1,3-thiazol-2-yl]-2,5-dimethyl-1,1-dioxido-5,6-dihydro-2H-1,2,4-thiadiazin-3-yl}carbamate (C48)

A mixture of P1 (31.30 g, 83.36 mmol), P7 (30.5 g, 150 mmol), O-(7-azabenzotriazol-1-yl)-N,N,N',N'-tetramethyluronium hexafluorophosphate (76.1 g, 200 mmol), and N,N-diisopropylethylamine (116 mL, 666 mmol) in dichloromethane (1.7 L) was stirred at room temperature for 30 minutes. The reaction mixture was then diluted with dichloromethane, washed sequentially with aqueous 5% citric acid solution, saturated aqueous sodium bicarbonate solution, and saturated aqueous sodium chloride solution, dried over sodium sulfate, filtered, and concentrated in vacuo. Chromatography on silica gel (Gradient: 0% to 100% ethyl acetate in heptane) afforded the product as a pale yellow solid. Yield: 36.57 g, 65.23 mmol, 78%. LCMS m/z 559.3 [M−H$^+$]. $^1$H NMR (400 MHz, CD$_3$OD) δ 8.39-8.37 (m, 1H), 7.74 (s, 1H), 7.60-7.58 (m, 1H), 7.06 (t, $J_{HF}$=72.8 Hz, 1H), 4.56 (d, J=13.9 Hz, 1H), 4.16 (d, J=14.0 Hz, 1H), 3.19 (s, 3H), 2.75 (s, 3H), 1.91 (br s, 3H), 1.52 (s, 9H).

Step 2. Synthesis of N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)-3-methylpyridine-2-carboxamide (C49)

Trifluoroacetic acid (100 mL) was added to a solution of C48 (36.57 g, 65.23 mmol) in dichloromethane (1.1 L). The reaction mixture was stirred at room temperature for 45 minutes, whereupon it was basified by addition of 1 M aqueous sodium hydroxide solution. The aqueous layer was extracted twice with dichloromethane, and the combined organic layers were washed with saturated aqueous sodium chloride solution, dried over sodium sulfate, filtered and concentrated under reduced pressure. Silica gel chromatography (Gradient: 0% to 5% methanol in dichloromethane) provided an off-white solid, which was triturated in heptane containing a small amount of diethyl ether for approximately 30 minutes to afford the product as a white solid. Yield: 26.08 g, 56.64 mmol, 87%. LCMS m/z 461.3 [M+H]$^+$. $^1$H NMR (400 MHz, CD$_3$OD) δ 8.38 (br d, J=2.5 Hz, 1H), 7.60 (s, 1H), 7.58 (br d, J=2.5 Hz, 1H), 7.05 (t, $J_{HF}$=72.8 Hz, 1H), 4.15 (d, J=13.7 Hz, 1H), 3.75 (d, J=13.8 Hz, 1H), 3.19 (s, 3H), 2.75 (s, 3H), 1.70 (s, 3H).

Step 3. Synthesis of N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)-3-methylpyridine-2-carboxamide, methanesulfonic acid salt (9)

A mixture of C49 (32.62 g, 70.84 mmol) in methanol (316 mL) was filtered through cotton, and then treated with a solution of methanesulfonic acid (4.60 mL, 70.9 mmol) in methanol (38 mL). The resulting mixture was stirred for 1 hour, whereupon it was concentrated on a rotary evaporator until it became a very thick slurry. At this point, diethyl ether (400 mL) was added, and the mixture was stirred for 10 minutes and filtered. The filter cake was thoroughly washed with diethyl ether, affording the product as a white solid, which was found to be crystalline via powder X-ray diffraction. Yield: 36.95 g, 66.39 mmol, 94%. LCMS m/z 461.3 [M+H]$^+$. $^1$H NMR (400 MHz, DMSO-d$_6$) δ 10.87 (s, 1H), 10.40 (br s, 1H), 8.70-8.52 (br s, 2H), 8.44 (d, J=2.7 Hz, 1H), 7.78 (s, 1H), 7.75-7.73 (m, 1H), 7.45 (t, $J_{HF}$=72.9 Hz, 1H), 4.66 (br AB quartet, $J_{AB}$=13.9 Hz, $Δv_{AB}$=81 Hz, 2H), 3.23 (s, 3H), 2.65 (s, 3H), 2.35 (s, 3H), 1.84 (br s, 3H). Recrystallization of a sample of 9 from methanol afforded a crystal that was used for X-ray crystal structure analysis (see below); this confirmed the absolute stereochemistry as that drawn.

Single-Crystal X-Ray Structure Determination on 9

Data collection was performed on a Bruker APEX diffractometer at room temperature. Data collection consisted of omega and phi scans. Resolution limited to 1.0 angstroms, data collection cut short, thus data to parameter ratio near 3:1.

The structure was solved by direct methods using SHELX software suite in the space group P2$_1$2$_1$2$_1$. The structure was subsequently refined by the full-matrix least squares method. All non-hydrogen atoms were found and refined using anisotropic displacement parameters.

The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek, 2010). The results indicate that the absolute structure has been correctly assigned. The method calculates that the probability that the structure is correct is 100.0. The Hooft parameter is reported as 0.023 with an esd of 0.07.

The final R-index was 3.0%. A final difference Fourier revealed no missing or misplaced electron density.

Pertinent crystal, data collection and refinement information is summarized in Table 1. Atomic coordinates, bond lengths, bond angles, and displacement parameters are listed in Tables 2-5.

SOFTWARE AND REFERENCES

SHELXTL, Version 5.1, Bruker AXS, 1997.
PLATON, A. L. Spek, J. Appl. Cryst. 2003, 36, 7-13.
MERCURY, C. F. Macrae, P. R. Edington, P. McCabe, E. Pidcock, G. P. Shields, R. Taylor, M. Towler, and J. van de Streek, J. Appl. Cryst. 2006, 39, 453-457.
OLEX2, O. V. Dolomanov, L. J. Bourhis, R. J. Gildea, J. A. K. Howard, and H. Puschmann, J. Appl. Cryst. 2009, 42, 339-341.
R. W. W. Hooft, L. H. Strayer, and A. L. Spek, J. Appl. Cryst. 2008, 41, 96-103.
H. D. Flack, Acta Cryst. 1983, A39, 867-881.

TABLE 1

| Crystal data and structure refinement for 9. | |
|---|---|
| Empirical formula | C$_{17}$H$_{22}$F$_2$N$_6$O$_7$S$_3$ |
| Formula weight | 556.59 |
| Temperature | 298(2) K |
| Wavelength | 1.54178 Å |
| Crystal system | Orthorhombic |
| Space group | P2$_1$2$_1$2$_1$ |
| Unit cell dimensions | a = 6.6239(3) Å |
| | b = 12.4160(6) Å |
| | c = 28.8517(14) Å |
| | α = 90° |
| | β = 90° |
| | γ = 90° |

TABLE 1-continued

Crystal data and structure refinement for 9.

| | |
|---|---|
| Volume | 2372.83(19) Å$^3$ |
| Z | 4 |
| Density (calculated) | 1.558 Mg/m$^3$ |
| Absorption coefficient | 3.475 mm$^{-1}$ |
| F(000) | 1152 |
| Crystal size | 0.24 × 0.18 × 0.06 mm$^3$ |
| Theta range for data collection | 3.06 to 42.31° |
| Index ranges | −5 <= h <= 5, |
| | −10 <= k <= 10, |
| | −24 <= l <= 24 |
| Reflections collected | 20417 |
| Independent reflections | 1639 [R(int) = 0.0469] |
| Completeness to theta = 70.31° | 99.2% |
| Absorption correction | None |
| Max. and min. transmission | 0.8186 and 0.4893 |
| Refinement method | Full-matrix least-squares on F$^2$ |
| Data/restraints/parameters | 1639/6/336 |
| Goodness-of-fit on F$^2$ | 1.055 |
| Final R indices [I > 2sigma(I)] | R1 = 0.0304, wR2 = 0.0763 |
| R indices (all data) | R1 = 0.0324, wR2 = 0.0777 |
| Absolute structure parameter | 0.03(3) |
| Largest diff. peak and hole | 0.375 and −0.217 e.Å$^{-3}$ |

TABLE 2

Atomic coordinates (×10$^4$) and equivalent isotropic displacement parameters (Å$^2$ × 10$^3$) for 9. U(eq) is defined as one-third of the trace of the orthogonalized U$^{ij}$ tensor.

| | x | y | z | U(eq) |
|---|---|---|---|---|
| C(1) | 7487(9) | 4467(4) | 5085(2) | 34(2) |
| C(2) | 12429(10) | 4239(5) | 4312(2) | 51(2) |
| C(3) | 11467(11) | 5313(6) | 4995(3) | 27(2) |
| C(4) | 8447(10) | 4980(5) | 5515(2) | 31(2) |
| C(5) | 7074(9) | 5896(5) | 5681(2) | 42(2) |
| C(6) | 8712(10) | 4172(5) | 5902(2) | 29(2) |
| C(7) | 9730(12) | 3138(5) | 6562(2) | 45(2) |
| C(8) | 7770(13) | 3031(6) | 6442(2) | 36(2) |
| C(9) | 6437(13) | 1924(6) | 7069(3) | 40(2) |
| C(10) | 4615(14) | 1238(6) | 7160(3) | 47(2) |
| C(11) | 4360(14) | 742(6) | 7599(3) | 60(2) |
| C(12) | 5759(15) | 826(7) | 8013(3) | 95(3) |
| C(13) | 2670(19) | 152(8) | 7645(3) | 74(3) |
| C(14) | 1345(14) | 23(6) | 7296(4) | 58(2) |
| C(15) | 1672(15) | 538(7) | 6865(3) | 65(2) |
| C(16) | −1085(14) | −1301(11) | 7086(4) | 111(4) |
| C(17) | 4161(10) | 8489(5) | 6216(2) | 65(2) |
| N(1) | 11059(7) | 4493(4) | 4700(2) | 34(1) |
| N(2) | 12959(9) | 5985(4) | 4909(2) | 35(1) |
| N(3) | 10396(8) | 5457(4) | 5384(2) | 31(1) |
| N(4) | 7189(8) | 3616(4) | 6059(2) | 34(1) |
| N(5) | 6287(10) | 2384(5) | 6637(2) | 41(2) |
| N(6) | 3322(12) | 1129(5) | 6819(2) | 52(2) |
| O(1) | 8423(6) | 3371(3) | 4335(1) | 52(1) |
| O(2) | 9836(6) | 2761(3) | 5076(1) | 47(1) |
| O(3) | 7823(9) | 2044(4) | 7328(2) | 74(2) |
| O(5) | 1628(7) | 7046(3) | 5993(1) | 65(1) |
| O(6) | 3176(7) | 8017(3) | 5376(1) | 63(1) |
| O(7) | 741(8) | 8894(4) | 5856(2) | 73(1) |
| O(4A) | −410(11) | −563(6) | 7375(2) | 103(2) |
| F(1) | −2206(11) | −639(7) | 6794(3) | 173(3) |
| F(2) | −2449(11) | −1873(5) | 7278(3) | 179(4) |
| S(1) | 9156(2) | 3614(1) | 4784(1) | 37(1) |
| S(2) | 10919(3) | 4016(1) | 6197(1) | 48(1) |
| S(3) | 2270(3) | 8084(1) | 5832(1) | 40(1) |

TABLE 3

Symmetry transformations used to generate equivalent atoms.
Bond lengths [Å] and angles [°] for 9.

| | |
|---|---|
| C(1)—C(4) | 1.533(7) |
| C(1)—S(1) | 1.759(6) |
| C(1)—H(1A) | 0.9700 |
| C(1)—H(1B) | 0.9700 |
| C(2)—N(1) | 1.475(7) |
| C(2)—H(2A) | 0.9600 |
| C(2)—H(2B) | 0.9600 |
| C(2)—H(2C) | 0.9600 |
| C(3)—N(2) | 1.317(7) |
| C(3)—N(3) | 1.340(7) |
| C(3)—N(1) | 1.354(7) |
| C(4)—N(3) | 1.470(8) |
| C(4)—C(6) | 1.511(8) |
| C(4)—C(5) | 1.532(8) |
| C(5)—H(5A) | 0.9600 |
| C(5)—H(5B) | 0.9600 |
| C(5)—H(5C) | 0.9600 |
| C(6)—N(4) | 1.303(7) |
| C(6)—S(2) | 1.703(6) |
| C(7)—C(8) | 1.351(9) |
| C(7)—S(2) | 1.708(7) |
| C(7)—H(7) | 0.9300 |
| C(8)—N(4) | 1.377(7) |
| C(8)—N(5) | 1.389(8) |
| C(9)—O(3) | 1.194(8) |
| C(9)—N(5) | 1.374(8) |
| C(9)—C(10) | 1.500(10) |
| C(10)—N(6) | 1.312(8) |
| C(10)—C(11) | 1.419(9) |
| C(11)—C(13) | 1.344(11) |
| C(11)—C(12) | 1.515(11) |
| C(12)—H(12A) | 0.9600 |
| C(12)—H(12B) | 0.9600 |
| C(12)—H(12C) | 0.9600 |
| C(13)—C(14) | 1.344(11) |
| C(13)—H(13) | 0.9300 |
| C(14)—O(4A) | 1.390(9) |
| C(14)—C(15) | 1.416(10) |
| C(15)—N(6) | 1.323(9) |
| C(15)—H(15) | 0.9300 |
| C(16)—F(2) | 1.275(10) |
| C(16)—O(4A) | 1.318(11) |
| C(16)—F(1) | 1.392(9) |
| C(16)—H(16) | 0.9800 |
| C(17)—S(3) | 1.745(6) |
| C(17)—H(17A) | 0.9600 |
| C(17)—H(17B) | 0.9600 |
| C(17)—H(17C) | 0.9600 |
| N(1)—S(1) | 1.685(5) |
| N(2)—H(222) | 1.01(2) |
| N(2)—H(223) | 0.98(2) |
| N(3)—H(333) | 0.99(2) |
| N(5)—H(555) | 0.97(2) |
| O(1)—S(1) | 1.416(4) |
| O(2)—S(1) | 1.425(4) |
| O(5)—S(3) | 1.434(4) |
| O(6)—S(3) | 1.450(4) |
| O(7)—S(3) | 1.429(5) |
| C(4)—C(1)—S(1) | 112.9(4) |
| C(4)—C(1)—H(1A) | 109.0 |
| S(1)—C(1)—H(1A) | 109.0 |
| C(4)—C(1)—H(1B) | 109.0 |
| S(1)—C(1)—H(1B) | 109.0 |
| H(1A)—C(1)—H(1B) | 107.8 |
| N(1)—C(2)—H(2A) | 109.5 |
| N(1)—C(2)—H(2B) | 109.5 |
| H(2A)—C(2)—H(2B) | 109.5 |
| N(1)—C(2)—H(2C) | 109.5 |
| H(2A)—C(2)—H(2C) | 109.5 |
| H(2B)—C(2)—H(2C) | 109.5 |
| N(2)—C(3)—N(3) | 118.0(6) |
| N(2)—C(3)—N(1) | 120.5(6) |
| N(3)—C(3)—N(1) | 121.4(7) |
| N(3)—C(4)—C(6) | 110.8(5) |
| N(3)—C(4)—C(5) | 107.6(5) |
| C(6)—C(4)—C(5) | 109.4(5) |

TABLE 3-continued

Symmetry transformations used to generate equivalent atoms.
Bond lengths [Å] and angles [°] for 9.

| | |
|---|---|
| N(3)—C(4)—C(1) | 108.8(5) |
| C(6)—C(4)—C(1) | 111.7(4) |
| C(5)—C(4)—C(1) | 108.4(5) |
| C(4)—C(5)—H(5A) | 109.5 |
| C(4)—C(5)—H(5B) | 109.5 |
| H(5A)—C(5)—H(5B) | 109.5 |
| C(4)—C(5)—H(5C) | 109.5 |
| H(5A)—C(5)—H(5C) | 109.5 |
| H(5B)—C(5)—H(5C) | 109.5 |
| N(4)—C(6)—C(4) | 121.2(6) |
| N(4)—C(6)—S(2) | 115.5(4) |
| C(4)—C(6)—S(2) | 123.0(5) |
| C(8)—C(7)—S(2) | 110.3(6) |
| C(8)—C(7)—H(7) | 124.9 |
| S(2)—C(7)—H(7) | 124.9 |
| C(7)—C(8)—N(4) | 115.1(7) |
| C(7)—C(8)—N(5) | 129.2(7) |
| N(4)—C(8)—N(5) | 115.7(7) |
| O(3)—C(9)—N(5) | 124.9(7) |
| O(3)—C(9)—C(10) | 125.3(8) |
| N(5)—C(9)—C(10) | 109.7(8) |
| N(6)—C(10)—C(11) | 123.1(8) |
| N(6)—C(10)—C(9) | 116.9(7) |
| C(11)—C(10)—C(9) | 120.0(9) |
| C(13)—C(11)—C(10) | 115.0(8) |
| C(13)—C(11)—C(12) | 118.1(9) |
| C(10)—C(11)—C(12) | 126.9(9) |
| C(11)—C(12)—H(12A) | 109.5 |
| C(11)—C(12)—H(12B) | 109.5 |
| H(12A)—C(12)—H(12B) | 109.5 |
| C(11)—C(12)—H(12C) | 109.5 |
| H(12A)—C(12)—H(12C) | 109.5 |
| H(12B)—C(12)—H(12C) | 109.5 |
| C(11)—C(13)—C(14) | 122.4(8) |
| C(11)—C(13)—H(13) | 118.8 |
| C(14)—C(13)—H(13) | 118.8 |
| C(13)—C(14)—O(4A) | 119.1(10) |
| C(13)—C(14)—C(15) | 120.2(7) |
| O(4A)—C(14)—C(15) | 120.5(10) |
| N(6)—C(15)—C(14) | 117.6(7) |
| N(6)—C(15)—H(15) | 121.2 |
| C(14)—C(15)—H(15) | 121.2 |
| F(2)—C(16)—O(4A) | 110.7(10) |
| F(2)—C(16)—F(1) | 102.3(7) |
| O(4A)—C(16)—F(1) | 98.8(10) |
| F(2)—C(16)—H(16) | 114.5 |
| O(4A)—C(16)—H(16) | 114.5 |
| F(1)—C(16)—H(16) | 114.5 |
| S(3)—C(17)—H(17A) | 109.5 |
| S(3)—C(17)—H(17B) | 109.5 |
| H(17A)—C(17)—H(17B) | 109.5 |
| S(3)—C(17)—H(17C) | 109.5 |
| H(17A)—C(17)—H(17C) | 109.5 |
| H(17B)—C(17)—H(17C) | 109.5 |
| C(3)—N(1)—C(2) | 121.0(5) |
| C(3)—N(1)—S(1) | 123.1(5) |
| C(2)—N(1)—S(1) | 115.5(4) |
| C(3)—N(2)—H(222) | 121(3) |
| C(3)—N(2)—H(223) | 131(4) |
| H(222)—N(2)—H(223) | 107(5) |
| C(3)—N(3)—C(4) | 128.8(5) |
| C(3)—N(3)—H(333) | 116(3) |
| C(4)—N(3)—H(333) | 114(4) |
| C(6)—N(4)—C(8) | 109.9(6) |
| C(9)—N(5)—C(8) | 123.9(7) |
| C(9)—N(5)—H(555) | 121(3) |
| C(8)—N(5)—H(555) | 115(3) |
| C(10)—N(6)—C(15) | 121.5(7) |
| C(16)—O(4A)—C(14) | 123.0(8) |
| O(1)—S(1)—O(2) | 119.3(2) |
| O(1)—S(1)—N(1) | 105.2(2) |
| O(2)—S(1)—N(1) | 109.3(2) |
| O(1)—S(1)—C(1) | 111.3(3) |
| O(2)—S(1)—C(1) | 110.8(2) |
| N(1)—S(1)—C(1) | 98.7(3) |
| C(6)—S(2)—C(7) | 89.2(4) |
| O(7)—S(3)—O(5) | 114.0(3) |
| O(7)—S(3)—O(6) | 112.1(3) |
| O(5)—S(3)—O(6) | 111.4(2) |
| O(7)—S(3)—C(17) | 106.0(3) |
| O(5)—S(3)—C(17) | 105.5(3) |
| O(6)—S(3)—C(17) | 107.2(3) |

TABLE 4

Anisotropic displacement parameters (Å$^2$ × 10$^3$) for 9. The anisotropic displacement factor exponent takes the form: $-2\pi^2[h^2a^{*2}U^{11} + \ldots + 2 h k a^* b^* U^{12}]$.

| | U$^{11}$ | U$^{22}$ | U$^{33}$ | U$^{23}$ | U$^{13}$ | U$^{12}$ |
|---|---|---|---|---|---|---|
| C(1) | 34(4) | 30(4) | 39(4) | 5(3) | 7(4) | 4(4) |
| C(2) | 54(5) | 46(4) | 53(4) | −23(4) | 13(5) | −8(4) |
| C(3) | 24(5) | 28(5) | 30(5) | 2(5) | −3(4) | 10(4) |
| C(4) | 33(5) | 32(4) | 28(4) | −5(4) | 3(4) | −5(4) |
| C(5) | 40(4) | 37(4) | 49(4) | 0(3) | 12(3) | 7(4) |
| C(6) | 38(5) | 27(4) | 21(4) | 1(4) | 2(4) | 6(4) |
| C(7) | 52(6) | 44(5) | 40(4) | 18(4) | −6(4) | 4(4) |
| C(8) | 55(7) | 27(4) | 27(5) | 3(4) | 5(5) | 1(5) |
| C(9) | 51(7) | 25(4) | 44(7) | 8(5) | 23(5) | −4(5) |
| C(10) | 77(7) | 43(5) | 20(5) | 4(5) | 14(6) | 19(6) |
| C(11) | 51(6) | 49(5) | 79(9) | 1(5) | 18(6) | −2(5) |
| C(12) | 101(7) | 132(8) | 52(5) | 29(5) | −3(6) | −9(7) |
| C(13) | 82(8) | 77(7) | 64(7) | 12(5) | 4(8) | 13(7) |
| C(14) | 51(7) | 32(5) | 91(8) | 9(5) | 38(7) | −28(5) |
| C(15) | 67(7) | 56(5) | 72(7) | −13(5) | 15(5) | −16(5) |
| C(16) | 35(6) | 176(12) | 122(9) | −19(9) | −41(7) | 17(8) |
| C(17) | 56(5) | 65(5) | 74(5) | −11(4) | −39(5) | −7(4) |
| N(1) | 37(3) | 33(3) | 32(3) | −15(3) | 6(3) | −9(3) |
| N(2) | 32(4) | 27(3) | 46(4) | −5(3) | 4(3) | −15(3) |
| N(3) | 32(4) | 28(3) | 32(4) | −5(3) | 2(3) | −4(3) |
| N(4) | 38(4) | 36(3) | 28(4) | 4(3) | 3(3) | −5(4) |
| N(5) | 53(5) | 43(4) | 26(4) | 12(4) | 0(4) | −15(4) |
| N(6) | 62(5) | 45(4) | 49(5) | 4(3) | 11(5) | −12(4) |
| O(1) | 66(3) | 58(3) | 31(3) | −15(2) | −4(2) | −20(2) |

TABLE 4-continued

Anisotropic displacement parameters (Å² × 10³) for 9. The anisotropic displacement factor exponent takes the form: $-2\pi^2[h^2a^{*2}U^{11} + \ldots + 2 h k a^* b^* U^{12}]$.

|        | $U^{11}$ | $U^{22}$ | $U^{33}$ | $U^{23}$ | $U^{13}$ | $U^{12}$ |
|--------|----------|----------|----------|----------|----------|----------|
| O(2)   | 56(3)    | 28(3)    | 57(3)    | 9(2)     | 2(2)     | 5(2)     |
| O(3)   | 75(4)    | 92(4)    | 53(4)    | 20(3)    | −22(3)   | −22(4)   |
| O(5)   | 100(4)   | 44(3)    | 51(3)    | −3(2)    | −4(3)    | −32(3)   |
| O(6)   | 92(4)    | 53(3)    | 44(3)    | −3(2)    | 6(3)     | −10(3)   |
| O(7)   | 69(3)    | 73(3)    | 78(3)    | −24(3)   | −30(3)   | 40(3)    |
| O(4A)  | 104(6)   | 99(5)    | 105(5)   | 7(4)     | 15(5)    | −34(5)   |
| F(1)   | 141(6)   | 251(8)   | 126(5)   | 20(5)    | −11(5)   | −87(6)   |
| F(2)   | 98(5)    | 120(4)   | 320(9)   | 98(5)    | −26(6)   | −69(4)   |
| S(1)   | 38(1)    | 33(1)    | 40(1)    | −5(1)    | 3(1)     | −4(1)    |
| S(2)   | 41(1)    | 57(1)    | 47(1)    | 11(1)    | −4(1)    | −4(1)    |
| S(3)   | 48(1)    | 34(1)    | 40(1)    | −3(1)    | −11(1)   | 0(1)     |

TABLE 5

Hydrogen coordinates (×10⁴) and isotropic displacement parameters (Å² × 10³) for 9.

|        | x        | y        | z        | U(eq)  |
|--------|----------|----------|----------|--------|
| H(1A)  | 7036     | 5033     | 4878     | 41     |
| H(1B)  | 6311     | 4056     | 5179     | 41     |
| H(2A)  | 12335    | 4793     | 4081     | 77     |
| H(2B)  | 12052    | 3560     | 4178     | 77     |
| H(2C)  | 13791    | 4197     | 4425     | 77     |
| H(5A)  | 7663     | 6234     | 5948     | 63     |
| H(5B)  | 5773     | 5610     | 5761     | 63     |
| H(5C)  | 6925     | 6417     | 5438     | 63     |
| H(7)   | 10345    | 2783     | 6809     | 55     |
| H(12A) | 5339     | 326      | 8248     | 142    |
| H(12B) | 5712     | 1545     | 8135     | 142    |
| H(12C) | 7114     | 661      | 7919     | 142    |
| H(13)  | 2408     | −179     | 7928     | 89     |
| H(15)  | 760      | 463      | 6622     | 78     |
| H(16)  | −26      | −1717    | 6930     | 133    |
| H(17A) | 4482     | 9232     | 6162     | 97     |
| H(17B) | 5344     | 8056     | 6168     | 97     |
| H(17C) | 3697     | 8400     | 6529     | 97     |
| H(222) | 13170(80)| 6640(30) | 5110(15) | 45(19) |
| H(223) | 13830(90)| 6070(50) | 4635(16) | 90(30) |
| H(333) | 10840(90)| 6060(30) | 5587(15) | 50(20) |
| H(555) | 5100(50) | 2280(40) | 6446(16) | 40(20) |

Examples 10, 11, 12, and 13

N-{2-[(5R,6S)-3-Amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide (10), N-{2-[(5S,6R)-3-Amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide (11), N-{2-[(5S,6S)-3-Amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide (12), and N-{2-[(5R,6R)-3-Amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide (13)

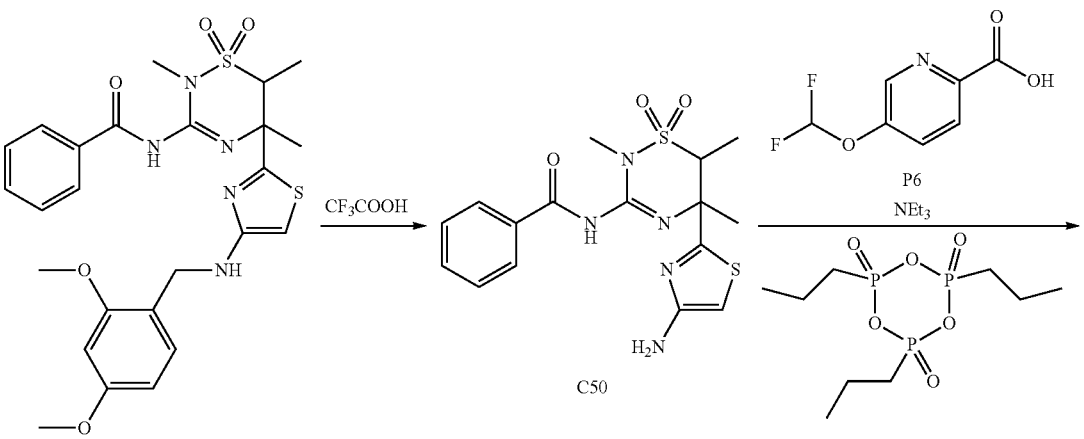

-continued

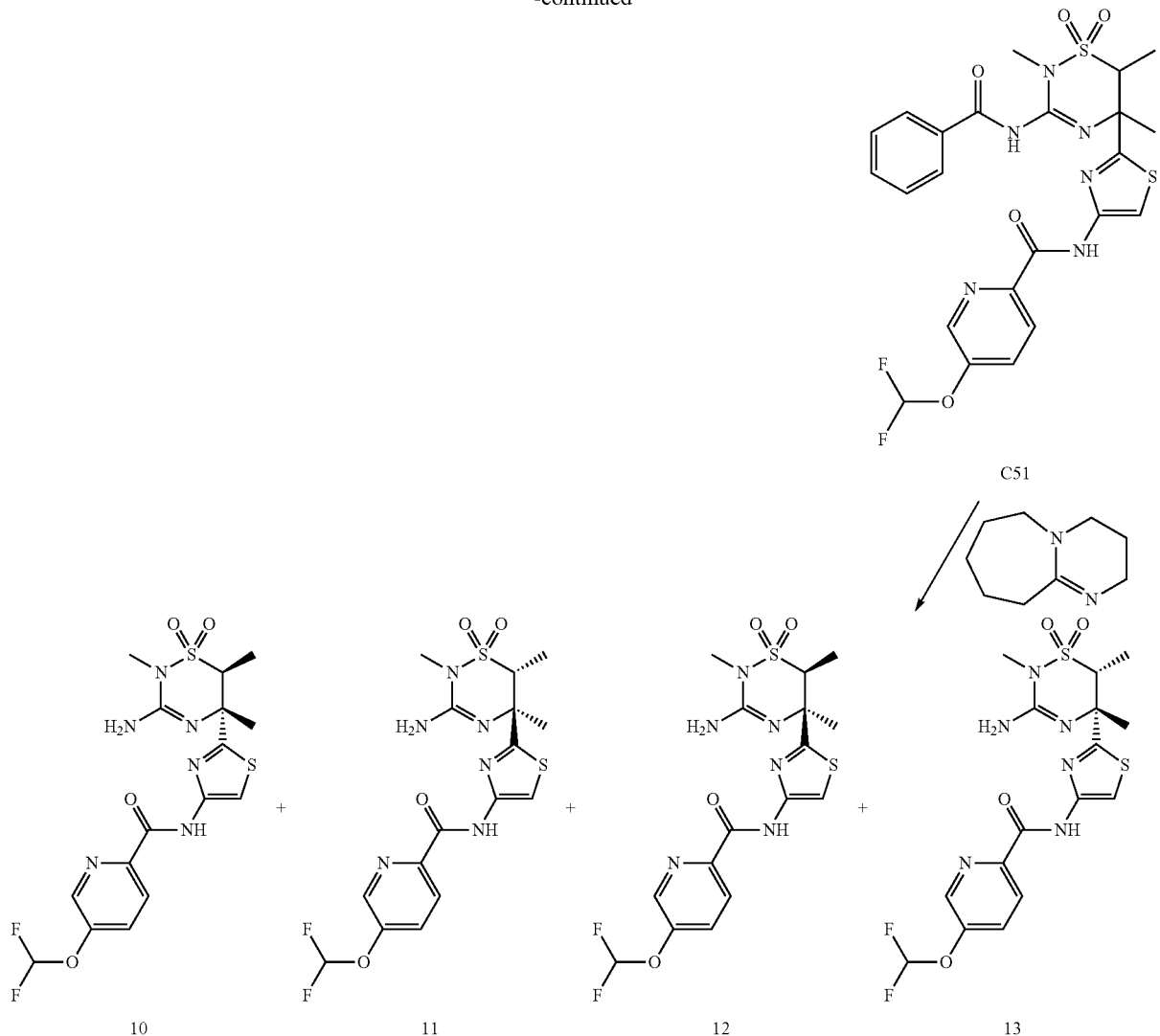

Step 1. Synthesis of N-[5-(4-amino-1,3-thiazol-2-yl)-2,5,6-trimethyl-1,1-dioxido-5,6-dihydro-2H-1,2,4-thiadiazin-3-yl]benzamide (C50)

Conversion of P5 to C50 was carried out using the procedure described for synthesis of C44 from P3 in Examples 3, 4, and 5. The product was isolated as an orange solid, which was taken directly to the following step. Analysis of the reaction mixture by LCMS at the conclusion of the experiment revealed two close-running products in a 1:1 ratio, presumed to be the two diastereomers of C50, with LCMS m/z 394.1 and 394.2 [M+H]$^+$.

Step 2. Synthesis of N-{2-[3-(benzoylamino)-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide (C51)

Reaction of C50 with P6 was carried out using the procedure described for synthesis of C45 from C44 in Examples 3, 4, and 5. The product was obtained as a white solid, which by $^1$H NMR analysis consisted of an approximately 1:1 mixture of diastereomers. Yield: 207 mg, 0.367 mmol, 44%. $^1$H NMR (400 MHz, CDCl$_3$), characteristic peaks: δ [12.34 (br s) and 12.23 (br s), total 1H], [10.44 (br s) and 10.43 (br s), total 1H], 8.52-8.47 (m, 1H), 8.34-8.30 (m, 1H), 8.29-8.21 (m, 2H), [7.83 (s) and 7.83 (s), total 1H], 7.71-7.66 (m, 1H), 7.58-7.51 (m, 1H), 7.49-7.42 (m, 2H), [6.66 (t, J$_{HF}$=71.9 Hz) and 6.66 (t, J$_{HF}$=71.9 Hz), total 1H], 3.52 (s, 3H), [2.05 (s) and 1.98 (s), total 3H], [1.73 (d, J=7.1 Hz) and 1.65 (d, J=7.0 Hz), total 3H].

Step 3. Synthesis of N-{2-[(5R,6S)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide (10), N-{2-[(5S,6R)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide (11), N-{2-[(5S,6S)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide (12), and N-{2-[(5R,6R)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide (13)

Conversion of C51 to a mixture of the products was carried out according to the method described for conversion of C45 to a mixture of 3, 4 and 5 in Examples 3, 4, and 5. The product mixture was isolated as a white solid (120 mg, 0.260 mmol, 73%); this material was separated into its component isomers via supercritical fluid chromatography [Column: Phenomenex Lux Cellulose-2, 5 μm; Mobile phase: 3:1 carbon dioxide/(1:1 acetonitrile/methanol)]. Each isomer was then subjected individually to chromatography on silica gel (Gradient: 0% to 10% methanol in dichloromethane) to afford the four products, each as a white solid.

The first-eluting isomer from the supercritical fluid chromatography provided 10. Yield: 13.5 mg, 29.3 μmol, 8%. LCMS m/z 461.3 [M+H]$^+$. $^1$H NMR (400 MHz, CDCl$_3$) δ 10.38 (br s, 1H), 8.48 (dd, J=2.6, 0.6 Hz, 1H), 8.31 (dd, J=8.6, 0.6 Hz, 1H), 7.71 (s, 1H), 7.67 (br dd, J=8.6, 2.7 Hz, 1H), 6.65 (t, $J_{HF}$=72.0 Hz, 1H), 3.93 (q, J=7.1 Hz, 1H), 3.29 (s, 3H), 1.72 (s, 3H), 1.68 (d, J=7.0 Hz, 3H).

The second-eluting isomer from the supercritical fluid chromatography provided 11. Yield: 39.5 mg, 85.8 μmol, 24%. LCMS m/z 461.3 [M+H]$^+$. $^1$H NMR (400 MHz, CDCl$_3$) δ 10.38 (br s, 1H), 8.48 (br d, J=2.6 Hz, 1H), 8.31 (dd, J=8.6, 0.6 Hz, 1H), 7.71 (s, 1H), 7.67 (br dd, J=8.6, 2.6 Hz, 1H), 6.65 (t, $J_{HF}$=72.0 Hz, 1H), 3.93 (q, J=7.0 Hz, 1H), 3.29 (s, 3H), 1.72 (s, 3H), 1.68 (d, J=7.0 Hz, 3H).

The third-eluting isomer from the supercritical fluid chromatography provided 12. Yield: 12.5 mg, 27.1 μmol, 8%. LCMS m/z 461.3 [M+H]$^+$. $^1$H NMR (400 MHz, CDCl$_3$) δ 10.39 (br s, 1H), 8.49 (dd, J=2.7, 0.5 Hz, 1H), 8.31 (dd, J=8.6, 0.6 Hz, 1H), 7.69 (s, 1H), 7.68 (ddt, J=8.6, 2.6, 0.7 Hz, 1H), 6.65 (t, $J_{HF}$=71.9 Hz, 1H), 3.83 (q, J=7.0 Hz, 1H), 3.29 (s, 3H), 1.88 (s, 3H), 1.25 (d, J=7.0 Hz, 3H).

The fourth-eluting isomer from the supercritical fluid chromatography provided 13. Yield: 7.7 mg, 16.7 μmol, 5%. LCMS m/z 461.3 [M+H]$^+$. $^1$H NMR (400 MHz, CDCl$_3$) δ 10.39 (br s, 1H), 8.49 (dd, J=2.7, 0.5 Hz, 1H), 8.32 (dd, J=8.6, 0.6 Hz, 1H), 7.71 (s, 1H), 7.68 (br dd, J=8.6, 2.7 Hz, 1H), 6.66 (t, $J_{HF}$=72.0 Hz, 1H), 3.84 (q, J=7.0 Hz, 1H), 3.31 (s, 3H), 1.90 (s, 3H), 1.31 (d, J=7.0 Hz, 3H).

The indicated relative and absolute stereochemistries were assigned on the basis of NMR work and biological activity. From the $^1$H NMR spectra, 10 and 11 are enantiomers of one another; 12 and 13 are also enantiomers of one another. NOE studies revealed that irradiation of the methine adjacent to the sulfonyl group results in an enhancement of the quaternary methyl group signal for both 12 and 13, but similar irradiation has no effect on the quaternary methyl group resonance in 10 and 11. This established the relative stereochemistry of the vicinal methyl groups. Examination of the biological activity of these four compounds (see Table 7) allowed assignment of the absolute stereochemistry, in accordance with Examples 3 and 4.

Examples 14, 15, 16, and 17

N-{2-[(5R,6S)-3-Amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (14), N-{2-[(5S,6R)-3-Amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (15), N-{2-[(5R,6R)-3-Amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (16), and N-{2-[(5S,6S)-3-Amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (17)

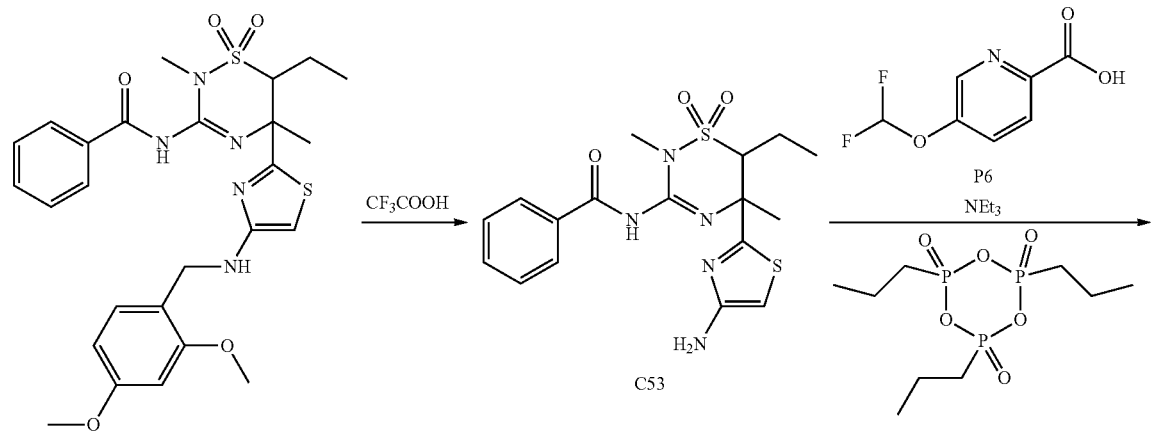

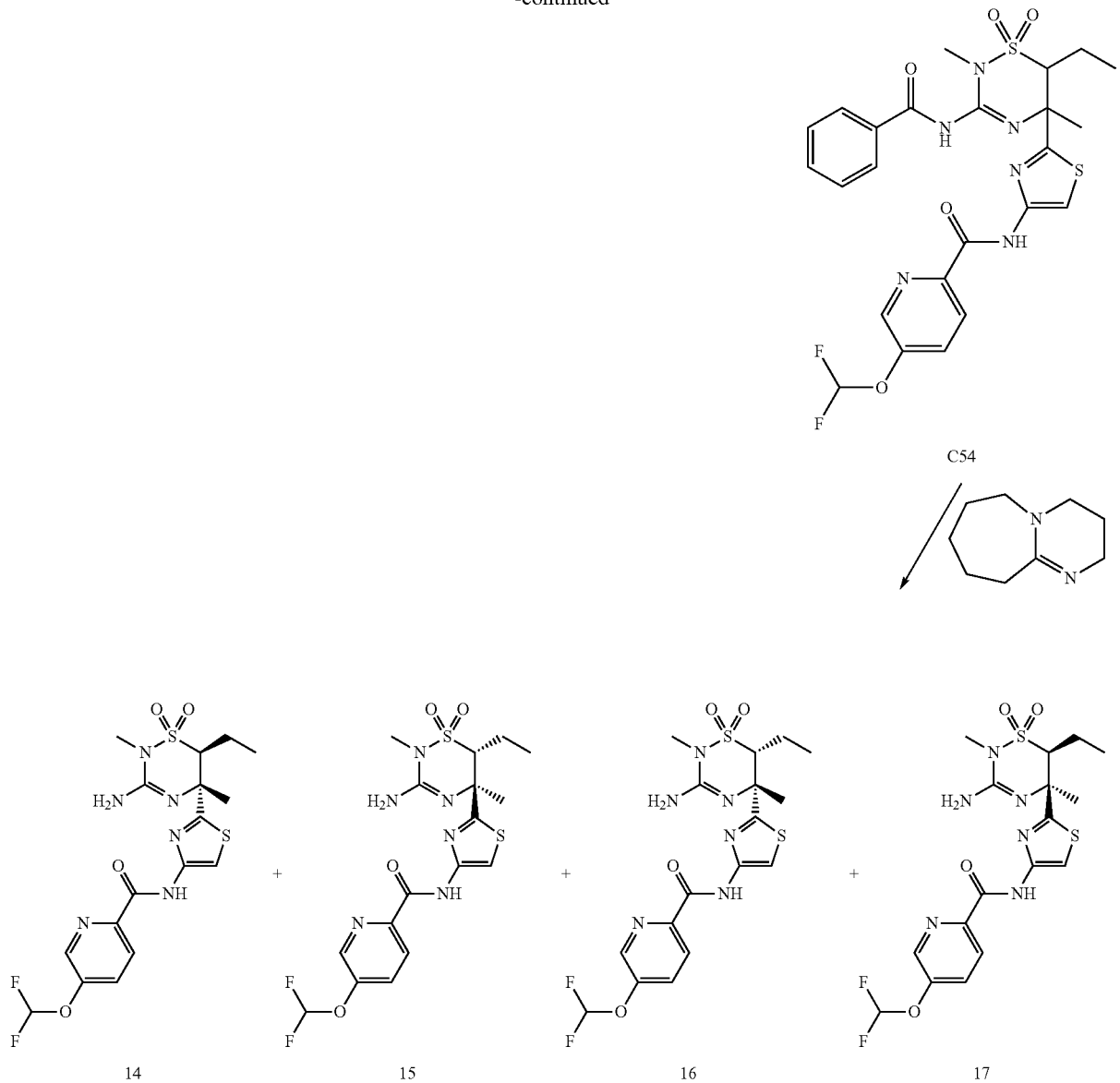

Step 1. Synthesis of N-[5-(4-amino-1,3-thiazol-2-yl)-6-ethyl-2,5-dimethyl-1,1-dioxido-5,6-dihydro-2H-1,2,4-thiadiazin-3-yl]benzamide (C53)

Trifluoroacetic acid (0.38 mL, 4.9 mmol) was added in a drop-wise manner to a 0° C. solution of C52 [N-(5-{4-[(2,4-dimethoxybenzyl)amino]-1,3-thiazol-2-yl}-6-ethyl-2,5-dimethyl-1,1-dioxido-5,6-dihydro-2H-1,2,4-thiadiazin-3-yl)benzamide; this material was prepared in analogous fashion to P3, by utilizing propane-1-sulfonyl chloride in place of cyclopropylmethanesulfonyl chloride] (140 mg, 0.251 mmol) in dichloromethane (4 mL) The reaction mixture was stirred at 0° C. for 1 hour. Analysis of the reaction mixture by LCMS at the end of the reaction indicated a major peak consistent with the molecular weight of the product: LCMS m/z 408.3 [M+H]$^+$. The reaction mixture was diluted with additional dichloromethane and saturated aqueous sodium bicarbonate solution. The aqueous layer was extracted twice with dichloromethane, and the combined organic layers were dried over sodium sulfate, filtered, and concentrated under reduced pressure to provide the product as an orange solid (100 mg). This material was used directly in the following step.

Step 2. Synthesis of N-{2-[3-(benzoylamino)-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (C54)

Reaction of C53 (from the previous step; 100 mg, ≤0.245 mmol) with P6 to provide the product was effected using the method described for synthesis of C43 from P2 in Example 2. In this case, no chromatographic purification was carried out; the product was isolated as a yellow solid (130 mg), which was used directly in the following step.

Step 3. Synthesis of N-{2-[(5R,6S)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (14), N-{2-[(5S,6R)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (15), N-{2-[(5R,6R)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (16), and N-{2-[(5S,6S)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide (17)

1,8-Diazabicyclo[5.4.0]undec-7-ene (33.9 µL, 0.227 mmol) was added to a solution of C54 (130 mg, ≤0.225 mmol) in methanol (2.2 mL). The reaction mixture was heated to 60° C. for 16 hours, whereupon it was concentrated under reduced pressure. The residue was dissolved in dichloromethane (10 mL) and adsorbed on silica gel; chromatography on silica gel (Gradient: 20% to 100% ethyl acetate in heptane) provided a mixture of the products (45 mg, 95 µmol, 38% over 3 steps). This material was separated into its four component isomers using supercritical fluid chromatography [Column: Phenomenex Lux Cellulose-2, 5 µm; Mobile phase: 45:55 carbon dioxide/(methanol containing 0.2% ammonium hydroxide)]. In order of elution:

14: Yield: 6.2 mg, 14% for the separation. LCMS m/z 475.3 [M+H]$^+$. $^1$H NMR (400 MHz, CDCl$_3$) δ 10.41 (br s, 1H), 8.50 (dd, J=2.7, 0.5 Hz, 1H), 8.32 (dd, J=8.6, 0.5 Hz, 1H), 7.79 (s, 1H), 7.68 (br dd, J=8.6, 2.6 Hz, 1H), 6.66 (t, J$_{HF}$=71.9 Hz, 1H), 3.83-3.76 (m, 1H), 3.33 (s, 3H), 2.23-2.12 (m, 2H), 1.83 (s, 3H), 1.17 (t, J=7.5 Hz, 3H).

15: Yield: 17.5 mg, 39% for the separation. LCMS m/z 475.3 [M+H]$^+$. $^1$H NMR (400 MHz, CDCl$_3$) δ 10.40 (br s, 1H), 8.50 (d, J=2.3 Hz, 1H), 8.32 (d, J=8.6 Hz, 1H), 7.78 (s, 1H), 7.68 (br dd, J=8.6, 2.6 Hz, 1H), 6.66 (t, J$_{HF}$=71.9 Hz, 1H), 3.78-3.71 (m, 1H), 3.32 (s, 3H), 2.28-2.11 (m, 2H), 1.81 (s, 3H), 1.17 (t, J=7.4 Hz, 3H).

16: Yield: 1.2 mg, 3% for the separation. $^1$H NMR (400 MHz, CDCl$_3$) δ 10.39 (br s, 1H), 8.50 (dd, J=2.7, 0.5 Hz, 1H), 8.32 (dd, J=8.6, 0.6 Hz, 1H), 7.74 (s, 1H), 7.68 (br dd, J=8.6, 2.7 Hz, 1H), 6.66 (t, J$_{HF}$=71.9 Hz, 1H), 3.63 (dd, J=7.7, 3.2 Hz, 1H), 3.31 (s, 3H), 2.02-1.9 (m, 2H), 1.89 (s, 3H), 1.12 (t, J=7.5 Hz, 3H).

17: Yield: 9.4 mg, 21% for the separation. LCMS m/z 475.3 [M+H]$^+$. $^1$H NMR (400 MHz, CDCl$_3$) δ 10.39 (br s, 1H), 8.50 (br d, J=2.5 Hz, 1H), 8.32 (dd, J=8.6, 0.5 Hz, 1H), 7.75 (s, 1H), 7.68 (br dd, J=8.7, 2.7 Hz, 1H), 6.66 (t, J$_{HF}$=71.9 Hz, 1H), 3.62 (dd, J=7.8, 3.4 Hz, 1H), 3.30 (s, 3H), 2.09-1.9 (m, 2H), 1.89 (s, 3H), 1.14 (t, J=7.3 Hz, 3H).

The indicated relative and absolute stereochemistries were assigned on the basis of NMR work and biological activity. From the $^1$H NMR spectra, 14 and 15 are enantiomers of one another; 16 and 17 are also enantiomers of one another. NOE studies revealed that irradiation of the methine adjacent to the sulfonyl group results in an enhancement of the quaternary methyl group signal for both 16 and 17, but has no effect on that resonance in 15. This established the relative stereochemistry of the vicinal methyl and ethyl groups. Examination of the biological activity of these four compounds (see Table 7) allowed assignment of the absolute stereochemistries, in accordance with Examples 3 and 4.

TABLE 6

Method of Preparation, Structure, and Physicochemical Properties for Examples 18-28.

| Example number | Method of Preparation; Non-commercial starting materials | Structure | $^1$H NMR (400 MHz, CHCl$_3$); Mass spectrum, observed ion m/z [M + H]$^+$ (unless otherwise indicated) |
|---|---|---|---|
| 18 | Example 2; P2 | (structure) | 10.26 (br s, 1H), 9.43 (s, 1H), 8.78 (s, 1H), 7.75 (s, 1H), 5.67 (d, JHF = 46.4 Hz, 2H), 4.13 (d, J = 13.7 Hz, 1H), 3.69 (d, J = 13.7 Hz, 1H), 3.30 (s, 3H), 1.80 (s, 3H); 414.1 |

TABLE 6-continued

Method of Preparation, Structure, and Physicochemical Properties for Examples 18-28.

| Example number | Method of Preparation; Non-commercial starting materials | Structure | $^1$H NMR (400 MHz, CHCl$_3$); Mass spectrum, observed ion m/z [M + H]$^+$ (unless otherwise indicated) |
|---|---|---|---|
| 19 | Example 2; P2 | 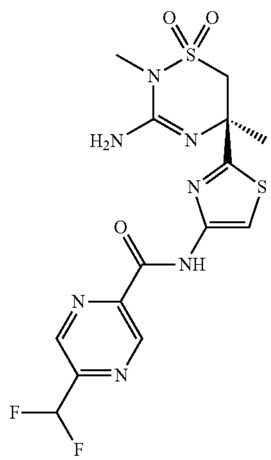 [SMILES: CN1C(N)=N[C@](C)(c2nc(NC(=O)c3cnc(C(F)F)cn3)cs2)CS1(=O)=O] | 9.50 (s, 1H), 8.94 (s, 1H), 7.76 (s, 1H), 6.79 (t, J$_{HF}$ = 54.4 Hz, 1H), 4.15 (d, J = 13.7 Hz, 1H), 3.66 (br d, J = 13.7 Hz, 1H), 3.28-3.23 (m, 3H), 1.79 (br s, 3H); 432.1 |
| 20 | Example 2; P2 | 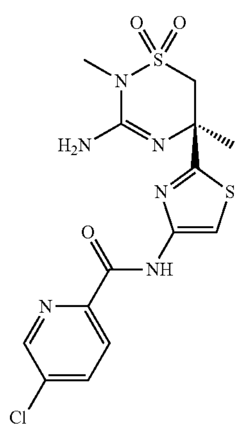 [SMILES: CN1C(N)=N[C@](C)(c2nc(NC(=O)c3ccc(Cl)cn3)cs2)CS1(=O)=O] | 10.40 (br s, 1H), 8.59 (d, J = 2.0 Hz, 1H), 8.23 (d, J = 8.6 Hz, 1H), 7.89 (dd, J = 8.2, 2.3 Hz, 1H), 7.72 (s, 1H), 4.13 (d, J = 14.0 Hz, 1H), 3.70 (d, J = 13.7 Hz, 1H), 3.30 (s, 3H), 1.81 (s, 3H); 415.0 (chlorine isotope pattern observed) |
| 21 | Example 2; P2, P9 | 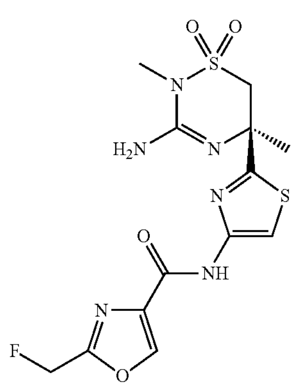 [SMILES: CN1C(N)=N[C@](C)(c2nc(NC(=O)c3coc(CF)n3)cs2)CS1(=O)=O] | By $^1$H NMR analysis, judged to be a mixture of rotamers; [9.40 (br s) and 9.37 (br s), total 1H], [8.37 (d, J = 1.3 Hz) and 8.36 (d, J = 1.4 Hz), total 1H], [7.72 (br s) and 7.69-7.66 (m), total 1H], 5.44 (d, J$_{HF}$ = 47.1 Hz, 2H), 4.27-4.16 (m, 1H), 3.76 (br d, J = 14 Hz, 1H), 3.35 (s, 3H), [1.95 (br s) and 1.85 (s), total 3H]; 403.1 |

TABLE 6-continued

Method of Preparation, Structure, and Physicochemical Properties for Examples 18-28.

| Example number | Method of Preparation; Non-commercial starting materials | Structure | $^1$H NMR (400 MHz, CHCl$_3$); Mass spectrum, observed ion m/z [M + H]$^+$ (unless otherwise indicated) |
|---|---|---|---|
| 22 | Example 1[1,2]; P1 | 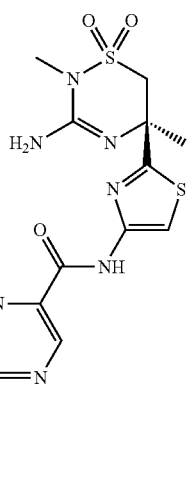 | 10.11 (br s, 1H), 9.00 (d, J = 1.3 Hz, 1H), 8.29 (d, J = 1.3 Hz, 1H), 7.72 (s, 1H), 4.62 (t, J$_{HF}$ = 11.9 Hz, 2H) 4.16 (d, J = 13.8 Hz, 1H), 3.72 (d, J = 13.8 Hz, 1H), 3.32 (s, 3H), 1.83 (s, 3H), 1.79 (t, J$_{HF}$ = 18.6 Hz, 3H); 476.1 |
| 23 | Example 1[3,2]; P1 | 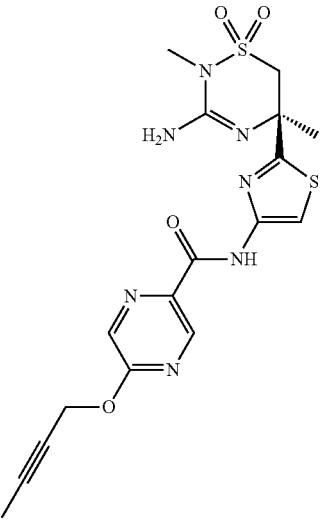 [SMILES: CC#CCOc1cnc(C(=O)Nc2csc([C@]3(C)CS(=O)(=O)N(C)C(N)=N3)n2)cn1] | By $^1$H NMR analysis, judged to be a mixture of rotamers; [10.14 (br s) and 10.10 (br s), total 1H], 9.02 (s, 1H), 8.23 (s, 1H), [7.78 (br s) and 7.70-7.68 (m), total 1H], 5.08-5.03 (m, 2H), 4.06 (br d, J = 14 Hz, 1H), 3.70-3.62 (m, 1H), [3.35 (br s) and 3.29-3.26 (m), total 3H], [1.96 (br s) and 1.78 (br s), total 3H], 1.92-1.88 (m, 3H); 450.1 |

TABLE 6-continued

Method of Preparation, Structure, and Physicochemical Properties for Examples 18-28.

| Example number | Method of Preparation; Non-commercial starting materials | Structure | $^1$H NMR (400 MHz, CHCl$_3$); Mass spectrum, observed ion m/z [M + H]$^+$ (unless otherwise indicated) |
|---|---|---|---|
| 24 | Example 1$^2$; P1, P10 | 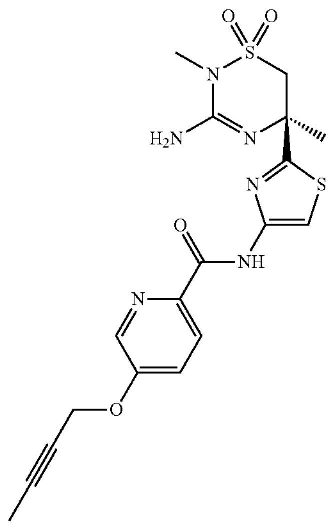 [SMILES: CC#CCOc1ccc(C(=O)Nc2csc([C@]3(C)CS(=O)(=O)N(C)C(N)=N3)n2)nc1] | This is likely a mixture of rotamers. Only peaks for the predominant rotamer were tabulated: 10.41 (br s, 1H), 8.34 (d, J = 2.7 Hz, 1H), 8.22 (d, J = 8.6 Hz, 1H), 7.70 (s, 1H), 7.44 (dd, J = 8.7, 2.8 Hz, 1H), 4.81-4.77 (m, 2H), 4.14 (d, J = 13.8 Hz, 1H), 3.73 (d, J = 13.8 Hz, 1H), 3.31 (s, 3H), 1.88 (t, J = 2.1 Hz, 3H), 1.83 (s, 3H); 449.2 |
| 25 | Example 2; P2, P8 | 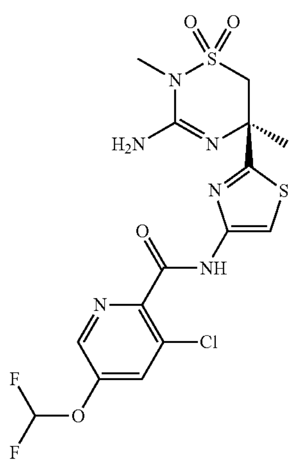 [SMILES: CN1C(N)=N[C@](C)(c2nc(NC(=O)c3ncc(OC(F)F)cc3Cl)cs2)CS1(=O)=O] | 10.35 (br s, 1H), 8.45-8.41 (m, 1H), 7.72 (s, 1H), 7.71-7.67 (m, 1H), 6.67 (t, J$_{HF}$ = 71.3 Hz, 1H), 4.00 (d, J = 13.6 Hz, 1H), 3.65 (d, J = 13.7 Hz, 1H), 3.26 (s, 3H), 1.75 (s, 3H); 481.0 |
| 26 | Example 1; P1 | 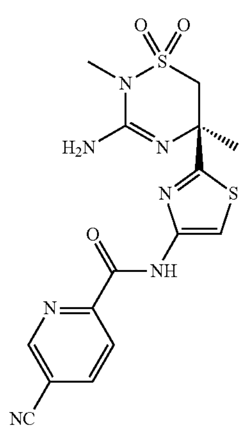 [SMILES: CN1C(N)=N[C@](C)(c2nc(NC(=O)c3ccc(C#N)cn3)cs2)CS1(=O)=O] | 10.43 (br s, 1H), 8.92 (br d, J = 1 Hz, 1H), 8.41 (br d, half of AB quartet, J = 8.2 Hz, 1H), 8.21 (dd, J = 8.2, 2.0 Hz, 1H), 7.73 (s, 1H), 4.05 (d, J = 13.7 Hz, 1H), 3.63 (d, J = 13.7 Hz, 1H), 3.26 (s, 3H), 1.75 (s, 3H); 406.0 |

TABLE 6-continued

Method of Preparation, Structure, and Physicochemical Properties for Examples 18-28.

| Example number | Method of Preparation; Non-commercial starting materials | Structure | $^1$H NMR (400 MHz, CHCl$_3$); Mass spectrum, observed ion m/z [M + H]$^+$ (unless otherwise indicated) |
|---|---|---|---|
| 27 | Example 1; P1 | 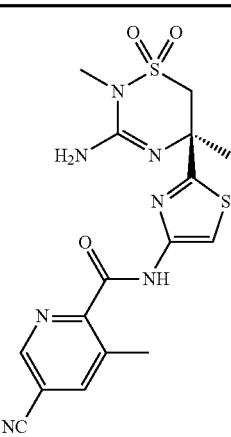 | 10.58 (br s, 1H), 8.76-8.73(m, 1H), 7.97-7.94 (m, 1H), 7.69 (s, 1H), 4.46-4.12 (br s, 2H), 4.04 (d, J = 13.7 Hz, 1H), 3.63 (d, J = 13.7 Hz, 1H), 3.26 (s, 3H), 2.87 (br s, 3H), 1.75 (s, 3H); LCMS m/z 442.0 [M + Na$^+$] |
| 28 | Example 1; P1 | 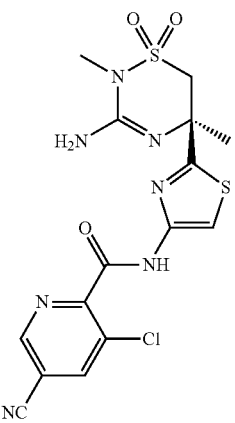 [SMILES: CN1C(N)=N[C@](C)(c2nc(NC(=O)c3ncc(C#N)cc3Cl)cs2)CS1(=O)=O] | 10.33 (br s, 1H), 8.80 (d, J = 1.6 Hz, 1H), 8.18 (d, J = 1.8 Hz, 1H), 7.74 (s, 1H), 4.03 (d, J = 13.6 Hz, 1H), 3.62 (d, J = 13.7 Hz, 1H), 3.26 (s, 3H), 1.74 (s, 3H); 439.9 (chlorine isotope pattern observed) |
| 29 | | 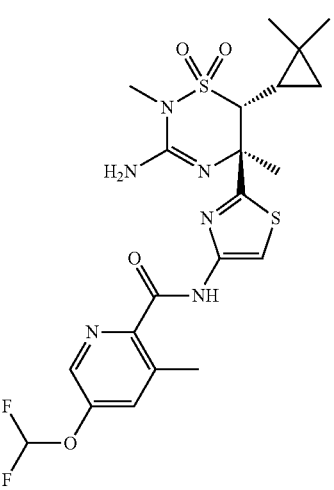 [SMILES: Cc1cc(OC(F)F)cnc1C(=O)Nc1csc([C@@]2(C)N=C(N)N(C)S(=O)(=O)[C@@H]2C2CC2(C)C)n1] | |

TABLE 6-continued
Method of Preparation, Structure, and Physicochemical Properties for Examples 18-28.
| Example number | Method of Preparation; Non-commercial starting materials | Structure | $^1$H NMR (400 MHz, CHCl$_3$) ; Mass spectrum, observed ion m/z [M + H]$^+$ (unless otherwise indicated) |
|---|---|---|---|
| 30 | | 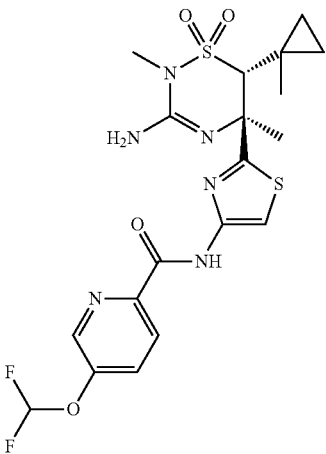 [SMILES: CN1C(N)=N[C@](C)(c2nc(NC(=O)c3ccc(OC(F)F)cn3)cs2)[C@@H](C2(C)CC2)S1(=O)=O] | |
| 31 | | 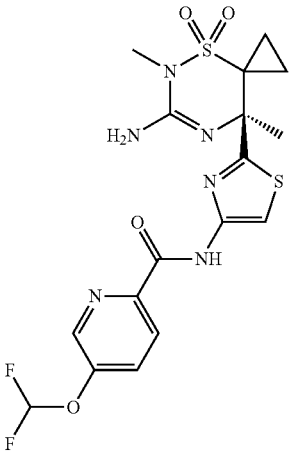 [SMILES: CN1C(N)=N[C@](C)(c2nc(NC(=O)c3ccc(OC(F)F)cn3)cs2)C2(CC2)S1(=O)=O] | |
| 32 | | 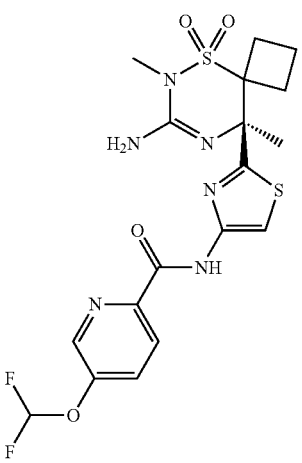 [SMILES: CN1C(N)=N[C@](C)(c2nc(NC(=O)c3ccc(OC(F)F)cn3)cs2)C2(CCC2)S1(=O)=O] | |

TABLE 6-continued

Method of Preparation, Structure, and Physicochemical Properties for Examples 18-28.

| Example number | Method of Preparation; Non-commercial starting materials | Structure | $^1$H NMR (400 MHz, CHCl$_3$) ; Mass spectrum, observed ion m/z [M + H]$^+$ (unless otherwise indicated) |
|---|---|---|---|
| 33 | | 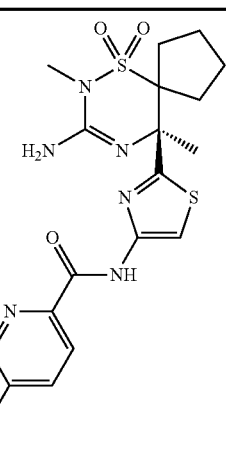 | |

1. Methyl 5-chloropyrazine-2-carboxylate was reacted with cesium carbonate and 2,2-difluoropropan-1-ol to provide methyl 5-(2,2-difluoropropoxy)pyrazine-2-carboxylate; ester hydrolysis was effected with lithium hydroxide to afford the requisite 5-(2,2-difluoropropoxy)pyrazine-2-carboxylic acid.

2. In this case, 2,4,6-tripropyl-1,3,5,2,4,6-trioxatriphosphinane 2,4,6-trioxide was used in place of O-(7-azabenzotriazol-1-yl)-N,N,N',N'-tetramethyluronium hexafluorophosphate.

3. Reaction of methyl 5-chloropyrazine-2-carboxylate with but-2-yn-1-ol and potassium tert-butoxide, followed by ester hydrolysis with lithium hydroxide, afforded the requisite 5-(but-2-yn-1-yloxy)pyrazine-2-carboxylic acid.

Biological Assays

BACE1 Cell-Free Assay:

Beta-secretase (BACE) is one of the enzymes involved in the generation of the amyloid beta peptide found in the amyloid plaques of Alzheimer's disease patients. This assay measures the inhibition of the beta-secretase enzyme as it cleaves a non-native peptide.

A synthetic APP substrate that can be cleaved by beta-secretase having N-terminal biotin and made fluorescent by the covalent attachment of Oregon Green at the Cys residue is used to assay beta-secretase activity in the presence or absence of the inhibitory compounds. The substrate is Biotin-GLTNIKTEEISEISY^EVEFR-C[Oregon Green]KK-OH. The BACE1 enzyme is affinity purified material from conditioned media of CHO-K1 cells that have been transfected with a soluble BACE construct (BACE1deltaTM96His). Compounds are incubated in a ½ log dose response curve from a top concentration of 100 μM with BACE1 enzyme and the biotinylated fluorescent peptide in 384-well black plates (Thermo Scientific #4318). BACE1 is at a final concentration of 0.1 nM with a final concentration of peptide substrate of 150 nM in a reaction volume of 30 μL assay buffer [100 mM sodium acetate, pH 4.5 (brought to pH with acetic acid), and 0.001% Tween-20]. Plates are covered and incubated for 3 hours at 37° C. The reaction is stopped with the addition of 30 μL of 1.5 μM Streptavidin (Pierce, #21125). After a 10 minute incubation at room temperature, plates are read on a PerkinElmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of beta-secretase enzymatic cleavage of the synthetic APP substrate.

TABLE 7

Biological activity and IUPAC name for Examples 1-28

| Example number | BACE1 Cell-free Assay IC$_{50}$ (μM)$^a$ | IUPAC Name |
|---|---|---|
| 1 | 0.060$^b$ | N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide |
| 2 | 0.019 | N-{2-[(5S)-3-amino-2,5-dimethyl-1,1-dioxido-5,6-dihydro-2H-1,2,4-thiadiazin-5-yl]-1,3-thiazol-4-yl}-1-(difluoromethyl)-1H-pyrazole-3-carboxamide |
| 3 | 31.2 | N-{2-[(5R,6S)-3-amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide |
| 4 | 0.103 | N-{2-[(5S,6R)-3-amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide |
| 5 | 0.051 | N-{2-[(5S,6S)-3-amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide |

TABLE 7-continued

Biological activity and IUPAC name for Examples 1-28

| Example number | BACE1 Cell-free Assay IC$_{50}$ (μM)$^a$ | IUPAC Name |
|---|---|---|
| 6 | 0.185$^c$ | N-[2-(3-amino-2,5,6,6-tetramethyl-1,1-dioxido-5,6-dihydro-2H-1,2,4-thiadiazin-5-yl)-1,3-thiazol-4-yl]-5-(difluoromethoxy)pyridine-2-carboxamide |
| 7 | 4.40 | N-{2-[(5R)-3-amino-2,5,6,6-tetramethyl-1,1-dioxido-5,6-dihydro-2H-1,2,4-thiadiazin-5-yl]-1,3-thiazol-4-yl}-5-(difluoromethoxy)pyridine-2-carboxamide |
| 8 | 0.078 | N-{2-[(5S)-3-amino-2,5,6,6-tetramethyl-1,1-dioxido-5,6-dihydro-2H-1,2,4-thiadiazin-5-yl]-1,3-thiazol-4-yl}-5-(difluoromethoxy)pyridine-2-carboxamide |
| 9 | 0.029$^b$ | N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)-3-methylpyridine-2-carboxamide, methanesulfonic acid salt |
| 10 | 18.0 | N-{2-[(5R,6S)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide |
| 11 | 0.136 | N-{2-[(5S,6R)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide |
| 12 | 0.088 | N-{2-[(5S,6S)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide |
| 13 | 33.8 | N-{2-[(5R,6R)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide |
| 14 | 14.2 | N-{2-[(5R,6S)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide |
| 15 | 0.371 | N-{2-[(5S,6R)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide |
| 16 | 3.92$^c$ | N-{2-[(5R,6R)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide |
| 17 | 0.200 | N-{2-[(5S,6S)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide |
| 18 | 0.246 | N-{2-[(5S)-3-amino-2,5-dimethyl-1,1-dioxido-5,6-dihydro-2H-1,2,4-thiadiazin-5-yl]-1,3-thiazol-4-yl}-5-(fluoromethyl)pyrazine-2-carboxamide |
| 19 | 0.172 | N-{2-[(5S)-3-amino-2,5-dimethyl-1,1-dioxido-5,6-dihydro-2H-1,2,4-thiadiazin-5-yl]-1,3-thiazol-4-yl}-5-(difluoromethyl)pyrazine-2-carboxamide |
| 20 | 0.042 | N-{2-[(5S)-3-amino-2,5-dimethyl-1,1-dioxido-5,6-dihydro-2H-1,2,4-thiadiazin-5-yl]-1,3-thiazol-4-yl}-5-chloropyridine-2-carboxamide |
| 21 | 0.011 | N-{2-[(5S)-3-amino-2,5-dimethyl-1,1-dioxido-5,6-dihydro-2H-1,2,4-thiadiazin-5-yl]-1,3-thiazol-4-yl}-2-(fluoromethyl)-1,3-oxazole-4-carboxamide |
| 22 | 0.134 | N-{2-[(5S)-3-amino-2,5-dimethyl-1,1-dioxido-5,6-dihydro-2H-1,2,4-thiadiazin-5-yl]-1,3-thiazol-4-yl}-5-(2,2-difluoropropoxy)pyrazine-2-carboxamide |
| 23 | 0.013 | N-{2-[(5S)-3-amino-2,5-dimethyl-1,1-dioxido-5,6-dihydro-2H-1,2,4-thiadiazin-5-yl]-1,3-thiazol-4-yl}-5-(but-2-yn-1-yloxy)pyrazine-2-carboxamide |
| 24 | 0.013 | N-{2-[(5S)-3-amino-2,5-dimethyl-1,1-dioxido-5,6-dihydro-2H-1,2,4-thiadiazin-5-yl]-1,3-thiazol-4-yl}-5-(but-2-yn-1-yloxy)pyridine-2-carboxamide |
| 25 | 0.023 | N-{2-[(5S)-3-amino-2,5-dimethyl-1,1-dioxido-5,6-dihydro-2H-1,2,4-thiadiazin-5-yl]-1,3-thiazol-4-yl}-3-chloro-5-(difluoromethoxy)pyridine-2-carboxamide |
| 26 | 0.045$^c$ | N-{2-[(5S)-3-amino-2,5-dimethyl-1,1-dioxido-5,6-dihydro-2H-1,2,4-thiadiazin-5-yl]-1,3-thiazol-4-yl}-5-cyanopyridine-2-carboxamide |
| 27 | 0.009 | N-{2-[(5S)-3-amino-2,5-dimethyl-1,1-dioxido-5,6-dihydro-2H-1,2,4-thiadiazin-5-yl]-1,3-thiazol-4-yl}-5-cyano-3-methylpyridine-2-carboxamide |
| 28 | N.D.$^d$ | N-{2-[(5S)-3-amino-2,5-dimethyl-1,1-dioxido-5,6-dihydro-2H-1,2,4-thiadiazin-5-yl]-1,3-thiazol-4-yl}-3-chloro-5-cyanopyridine-2-carboxamide |
| 29 | | N-(2-{(5S,6R)-3-amino-6-[(1R)-2,2-dimethylcyclopropyl]-2,5-dimethyl-1,1-dioxido-5,6-dihydro-2H-1,2,4-thiadiazin-5-yl}-1,3-thiazol-4-yl)-5-(difluoromethoxy)-3-methylpyridine-2-carboxamide |
| 30 | | N-{2-[(5S,6R)-3-amino-2,5-dimethyl-6-(1-methylcyclopropyl)-1,1-dioxido-5,6-dihydro-2H-1,2,4-thiadiazin-5-yl]-1,3-thiazol-4-yl}-5-(difluoromethoxy)pyridine-2-carboxamide |
| 31 | | N-{2-[(8S)-6-amino-5,8-dimethyl-4,4-dioxido-4-thia-5,7-diazaspiro[2.5]oct-6-en-8-yl]-1,3-thiazol-4-yl}-5-(difluoromethoxy) pyridine-2-carboxamide |
| 32 | | N-{2-[(9S)-7-amino-6,9-dimethyl-5,5-dioxido-5-thia-6,8-diazaspiro[3.5]non-7-en-9-yl]-1,3-thiazol-4-yl}-5-(difluoromethoxy) pyridine-2-carboxamide |
| 33 | | N-{2-[(10S)-8-amino-7,10-dimethyl-6,6-dioxido-6-thia-7,9-diazaspiro[4.5]dec-8-en-10-yl]-1,3-thiazol-4-yl}-5-(difluoromethoxy)pyridine-2-carboxamide |

$^a$Reported IC$_{50}$ values are the geometric mean of 2-4 determinations, unless otherwise indicated.
$^b$The reported IC$_{50}$ value is the geometric mean of ≥5 determinations.
$^c$The IC$_{50}$ value is from a single determination.
$^d$Not determined

We claim:
1. A compound of Formula I

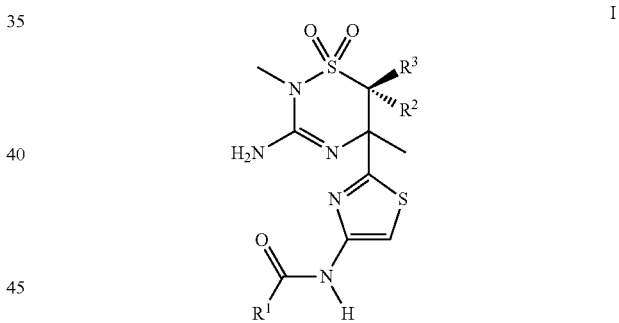

wherein

R$^1$ is a 5- to 6-membered heteroaryl, having one to four heteroatoms independently selected from N, O or S, wherein at least one of the heteroatoms is N and wherein said N is optionally substituted with R$^5$; and wherein said 5- to 6-membered heteroaryl is optionally substituted on carbon with one to three R$^4$;

R$^2$ and R$^3$ are each independently hydrogen, C$_{1-6}$alkyl, C$_{3-6}$cycloalkyl or 3- to 7-membered heterocycloalkyl; wherein the C$_{1-6}$alkyl is optionally substituted with a C$_{1-3}$alkoxy or with one to three fluoro; and the C$_{3-6}$cycloalkyl and 3- to 7-membered heterocycloalkyl are each optionally and independently substituted with one to three fluoro, C$_{1-3}$alkyl or C$_{1-3}$alkoxy;

or R$^2$ and R$^3$, taken together with the carbon to which they are attached, form a C$_{3-6}$cycloalkyl ring or 3- to 7-membered heterocycloalkyl ring, each of which is optionally and independently substituted with one to three fluoro, C$_{1-3}$alkyl or C$_{1-3}$alkoxy;

R⁴ at each occurrence is independently selected from the group consisting of halo, hydroxy, cyano, $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$alkyl, $C_{3-6}$cycloalkyl-$C_{1-6}$alkoxy, 4- to 6-membered heterocycloalkyl and 4- to 6-membered heterocycloalkyl-$C_{1-6}$alkyl; wherein said $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$alkyl, $C_{3-6}$cycloalkyl-$C_{1-6}$alkoxy, 4- to 6-membered heterocycloalkyl and 4- to 6-membered heterocycloalkyl-$C_{1-6}$alkyl are each optionally substituted with one to three substituents independently selected from fluoro, chloro, hydroxy, cyano, methyl, fluoromethyl, difluoromethyl, trifluoromethyl, methoxy, fluoromethoxy, difluoromethoxy and trifluoromethoxy; and R⁵ is hydrogen or $C_{1-6}$alkyl optionally substituted with one to three fluoro;

or a tautomer thereof or a pharmaceutically acceptable salt of said compound
or tautomer.

2. The compound of claim 1 of Formula Ia

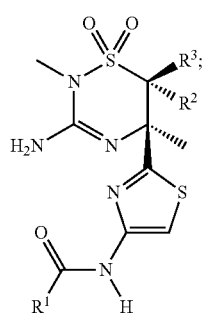

or a tautomer thereof or a pharmaceutically acceptable salt of said compound or tautomer.

3. The compound of claim 1 of Formula Ib

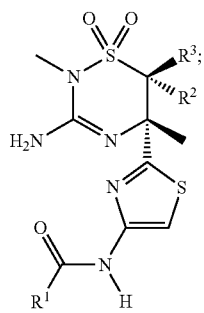

or a tautomer thereof or a pharmaceutically acceptable salt of said compound or tautomer.

4. The compound of claim 1 wherein

R¹ is pyrazolyl substituted with R⁵; or oxazolyl, pyridinyl or pyrazinyl substituted with one or two R⁴;

or a tautomer thereof or a pharmaceutically acceptable salt of said compound or tautomer.

5. The compound of claim 4 wherein

R⁴ at each occurrence is independently selected from the group consisting of halo, cyano, $C_{1-3}$alkyl optionally substituted with one to three fluoro, $C_{1-3}$alkoxy optionally substituted with one to three fluoro, and $C_{3-4}$alkynyloxy;

R⁵ is $C_{1-3}$alkyl optionally substituted with one to three fluoro;

or a tautomer thereof or a pharmaceutically acceptable salt of said compound or tautomer.

6. The compound of claim 5 wherein

R¹ is 1-(difluoromethyl)-1H-pyrazol-3-yl, 2-(fluoromethyl)-1,3-oxazol-4-yl, 5-(difluoromethoxy)-pyridin-2-yl, 5-(difluoromethoxy)-3-methylpyridin-2-yl, 3-chloro-5-(difluoromethoxy)pyridin-2-yl, 5-cyanopyridin-2-yl, 5-cyano-3-methylpyridin-2-yl, 3-chloro-5-cyanopyridin-2-yl, 5-(but-2-yn-1-yloxy)pyridin-2-yl, 5-fluoromethyl)pyrazin-2-yl, 5-(difluoromethyl)pyrazin-2-yl, 5-(2,2-difluoropropoxy)pyrazin-2-yl or 5-(but-2-yn-1-yloxy)pyrazin-2-yl;

or a tautomer thereof or a pharmaceutically acceptable salt of said compound or tautomer.

7. The compound of claim 6 wherein
R² and R³ are each hydrogen;
or a tautomer thereof or a pharmaceutically acceptable salt of said compound or tautomer.

8. The compound of claim 6 wherein
R² and R³ are each methyl;
or a tautomer thereof or a pharmaceutically acceptable salt of said compound or tautomer.

9. The compound of claim 6 wherein one of R² and R³ is hydrogen and the other is methyl, ethyl, cyclopropyl, 1-methylcyclopropyl or 2,2-dimethylcyclopropyl;
or a tautomer thereof or a pharmaceutically acceptable salt of said compound or tautomer.

10. The compound of claim 6 wherein
R² and R³, taken together with the carbon to which they are attached, form a cyclopropyl, cyclobutyl or cyclopentyl ring;
or a tautomer thereof or a pharmaceutically acceptable salt of said compound or tautomer.

11. The compound of claim 1 wherein
R² and R³ are each hydrogen;
or a tautomer thereof or a pharmaceutically acceptable salt of said compound or tautomer.

12. The compound of claim 1 wherein
R² and R³ are each methyl;
or a tautomer thereof or a pharmaceutically acceptable salt of said compound or tautomer.

13. The compound of claim 1 wherein one of R² and R³ is hydrogen and the other is methyl, ethyl, cyclopropyl, 1-methylcyclopropyl or 2,2-dimethylcyclopropyl;
or a tautomer thereof or a pharmaceutically acceptable salt of said compound or tautomer.

14. The compound of claim 1 wherein
R² and R³, taken together with the carbon to which they are attached, form a cyclopropyl, cyclobutyl or cyclopentyl ring;
or a tautomer thereof or a pharmaceutically acceptable salt of said compound or tautomer.

15. The compound of claim 1 selected from the group consisting of
N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;
N-{2-[(5S)-3-amino-2,5-dimethyl-1,1-dioxido-5,6-dihydro-2H-1,2,4-thiadiazin-5-yl]-1,3-thiazol-4-yl}-1-(difluoromethyl)-1H-pyrazole-3-carboxamide;

N-{2-[(5R,6S)-3-amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S,6R)-3-amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S,6S)-3-amino-6-cyclopropyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-[2-(3-amino-2,5,6,6-tetramethyl-1,1-dioxido-5,6-dihydro-2H-1,2,4-thiadiazin-5-yl)-1,3-thiazol-4-yl]-5-(difluoromethoxy)pyridine-2-carboxamide;

N-{2-[(5R)-3-amino-2,5,6,6-tetramethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S)-3-amino-2,5,6,6-tetramethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)-3-methylpyridine-2-carboxamide;

N-{2-[(5R,6S)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S,6R)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S,6S)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5R,6R)-3-amino-2,5,6-trimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5R,6S)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S,6R)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5R,6R)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S,6S)-3-amino-6-ethyl-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-(difluoromethyl)pyrazine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-chloropyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-2-(fluoromethyl)-1,3-oxazole-4-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-(2,2-difluoropropoxy)pyrazine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-(but-2-yn-1-yloxy)pyrazine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-(but-2-yn-1-yloxy)pyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-3-chloro-5-(difluoromethoxy)pyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-cyanopyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-5-cyano-3-methylpyridine-2-carboxamide;

N-{2-[(5S)-3-amino-2,5-dimethyl-1,1-dioxido-5,6-dihydro-2H-1,2,4-thiadiazin-5-yl]-1,3-thiazol-4-yl}-3-chloro-5-cyanopyridine-2-carboxamide;

N-(2-{(5S,6R)-3-amino-6-[(1R)-2,2-dimethylcyclopropyl]-2,5-dimethyl-1,1-dioxido-5,6-dihydro-2H-1,2,4-thiadiazin-5-yl}-1,3-thiazol-4-yl)-5-(difluoromethoxy)-3-methylpyridine-2-carboxamide;

N-{2-[(5S,6R)-3-amino-2,5-dimethyl-6-(1-methylcyclopropyl)-1,1-dioxido-5,6-dihydro-2H-1,2,4-thiadiazin-5-yl]-1,3-thiazol-4-yl}-5-(difluoromethoxy)pyridine-2-carboxamide;

N-{2-[(8S)-6-amino-5,8-dimethyl-4,4-dioxido-4-thia-5,7-diazaspiro[2.5]oct-6-en-8-yl]-1,3-thiazol-4-yl}-5-(difluoromethoxy)pyridine-2-carboxamide;

N-{2-[(9S)-7-amino-6,9-dimethyl-5,5-dioxido-5-thia-6,8-diazaspiro[3.5]non-7-en-9-yl]-1,3-thiazol-4-yl}-5-(difluoromethoxy)pyridine-2-carboxamide; and N-{2-[(10S)-8-amino-7,10-dimethyl-6,6-dioxido-6-thia-7,9-iazaspiro[4.5]dec-8-en-10-yl]-1,3-thiazol-4-yl}-5-(difluoromethoxy)pyridine-2-carboxamide;

or a tautomer thereof or a pharmaceutically acceptable salt of said compound or tautomer.

16. The compound N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)pyridine-2-carboxamide;

or a tautomer thereof or a pharmaceutically acceptable salt of said compound or tautomer.

17. The compound N-{2-[(5S,6S)-3-amino-6-cyclopropyl-2,5-dimethyl-1,1-dioxido-5,6-dihydro)pyridine-2-carboxamide;

or a tautomer thereof or a pharmaceutically acceptable salt of said compound or tautomer.

18. The compound N-{2-[(5S)-3-amino-2,5-dimethyl-1,1-dioxido-5,6-dihydro-2H-1,2,4-thiadiazin-5-yl]-1,3-thiazol-4-yl}-5-(difluoromethoxy)-3-methylpyridine-2-carboxamide;

or a tautomer thereof or a pharmaceutically acceptable salt of said compound or tautomer.

19. A pharmaceutical composition comprising a therapeutically effective amount of a compound according to claim 1, or a tautomer thereof or a pharmaceutically acceptable salt of said compound or tautomer together with a pharmaceutically acceptable carrier.

20. A method of inhibiting production of amyloid-β protein, inhibiting beta-site amyloid precursor protein cleaving enzyme 1 (BACE1), treating Alzheimer's disease or treating Type 2 diabetes in a patient, the method comprising administering a therapeutically effective amount of a compound according to claim 1, or a tautomer thereof or a pharmaceutically acceptable salt of said compound or tautomer, to a patient in need of inhibition of production of amyloid-β protein, inhibition of beta-site amyloid precursor protein cleaving enzyme 1 (BACE1), treatment of Alzheimer's disease or treatment of Type 2 diabetes.

21. The method of claim 20 wherein Alzheimer's disease is treated.

22. The method of claim 20 wherein Type 2 diabetes is treated.

23. The method of claim 20 wherein production of amyloid-β protein is inhibited.

24. The method of claim 20 wherein beta-site amyloid precursor protein cleaving enzyme 1 (BACE1) is inhibited.

* * * * *